(12) United States Patent
Campos et al.

(10) Patent No.: US 7,629,470 B2
(45) Date of Patent: Dec. 8, 2009

(54) FORMATION OF TETRA-SUBSTITUTED ENAMIDES AND STEREOSELECTIVE REDUCTION THEREOF

(75) Inventors: Kevin R. Campos, Berkeley Heights, NJ (US); Artis Klapars, Scotch Plains, NJ (US); J. Christopher McWilliams, Hoboken, NJ (US); C. Scott Shultz, Maplewood, NJ (US); Debra J. Wallace, Scotch Plains, NJ (US); Alex M. Chen, Metuchen, NJ (US); Lisa F. Frey, Somerset, NJ (US); Andrey V. Peresypkin, Cranford, NJ (US); Yaling Wang, Westfield, NJ (US); Robert M. Wenslow, Cream Ridge, NJ (US); Cheng-Yi Chen, Plainsboro, NJ (US)

(73) Assignee: Merck & Co., Inc., Rahway, NJ (US)

( * ) Notice: Subject to any disclaimer, the term of this patent is extended or adjusted under 35 U.S.C. 154(b) by 286 days.

(21) Appl. No.: 11/629,005

(22) PCT Filed: Jul. 1, 2005

(86) PCT No.: PCT/US2005/023514

§ 371 (c)(1),
(2), (4) Date: Dec. 8, 2006

(87) PCT Pub. No.: WO2006/017045

PCT Pub. Date: Feb. 16, 2006

(65) Prior Publication Data

US 2009/0018340 A1    Jan. 15, 2009

Related U.S. Application Data

(60) Provisional application No. 60/586,306, filed on Jul. 8, 2004.

(51) Int. Cl.
*C07D 213/63* (2006.01)
(52) U.S. Cl. .................................... 546/290
(58) Field of Classification Search .................. 546/290
See application file for complete search history.

(56) References Cited

U.S. PATENT DOCUMENTS

| | | | |
|---|---|---|---|
| 5,191,095 A | 3/1993 | Manimaran et al. |
| 5,292,893 A | 3/1994 | Buchwald et al. |
| 5,442,119 A | 8/1995 | Buchwald et al. |
| 5,489,682 A | 2/1996 | Buchwald et al. |
| 5,491,233 A | 2/1996 | Buchwald et al. |
| 5,817,877 A | 10/1998 | Hartwig et al. |
| 5,907,045 A | 5/1999 | Antognazza et al. |
| 5,977,361 A | 11/1999 | Hartwig et al. |
| 6,077,958 A | 6/2000 | Antognazza et al. |
| 6,100,389 A | 8/2000 | Li et al. |
| 6,235,936 B1 | 5/2001 | Buchwald et al. |
| 6,235,938 B1 | 5/2001 | Hartwig et al. |
| 6,323,366 B1 | 11/2001 | Wolfe et al. |
| 6,465,664 B1 | 10/2002 | Buchwald et al. |
| 6,465,693 B2 | 10/2002 | Buchwald et al. |
| 6,545,165 B1 | 4/2003 | Fleming et al. |
| 6,566,552 B2 | 5/2003 | Tinti et al. |
| 6,586,357 B1 | 7/2003 | Antognazza et al. |
| 2002/0165408 A1 | 11/2002 | Tinti et al. |
| 2003/0158422 A1 | 8/2003 | Fleming et al. |
| 2003/0158423 A1 | 8/2003 | Fleming et al. |
| 2003/0171602 A1 | 9/2003 | Fleming et al. |
| 2004/0019216 A1 | 1/2004 | Buchwald et al. |

FOREIGN PATENT DOCUMENTS

| | | |
|---|---|---|
| EP | 0770085 | 9/1999 |
| EP | 1127886 | 5/2003 |
| EP | 1070075 | 10/2003 |
| WO | WO 00/29370 | 5/2000 |
| WO | WO 01/57014 | 8/2001 |
| WO | WO 03/066570 | 8/2003 |
| WO | WO 03/077847 | 9/2003 |
| WO | WO 03/078399 | 9/2003 |
| WO | WO 2004/048317 | 6/2004 |
| WO | WO2004/048317 | * 6/2004 |

OTHER PUBLICATIONS

Strauss et al., Inorg. Chem., vol. 17 (1978), pp. 3069-3074, "Lewis acid influenced ethylene hydrogenation by Rhodium(i) complexes".
Blaser et al., Applied Catalysis A: General, vol. 221 (2001), pp. 119-143, "Enantioselective catalysis in fine chemicals production".
Blaser et al., Adv. Synth. Catal., vol. 345 (2003), pp. 103-151, "Selective hydrogenation for fine chemicals: Recent trends and new developments".
Huang et al., JACS, vol. 125 (2003), pp. 6653-6655, "Expanding Pdcatalyzed C-N bond-forming processes . . . ".
Wallace et al., Org. Lett., vol. 5 (2003), pp. 4749-4752, "Palladium-catalyzed amidation of enol triflates . . . ".

(Continued)

*Primary Examiner*—Rei-tsang Shiao
(74) *Attorney, Agent, or Firm*—Baerbel R. Brown; Catherine D. Fitch

(57) ABSTRACT

The present invention is directed to a practical process for the preparation of an enamide (II) by palladium catalyzed coupling of a primary amide (IV) with a compound of structural formula (III), as shown below: As well as to crystalline forms of a compound produced by this process, in particular, an anhydrous crystal form, Form B, and crystalline solvates falling into three patterns, Type 1, Type 2, and Type 3, and crystalline intermediate compounds produced in the process. Still further, the present invention relates to the stereoselective reduction of the tetrasubstituted enamide (II) to the corresponding amide (I).

10 Claims, 28 Drawing Sheets

OTHER PUBLICATIONS

Anderson et al., J. Org. Chem., vol. 68 (2003), pp. 9563-9573, "Palladium-catalyzed amination of aryl nonaflates".

Yin et al., JACS, vol. 124 (2002), pp. 6043-6048, "Pd-catalyzed intermolecular amidation of aryl halides . . .".

Tang et al., Chem. Rev., vol. 103 (2003), pp. 3029-3069, "New chiral phosphorus ligands for enantioselective hydrogenation".

Benincori et al., J. Org. Chem., vol. 65 (2000), pp. 2043-2047, "2,2',5,5'-Tetramethyl-4,4'-bis(diphenylphoshino)-3,3'-bithiophene . . .".

Dobler et al., Tetrahedron: Asymmetry, vol. 7 (1996), pp. 117-125, "Unusual amino acids vil asynmmetric synthesis of 3- and 4-pyridylalanines".

* cited by examiner

FORMATION OF TETRA-SUBSTITUTED ENAMIDES AND STEREOSELECTIVE REDUCTION THEREOF

CROSS-REFERENCE TO RELATED APPLICATIONS

This application is a U.S. National Phase application under 35 U.S.C. §371 of PCT Application No. PCT/US2005/023514, filed Jul. 1, 2005, which claims priority under 35 U.S.C. §119 from U.S. provisional application No. 60/586,306, filed Jul. 8, 2004.

BACKGROUND OF THE INVENTION

The present invention is related to processes for synthesis of a tetrasubstituted enamide and asymmetric reduction of the tetrasubstituted enamide to form the chiral amide, and intermediate compounds obtained during the process. These processes are useful in the synthesis of pharmaceutically useful compounds, particularly those described in WO 03/077847. In WO 03/077847, synthesis of these compounds is achieved by non-stereoselective means and resolution of the isomers by chiral HPLC, which is not amenable to large scale production and produces excessive amounts of the undesired isomer.

US 2004/0019216 and Huang et al., JACS 125:6653-6655 (2003) disclose copper catalyzed carbon-heteroatom bond formation, and particularly carbon-nitrogen bond formation between a nitrogen of an amide or amine moiety and the activated carbon of an aryl, heteroaryl or vinyl halide or sulfonate. Wallace et al., Org. Lett. 5(24): 4749-4752 (2003) describe the formation of enamides by palladium catalyzed coupling of enol triflates with amides, carbamates and sulfonamides. WO 03/066570 is directed to formation of N-aryl amides and N-aryl amines by reaction of a compound with a primary or secondary amino or amido group with an arylating compound, in the presence of a weak base and a transition metal catalyst comprising a Group 8 metal and at least one carbene-containing ligand. U.S. Pat. No. 6,235,936 and U.S. Pat. No. 6,465,693 are respectively concerned with arylation and vinylation of hydrazines, hydrazones, hydroxylamines and oximes by reacting the appropriate aryl or vinyl compound having an activated carbon with a leaving group with a transition metal catalyst to form a carbon-heteroatom bond. U.S. Pat. No. 5,817,877 is directed to preparation of an organic amine having at least one unsaturated group by contacting an unsaturated organic sulfonate with a reactant amine in the presence of base and a transition metal catalyst containing a Group 8 metal and a chelating ligand, e.g., a Group 15-substituted arylene or Group 15-substituted metallocene. U.S. Pat. No. 6,235,938 is directed to preparing N-aryl amine compounds by reacting a compound having a amino group with an arylating compound in the presence of a base and a transition metal catalyst comprising a Group 8 metal and a chelating bisphosphine ligand having at least one sterically hindered alkyl substituent. U.S. Pat. No. 6,323,366 is directed to preparation of primary aryl or vinyl amines by combining an activated aryl or vinyl group and an imine in the presence of a transition metal catalyst and transforming the resulting N-aryl imine to the desired primary aryl or vinyl amine. U.S. Pat. Nos. 6,100,389 and 5,977,361 relate to the preparation of N-aryl amine, and amide compounds. Anderson et al., J. Org. Chem. 68:9563-9573 (2003) describe Pd-catalyzed amination of aryl nonaflates ($ArOSO_2$—$(CF_2)_3CF_3$). Yin et al., JACS 124:6043-6048 (2002) describe Pd-catalyzed amidation of aryl halides.

The present invention involves palladium catalyzed coupling of primary amides with vinyl tosylates. Use of the vinyl tosylate avoids the use of vinyl triflates, which is not amenable to large scale production. Still further, the tosylate intermediate is crystalline and easy to handle. The process is a stereoselective enolization and coupling that produces the Z isomer in high purity.

The present invention involves asymmetric rhodium-catalyzed hydrogenation of tetrasubstituted enamides. This reaction involves high enantioselectivity. Still further, the use of a Lewis Acid such as $BF_3$.MeOH (or some other source of $BF_3$) permits the hydrogenation to be carried out at low $H_2$ pressure and reaction temperature, providing a safety and cost advantage with less catalyst than would otherwise be necessary. Still further, in a preferred embodiment, the present invention sets two chiral centers in the same reaction. Overall, the synthetic route of the present invention provides the additional benefit of not requiring the use of azide.

U.S. Pat. No. 6,465,664 is directed to methods for asymmetric 1,4-hydrogenation to cyclic and acyclic enoates and enones using a catalyst comprising copper and an asymmetric bidentate bisphosphine ligand. U.S. Pat. No. 5,489,682 is directed to catalytic asymmetric reduction of enamines with chiral metal catalysts selected from Groups 3, 4, 5, or 6, lanthanide and actinides. U.S. Pat. No. 5,292,893; U.S. Pat. No. 5,491,233 and U.S. Pat. No. 5,442,119 are directed to a catalytic asymmetric hydrogenation process for hydrogenation of tri-substituted olefins and enamines.

The present invention makes use of a chiral, transition metal catalyst. The use of chiral catalysts for stereoselective hydrogenations is described in Tang et al., Chem. Rev. 103: 3029 (2003); Blaser et al., Adv. Synth. Catal. 345: 103 (2003); and Blaser et al., Applied Catalysis A: General, 221:119 (2001). EP 0 770 085, U.S. Pat. No. 5,907,045, U.S. Pat. No. 6,077,958, U.S. Pat. No. 6,586,357 describe chiral phosphines and complexes between these diphosphines and transition metals comprising an aromatic pentatomic biheterocyclic system, including

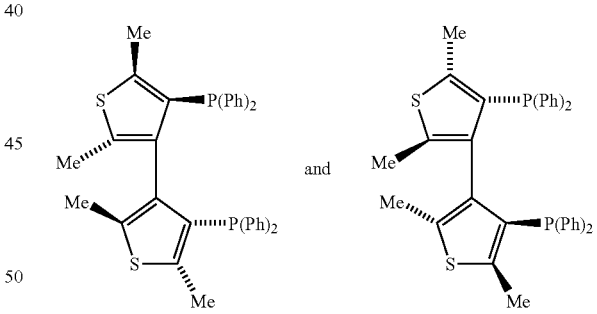

and their use in stereo controlled reductions. These ligands are also described in Benincori et al., J. Org. Chem. 65:2043-2047 (2000). EP 1 070 075 is directed to atropo-isomeric chiral phosphorated ligands having $C_1$, symmetry, and organometallic complexes containing phosphorated ligands in optically active form and their use in stereoselective organic syntheses.

WO 00/29370, U.S. Pat. No. 6,566,552, U.S. Pat. No. 6,545,165, US 2002/0165408 address processes for production of L-carnitine by enantioselective reduction of an oxo group to the optically active hydroxyl group, employing [(+) TMBTP)Ru(p-cymene) $I_2$].

WO 01/57014, US 2003/0158422, US 2003/0158423, US 2003/0171602, EP 1 127 886 are directed to the multistep production of a δ-lactone from an acyl halide preferably employing a Ruthenium (R) MeOBIPHEP catalyst in the enantioselective reduction.

WO 03/078399 is directed to asymmetric hydrogenation of hexahydroquinoline salts using an iridium or rhodium catalyst comprising a chiral diphosphine ligand of either of the formulae below:

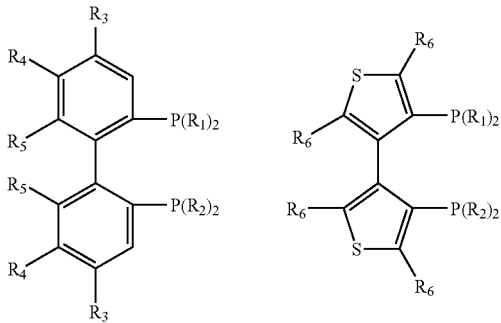

The use of $HBF_4$ in the hydrogenation of pyridine containing enamides with Rh catalysts is described in Döbler, Tetrahedron: Asymmetry 7:117 (1996). Still further Shriver discloses the use of a Lewis acid to promote Rh catalyzed hydrogenation of ethylene (not an asymmetric reaction), in Inorganic Chemistry 17:3069 (1978).

The present invention provides for a palladium catalyzed coupling of a primary amide with a vinyl tosylate in the presence of a palladium catalyst.

The present invention also provides for asymmetric hydrogenation of tetrasubstituted enamides with chiral rhodium catalysts.

Still further, the present invention provides for particular crystal forms of N-[1S,2S]-3-(4-chlorophenyl)-2-(3-cyanophenyl)-1-methylpropyl]-2-methyl-2-{[5-(trifluoromethylpyridin-2-yl)oxy]propanamide, a product which may be produced from the coupling and hydrogenation of the present invention.

SUMMARY OF THE INVENTION

Figure 1:
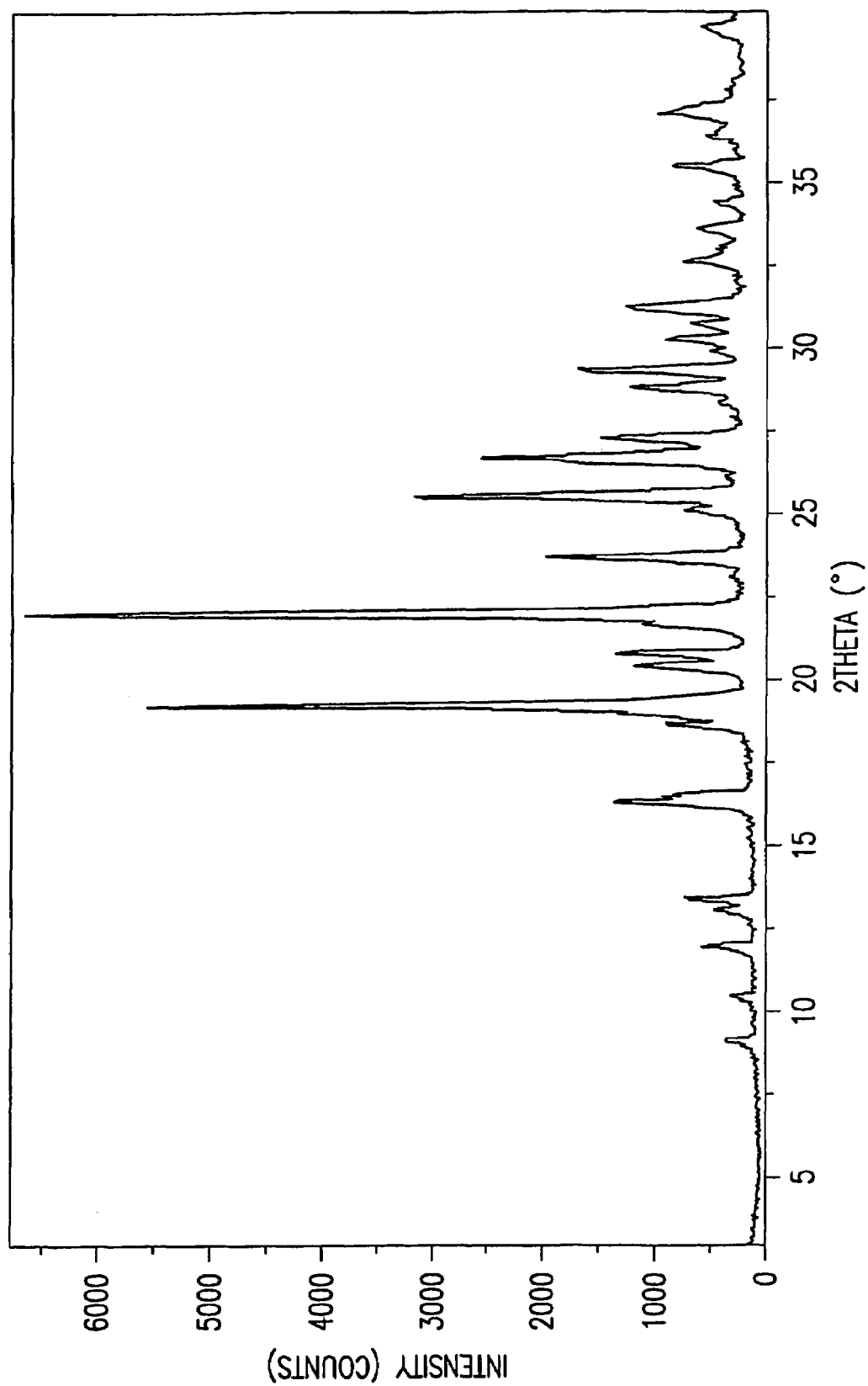
FIG. 1 shows the X-ray powder diffraction pattern (XRPD) of 3-[1-(4-chlorobenzyl)-2-oxopropyl]benzonitrile (EXAMPLE 2) generated on a Philips Analytical X'Pert PRO X-ray Diffraction System with PW3040/60 console using a PW3373/00 ceramic Cu LEF X-ray tube K-Alpha radiation as the source.

The present invention is directed to a practical process for the preparation of an enamide (II) by palladium catalyzed coupling of a primary amide (IV) with a compound of structural formula (III), as shown below:

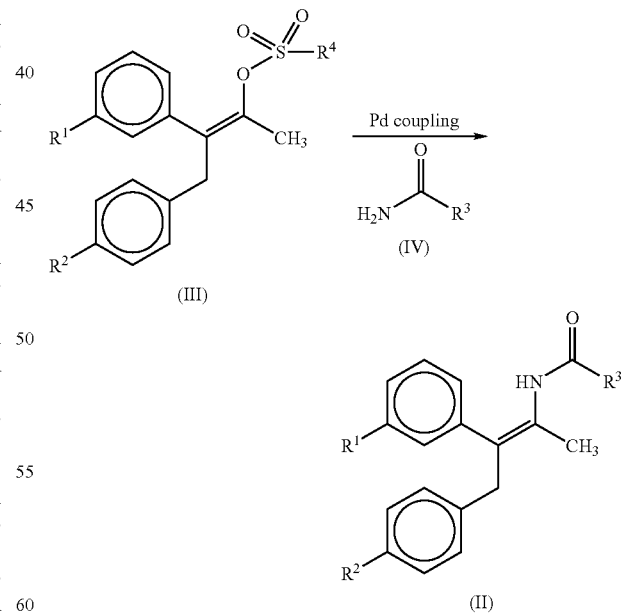

wherein:

$R^1$ is selected from: hydrogen, halogen, —C(O)OR$^e$, —C(O)NR$^f_2$, —NR$^f_2$, and cyano;

$R^2$ is selected from: hydrogen, halogen and hydroxyl;

R³ is selected from: hydrogen, straight or branched chain C$_{1-10}$ alkyl, wherein the alkyl moiety is unsubstituted or substituted with substituents selected from halogen, CF$_3$, OCF$_3$, and OR$^a$;

wherein R$^a$ is selected from cycloalkyl, aryl, aryl-C$_{1-3}$ alkyl- and heteroalkyl unsubstituted or substituted with one or two R$^b$ substituents independently selected from halogen, C$_{1-3}$ alkyl, cyano, methoxy and trifluoromethyl;

R⁴ is selected from: aryl, heteroaryl and C$_{1-10}$ alkyl, wherein the aryl and heteroaryl moieties are unsubstituted or substituted with one to three R$^c$ substituents, and the alkyl moiety is unsubstituted or substituted with one or two R$^d$ substituents;

each R$^c$ is independently selected from halogen, hydroxy, C$_{1-3}$ alkyl, cyano, methoxy and trifluoromethyl;

each R$^d$ is independently selected from: halogen, hydroxy, cyano, methoxy and trifluoromethyl;

R$^e$ is selected from: hydrogen, straight or branched chain C$_{1-10}$ alkyl, aryl-C$_{1-6}$ alkyl-, aryl, heteroaryl, wherein aryl and heteroaryl moieties are optionally substituted with one to three R$^c$ substituents, and the alkyl moiety is unsubstituted or substituted with one, two or three R$^d$ moieties;

each R$^f$ is independently selected from hydrogen, straight or branched chain C$_{1-6}$ alkyl, phenyl-C$_{1-6}$ alkyl-, wherein alkyl moieties are unsubstituted or substituted with one or two R$^d$ substituents and wherein the phenyl moiety is unsubstituted or substituted with one, two or three R$^c$ substituents.

Still further, the present invention relates to the stereoselective reduction of the tetrasubstituted enamide (II) to the corresponding amide (I):

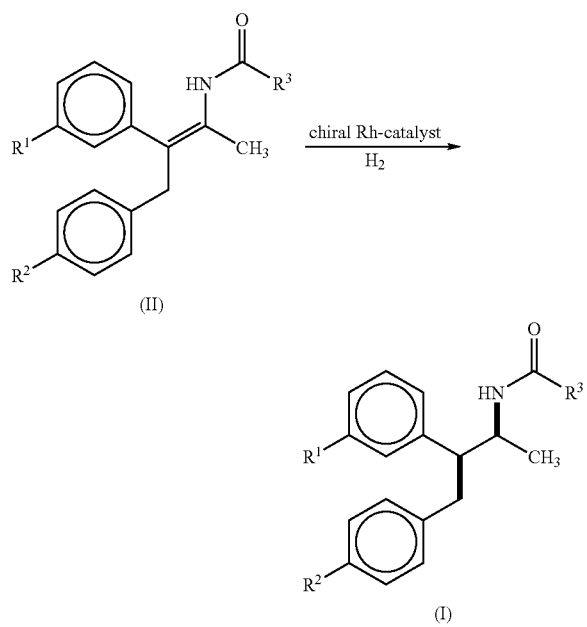

wherein R¹, R² and R³ are as described above.

In another aspect, the present invention relates to crystalline forms of N-[1S,2S]-3-(4-chlorophenyl)-2-(3-cyanophenyl)-1-methylpropyl]-2-methyl-2-{[5-trifluoromethyl pyridin-2-yl)oxy]propanamide, in particular, an anhydrous crystal form, Form B, and crystalline solvates falling into three patterns, Type 1, Type 2, and Type 3.

DETAILED DESCRIPTION OF THE INVENTION

The present invention is directed to a process for making enamide (II):

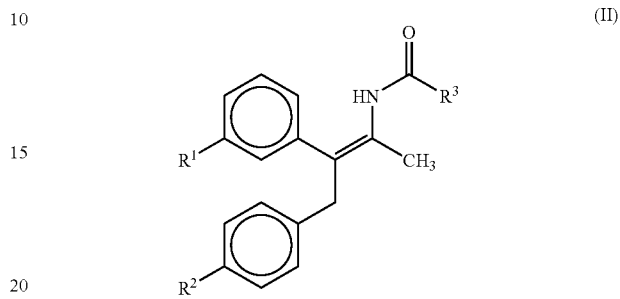

wherein:

R¹ is selected from: hydrogen, halogen, —C(O)OR$^e$, —C(O)NR$^f_2$, —NR$^f_2$, and cyano;

R² is selected from: hydrogen, halogen and hydroxyl;

R³ is selected from: hydrogen, straight or branched chain C$_{1-10}$ alkyl, wherein the alkyl moiety is unsubstituted or substituted with substituents selected from halogen, CF$_3$, OCF$_3$, and OR$^a$;

wherein R$^a$ is selected from cycloalkyl, aryl, aryl-C$_{1-3}$ alkyl- and heteroaryl unsubstituted or substituted with one or two R$^b$ substituents independently selected from halogen, C$_{1-3}$ alkyl, cyano, methoxy and trifluoromethyl;

each R$^c$ is independently selected from halogen, hydroxy, C$_{1-3}$ alkyl, cyano, methoxy and trifluoromethyl;

each R$^d$ is independently selected from: halogen, hydroxy, cyano, methoxy and trifluoromethyl;

R$^e$ is selected from: hydrogen, straight or branched chain C$_{1-10}$ alkyl, aryl-C$_{1-6}$ alkyl-, aryl, heteroaryl, wherein aryl and heteroaryl moieties are optionally substituted with one to three R$^c$ substituents, and the alkyl moiety is unsubstituted or substituted with one, two or three R$^d$ moieties; and each R$^f$ is independently selected from hydrogen, straight or branched chain C$_{1-6}$ alkyl, phenyl-C$_{1-6}$ alkyl-, wherein alkyl moieties are unsubstituted or substituted with one or two R$^d$ substituents and wherein the phenyl moiety is unsubstituted or substituted with one, two, or three R$^c$ substituents.

comprising:

treating a compound of formula (III):

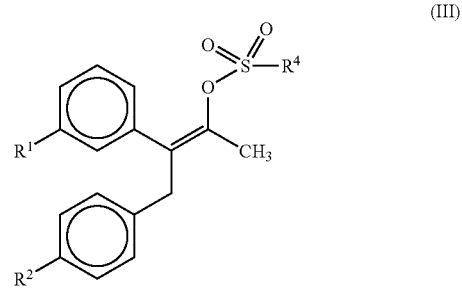

wherein $R^1$ and $R^2$ are defined above, and $R^4$ is selected from: aryl, heteroaryl and $C_{1-10}$ alkyl, wherein the aryl and heteroaryl moieties are unsubstituted or substituted with one to three $R^c$ substituents, and the alkyl moiety is unsubstituted or substituted with one or two $R^d$ substituents; with amide (IV):

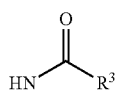

wherein:

$R^3$ is defined above;

in the presence of a base and a palladium catalyst.

In one embodiment of the present invention, $R^1$ is selected from: hydrogen, halogen, —C(O)OR$^e$, —C(O)NR$^f_2$, —NR$^f_2$, and cyano. In one class of this embodiment, $R^1$ is selected from hydrogen, chlorine, bromine, —C(O)OCH$_3$, NH$_2$, and cyano. In one class of this embodiment, $R^1$ is selected from —NH$_2$ and cyano. In one subclass of this class, $R^1$ is amido (—NH$_2$). In another subclass of this class, $R^1$ is cyano. In another class of this embodiment, $R^1$ is selected from chlorine and bromine. In one subclass, $R^1$ is bromine. In another class, $R^1$ is hydrogen.

In another embodiment of the present invention, $R^2$ is selected from hydrogen, fluorine, chlorine, and bromine. In one class, $R^2$ is selected from hydrogen and chlorine. In one subclass, $R^2$ is hydrogen. In another subclass, $R^2$ is chlorine.

In yet another embodiment of the present invention, $R^3$ is selected from hydrogen, and straight or branched $C_{1-10}$ alkyl, wherein the alkyl moiety is unsubstituted or substituted with halogen, —CF$_3$, —OCF$_3$, and —OR$^a$. In one class of this embodiment, $R^3$ is straight or branched $C_{1-8}$ alkyl, unsubstituted or substituted with halogen, —CF$_3$, —OCF$_3$, and —OR$^a$. In one subclass of this class, $R^3$ is selected from branched $C_{3-6}$ alkyl substituted with OR$^a$. In a subclass, $R^3$ is:

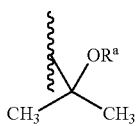

In one embodiment of the present invention, $R^a$ is selected from $C_{4-6}$ cycloalkyl, aryl, aryl-$C_{1-3}$ alkyl- and heteroaryl wherein $R^a$ may be unsubstituted or substituted with one or two $R^b$ substituents. In one class of this embodiment, $R^a$ is selected from phenyl, benzyl, pyridyl, and pyrimidyl, wherein $R^a$ may be unsubstituted or substituted with an $R^b$ substituent. In a subclass, $R^a$ is pyridyl substituted with trifluoromethyl. In yet another subclass, $R^a$ is

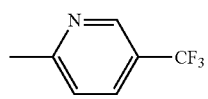

In one embodiment of the present invention, each $R^b$ is independently selected from fluoro, chloro, bromo, iodo, methyl, cyano and trifluoromethyl. In one class, each $R^b$ is independently selected from chloro, iodo, methyl, cyano and trifluoromethyl. In a subclass, each $R^b$ is trifluoromethyl.

In one embodiment of the present invention, $R^4$ is selected from: aryl, heteroaryl and $C_{1-10}$ alkyl, wherein the aryl and heteroaryl moieties are unsubstituted or substituted with one to three $R^c$ substituents, and the alkyl moiety is unsubstituted or substituted with one or two $R^d$ substituents; $R^4$ is selected from: aryl, heteroaryl and $C_{1-6}$alkyl wherein the aryl and heteroaryl moieties are unsubstituted or substituted with one to three $R^c$ substituents, and the alkyl moiety is unsubstituted or substituted with one or two $R^d$ substituents. In one class of this embodiment, $R^4$ is selected from phenyl, pyridyl, pyrimidinyl, and $C_{1-6}$alkyl, wherein the aryl and heteroaryl moieties are unsubstituted or substituted with one to three $R^c$ substituents, and the alkyl moiety is unsubstituted or substituted with one or two $R^d$ substituents. In one subclass of this class, $R^4$ is selected from phenyl, and pyridyl, $C_{3-6}$alkyl, wherein the aryl and heteroaryl moieties are unsubstituted or substituted with one or two $R^c$ substituents, and the alkyl moiety is unsubstituted or substituted with one or two $R^d$ substituents. In another subclass, $R^4$ is selected phenyl, wherein the phenyl is unsubstituted or substituted with an $R^c$ substituent. In yet another subclass, $R^4$ is 4-methylphenyl.

In one embodiment of the present invention, each $R^c$ is independently selected from halogen, $C_{1-3}$ alkyl, cyano, methoxy and trifluoromethyl. In one class of this embodiment, each $R^c$ is independently selected from: fluoro, chloro, methyl, and trifluoromethyl. In a subclass of this embodiment, $R^c$ is selected from fluoro, chloro and methyl. In another subclass, $R^c$ is methyl.

In another embodiment of the present invention, each $R^d$ is independently selected from: halogen, hydroxy, cyano, methoxy and trifluoromethyl. In one class of this embodiment, each $R^d$ is independently selected from fluoro, chloro, and trifluoromethyl. In a subclass of this class, each $R^d$ is independently selected from fluoro and chloro.

In another embodiment of the present invention, $R^e$ is selected from: hydrogen, straight or branched chain $C_{1-10}$ alkyl, aryl-$C_{1-6}$ alkyl, aryl, heteroaryl, wherein aryl and heteroaryl moieties are optionally substituted with one to three $R^c$ substituents, and the alkyl moiety is unsubstituted or substituted with one, two or three $R^d$ moieties. In one class of this embodiment, $R^e$ is selected from hydrogen, methyl, ethyl, isopropyl, t-butyl, benzyl, phenyl, and pyridyl, wherein the aryl and heteroaryl moieties are optionally substituted with one or two $R^c$ substituents, and the alkyl moiety is unsubstituted or substituted with one or two $R^d$ substituents. In one subclass of this class, $R^e$ is selected from hydrogen, methyl, t-butyl, benzyl, and phenyl. In yet another subclass, $R^e$ is hydrogen or methyl.

In yet another embodiment of the present invention, each $R^f$ is independently selected from hydrogen, straight or branched chain $C_{1-6}$ alkyl, phenyl-$C_{1-6}$ alkyl-, wherein alkyl moieties are unsubstituted or substituted with one or two $R^d$ substituents and wherein the phenyl moiety is unsubstituted or substituted with one, two or three $R^c$ substituents. In one class of this embodiment, each $R^f$ is independently selected from hydrogen, methyl, ethyl, isopropyl, t-butyl and benzyl, wherein alkyl moieties are unsubstituted or substituted with one or two $R^d$ substituents and wherein the phenyl moiety is unsubstituted or substituted with one, two or three $R^c$ substituents. In one subclass of this class, each $R^f$ is independently selected from hydrogen and methyl.

In one embodiment of the present invention, the base is an inorganic base. In one class of this embodiment the base is potassium carbonate. In another embodiment of the present invention, the palladium catalyst is any compound containing a palladium atom. In one class of this embodiment, the palladium catalyst is selected from tris(dibenzylideneacetone)

dipalladium(0), and bis(dibenzylidene-acetone)palladium (0). In a subclass of this class, the palladium catalyst is bis(dibenzylideneacetone)-palladium(0).

In one embodiment of the present invention, the palladium catalyst comprises a phosphine ligand. In one class of this embodiment, the phosphine ligand is a diphosphine ligand. In one subclass of this class, the phosphine ligand is selected from 1,4-bis(diphenylphosphino)butane, 1,1'-bis(diisopropyl-phosphino)ferrocene.

In one embodiment of the present invention, the reaction is carried out in a tertiary alcohol solvent, an arene solvent, or a mixture thereof. In one class of this embodiment the reaction is carried out in a tertiary alcohol solvent. In one subclass of this class, the solvent is tert-amyl alcohol. In another class of this embodiment, the reaction is carried out in a mixture of a tertiary alcohol solvent and an arene solvent. In a subclass of this class, the reaction is carried out in a mixture of tert-amyl alcohol and toluene.

This reaction can conducted over a broad range of temperatures. In one embodiment, the reaction mixture is heated above room temperature. In one class of this embodiment, the reaction is heated to between 50 and 140° C. In one subclass of this embodiment, the reaction is heated to between 80 to 120° C. In yet another subclass of this embodiment, the reaction is heated to between 90 to 110° C.

Similarly, this reaction can be conducted over a broad range of concentrations.

Still further, the present invention is concerned with the stereoselective reduction of enamide (II):

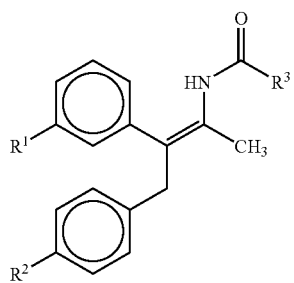

(II)

wherein $R^1$, $R^2$, and $R^3$ are as defined above, to the amide (I):

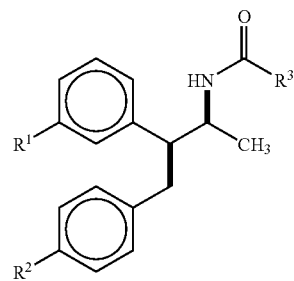

(I)

wherein $R^1$, $R^2$, and $R^3$ are as defined above, by treatment with hydrogen gas in the presence of a chiral catalyst.

The enamide II is generally dissolved in a solvent selected from methanol, ethanol, isopropanol, trifluoroethanol, THF, isopropyl acetate, ethyl acetate, toluene, methylene chloride, dichloroethane, DMA, DMF, water, and a combination of these solvents. The reaction is generally carried out at a concentration of about 5 to 200 g/L solvent. The reaction may be run at a temperature of from 0 to 100° C. The hydrogen gas is generally employed at a pressure between 1 and 100 atmospheres (101.3 kPa to 10,130 kPa).

An additive, such as acetic acid, tetrafluoroboric acid, trifluoroacetic acid, toluene sulfonic acid, methanesulfonic acid, phosphoric acid, citric acid or a Lewis acid such as: $BF_3$, $BF_3$.solvent, $B(OMe)_3$, $B(O-iPr)_3$, $LiBF_4$, $LiOTf$, $NaPF_6$, $Cs_2CO_3$, $MgSO_4$, $Sc(O-iPr)_3$, $Cu(OTf)_2$, $[[Cu(OTf)]_2$.benzene], $Cu(COCF_3)_2.H_2O$, $Zn(OTf)_3$, $Sc(OTf_3)$, $La(OTf)_3$, $Mg(OTf)_2$, $LiBF_4(DME)_3$, $K(BPh_4)$, and $BEt_3$ may be optionally employed in the reaction mixture. In one embodiment, the additive is selected from: tetrafluoroboric acid, trifluoroacetic acid, $BF_3$, $BF_3$.IPA and $BF_3$.MeOH. In one class of this embodiment, the additive is selected from: $BF_3$.IPA and $BF_3$.MeOH. The additive may be favorably employed between 0 and 200 mol %.

The chiral catalyst may be formed in situ by contacting a metal precursor, a ligand and optionally an activator. Alternatively, a pre-formed catalyst complex may be employed.

When the chiral catalyst is formed in situ, the metal precursor is favorably selected from: $(COD)Ru(methallyl)_2$, $[(COD)RhCl]_2$, $(COD)_2RhX$, $(NBD)_2RhX$, $Rh(acac)(CO)_2$, $Rh(ethylene)_2(acac)$, $Rh(CO_2)Cl_2$, $RuCl_2(COD)$, $Ru(Ar)X_2$, $[(COD)IrCl]_2$, and $(COD)_2IrX$, wherein:

X is independently selected from: Cl, Br, I, OTf, $BF_4$, $PF_6$, $Sb_6$, $ClO_4$, at each occurrence; and Ar is a benzene group, unsubstituted or substituted with one, two, three, four, five or six 6 $C_{1-6}$alkyl substituents, either straight chain or branched. In one embodiment of the present invention, Ar is benzene, unsubstituted or substituted with one to six methyl groups. In one class of this invention, Ar is selected from: benzene, p-cymene, toluene, hexamethylbezene, mesitylene. In one class of this invention, the metal precursor is selected from: $(COD)_2RhBF_4$, $(COD)_2RhOTf$, $(NBD)_2RhBF_4$, $(NBD)_2RhOTf$, and $(COD)Ru(methallyl)_2$. In a subclass of this class of this invention, the metal precursor is selected from: $(COD)_2RhBF_4$, $(COD)_2RhOTf$, $(NBD)_2RhBF_4$, and $(NBD)_2RhOTf$. Any chiral diphosphine may be favorably employed as the ligand. In particular, (R,S)-(di-t-butylphosphino) ferrocenyl-ethyldi-3,5-dimethylphenylphosphine, (R,S)-(di-t-butylphosphino)ferrocenyl-ethyldi-o-tolylphosphine, (R,S)-(di-t-butylphosphino)ferrocenyl-ethyldiphenylphosphine, (R,S)-(di-t-butylphosphino)ferrocenyl-ethyldi-4-methoxyphenylphosphine, (R,S)-(di-t-butylphosphino)ferrocenyl-ethyldi-4-trifluoromethylphenylphosphine, (R,S)-(di-t-butylphosphino)ferrocenyl-ethyldi-3,5-dimethylphenylphosphine, (R,S)-diphenylphosphino)ferrocenyl-ethyldi-t-butylphosphine, (−)-TMBTP, (R)-BINAP, (R)-tol-BINAP, (R)-xyl-BINAP, (R)-Hexahemp, (R)-Synphos, or (S)-xyl-Phanephos may be employed as the ligand. In one embodiment of the present invention, the ligand is selected from: (R,S)-(di-t-butylphosphino)ferrocenyl-ethyldi-o-tolylphosphine, (R,S)-(di-t-butylphosphino)ferrocenyl-ethyldi-1-napthylphosphine, (R,S)-(di-t-butylphosphino)ferrocenyl-ethyldi-3,5-dimethylphenylphosphine, (R,S)-(diphenylphosphino)ferrocenyl-ethyldi-t-butylphosphine, (−)-TMBTP, (R)-hexahemp, (R)-xyl-BINAP. In one class of this embodiment, the ligand is selected from: (R,S)-(di-t-butylphosphino)ferrocenyl-ethyldi-o-tolylphosphine and (−)-TMBTP. The catalyst activator may optionally be employed. Particular catalyst activators useful in the method of the present invention include: tetrafluoroboric acid, acetic acid, triflic acid, trifluoroacetic acid, toluene sulfonic acid and methanesulfonic acid. In one subclass of the present invention, the catalyst activator is tetrafluoroboric acid. In another subclass of the present invention, the catalyst activator is not employed.

When a preformed catalyst complex is employed, ((bisphosphine)(COD)RhX), (bisphosphine)(NBD)RhX), and (bisphosphine)RuX$_2$, may be favorably employed, wherein X is as defined above The reaction is generally carried out over 1 to 48 hours. In particular, the reaction may be carried out over 6 to 36 hours.

In one embodiment of the present invention, $R^1$ is amido. In one class of this embodiment, the solvent is selected from methanol, ethanol, isopropanol, 2,2,2-trifluoroethanol ("trifluoroethanol"), THF, and 1,2-dichloroethane. In a subclass of this class, the solvent is selected from methanol, ethanol, isopropanol, and trifluoroethanol, In another subclass of this class, the solvent is isopropyl alcohol.

In another class of this embodiment, the hydrogen pressure is between 1 and 100 atmospheres. In a subclass, the hydrogen pressure is 5 and 60 atmospheres. In another subclass of this class, the hydrogen pressure is between 20 and 40 atmospheres. In still another subclass of this class, the hydrogen pressure is from 10 to 40 atmospheres. In yet another class of this embodiment, the additive is selected from tetrafluoroboric acid, trifluororacetic acid and BF$_3$.MeOH. In a subclass of this embodiment, the additive is BF$_3$.MeOH. The additive may be favorably employed between 3 and 40 mol %, preferably between 20-40 mol %.

In still another class of this embodiment, the catalyst is selected from the preformed catalyst complex (−)-TMBTP (COD)RhBF$_4$, or a catalyst formed in situ by contacting a metal precursor, a ligand and optionally a catalyst activator. In one subclass of this class, the metal precursor is (COD)$_2$RhBF$_4$. In another subclass of this class, the ligand is selected from: (R,S)-(di-t-butylphosphino)ferrocenyl-ethyldi-o-tolylphosphine, (R,S)-(diphenylphosphino)ferrocenyl-ethyldi-t-butylphosphine, (−)-TMBTP, (R)-Hexaphemp, and (R)-xyl-BINAP. In another subclass, the ligand is (−)-TMBTP. In yet another subclass of this invention, the catalyst activator is tetrafluoroboric acid. In still another subclass of this invention, the catalyst activator is not present.

In a further class of this embodiment, the substrate:catalyst ratio is from 10 to 5000. In a subclass of this class, the substrate:catalyst ratio is 100 to 1000. In yet another subclass of this class, the substrate:catalyst molar ratio is 200 to 500. In an additional class of this embodiment, the reaction temperature is from ambient to 90° C. In one subclass, the reaction temperature is from 20 to 50° C. In another subclass of this class, the reaction temperature is from 25 to 35° C. In yet another subclass of this class, the temperature is from 35 to 65° C. In another class of this embodiment, the reaction is run for between 18 and 24 hours. In yet another class of this invention, the reaction is run at a concentration of 50 to 150 g/L solvent. In a subclass of this invention a concentration of 80 to 120 g/L solvent is favorably employed.

In another embodiment of the present invention, $R^1$ is cyano.

In a class of this embodiment, the cyanoenamide II is dissolved in a solvent selected from methanol, THF and dichloroethane. In a subclass of this class, the cyanoenamide II is dissolved in dichloroethane.

In one class of this embodiment, the hydrogen pressure is between 20 to 80 atmospheres. In a subclass of this class, the hydrogen pressure is between 30 and 60 atmospheres. In another class of this embodiment, the additive is absent or BF$_3$.MeOH. In a subclass of this class, the additive is absent and not employed in the reaction mixture. The additive may be favorably employed between 0 and 40 mol %, preferably the additive is not present (0 mol %).

In another class of this embodiment, the catalyst selected for the cyanoenamide is selected from the preformed catalyst complex: (R,S)-(di-t-butylphosphino)ferrocenyl-ethyldi-3,5-dimethylphenylphosphine (COD)RhBF$_4$, and a catalyst formed in situ by contacting a metal precursor, a ligand and optionally a catalyst activator. In one subclass of this class, the metal precursor is: (NBD)2RhBF4. In another subclass of this class, the ligand is selected from: (R,S)-(di-t-butylphosphino)ferrocenyl-ethyldi-3,5-dimethylphenylphosphine, (−)-TMBTP, and (R)-Hexaphemp. In still another subclass of this class, the ligand is (R,S)-(di-t-butylphosphino)ferrocenyl-ethyldi-3,5-dimethylphenylphosphine. In yet another subclass, the catalyst activator is tetrafluoroboric acid. In still another subclass of this invention, the catalyst activator is not present.

In a further class of this embodiment, the substrate:catalyst molar ratio in the cyanoenamide reaction is from 10 to 500. In a subclass of this class, the substrate:catalyst molar ratio is from 20 to 100. In yet another subclass of this class, the substrate:catalyst molar ratio is from 30 to 50.

In an additional class of this embodiment, the reaction temperature of the cyanoenamide reaction is from 50° to 90° C. In a subclass of this class, the reaction temperature is from 75° to 85° C. In another class, the cyanoenamide reaction is run at a concentration of 10 to 100 g/L solvent. In a subclass of this invention, a concentration of 60-100 g/L is favorably employed.

Yet another embodiment of the present invention is directed to crystal forms of anhydrous and solvated N-[1S,2S-3-(4-chlorophenyl)-2-(3-cyanophenyl)-1-methylpropyl]-2-methyl-2-{[5-(trifluoromethyl pyridin-2-yl)oxy]propanamide.

Figure 16:
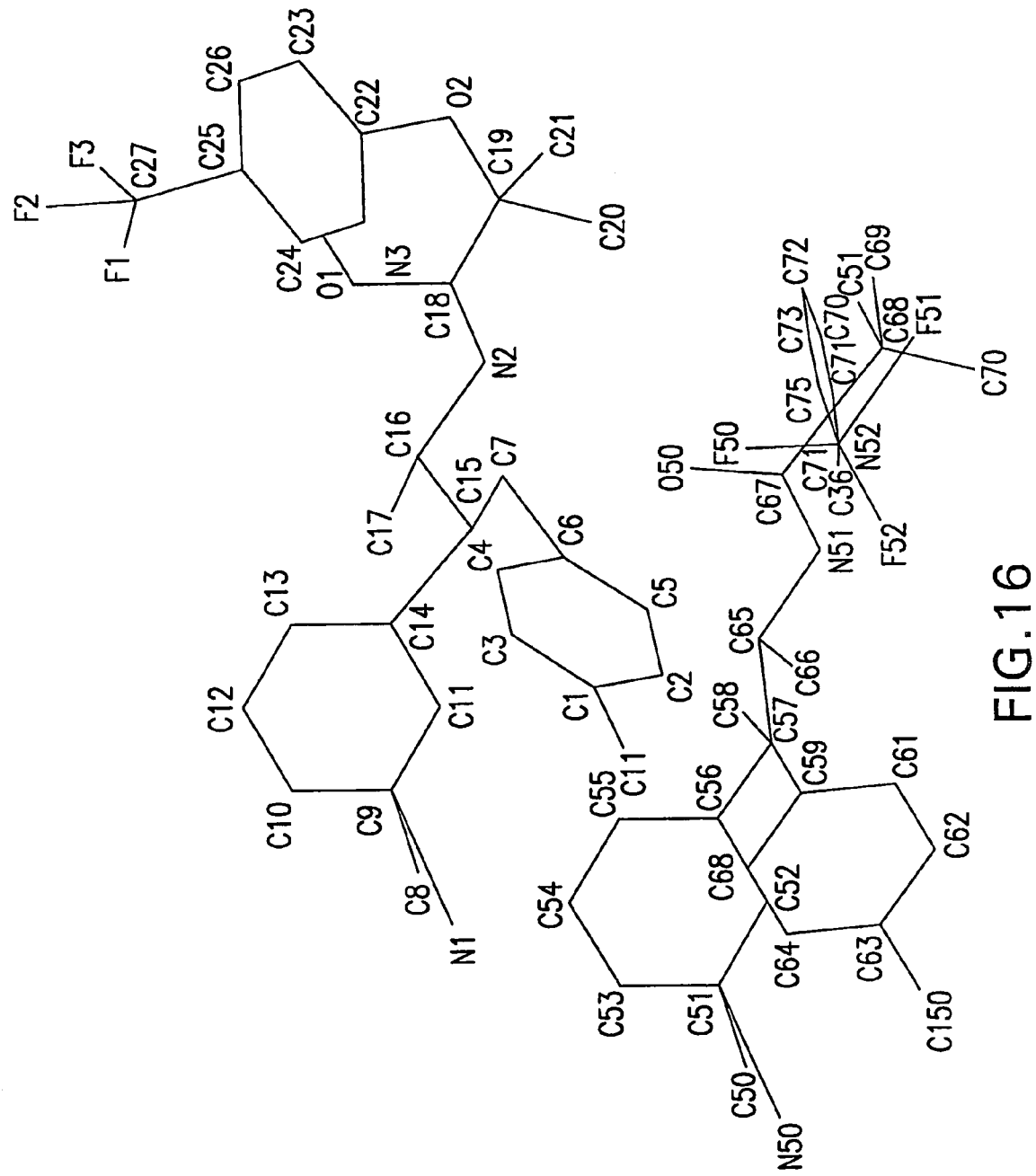
FIG. 16 is a computer generated perspective view of the two molecules in an asymmetric unit of Form B N-[1S,2S]-3-(4-chlorophenyl)-2-(3-cyanophenyl)-1-methylpropyl]-2-methyl-2-{[5-(trifluoromethylpyridin-2-yl)oxy}propanamide.

Form B of N-[1S,2S]-3-(4-chlorophenyl)-2-(3-cyanophenyl)-1-methylpropyl]-2-methyl-2-{[5-(trifluoromethyl pyridin-2-yl)oxy]propanamide is an anhydrous crystal form. Its structure was determined by single crystal X-ray crystallography. The crystals are triclinic with space group P1 and cell constants of a=10.6199 Å, b=11.058 Å, c=12.299 Å, α=112.476°, β=92.403°, and γ=93.453°. There are two molecules of N-[1S,2S]-3-(4-chlorophenyl)-2-(3-cyanophenyl)-1-methylpropyl-2-methyl-2-{[5-(trifluoromethyl pyridin-2-yl)oxy]propanamide in the asymmetric unit. A computer-generated (perspective view of the two molecules in an asymmetric unit is shown in FIG. 16. Lists of atomic parameters are given in Table 1.

TABLE 1

| Label | Xfrac | Yfrac | Zfrac | Label | Xfrac | Yfrac | Zfrac |
|---|---|---|---|---|---|---|---|
| C1 | 0.5047 | 0.6599 | 0.2834 | C50 | −0.144 | −0.1019 | 0.0835 |
| C2 | 0.434 | 0.602 | 0.3415 | C51 | −0.02 | −0.0614 | 0.1407 |
| H2 | 0.3464 | 0.6032 | 0.3372 | C52 | −0.0021 | 0.0394 | 0.2507 |

TABLE 1-continued

| Label | Xfrac | Yfrac | Zfrac | Label | Xfrac | Yfrac | Zfrac |
|---|---|---|---|---|---|---|---|
| C3 | 0.6308 | 0.6561 | 0.2886 | H52 | −0.071 | 0.0818 | 0.2873 |
| H3 | 0.6793 | 0.6935 | 0.2465 | C53 | 0.0817 | −0.1251 | 0.0843 |
| C4 | 0.6897 | 0.5975 | 0.3558 | H53 | 0.0694 | −0.1926 | 0.0101 |
| H4 | 0.7775 | 0.6 | 0.3617 | C54 | 0.199 | −0.0875 | 0.139 |
| C5 | 0.4917 | 0.541 | 0.4076 | H54 | 0.2678 | −0.1293 | 0.1019 |
| H5 | 0.4422 | 0.5029 | 0.4485 | C55 | 0.2176 | 0.012 | 0.2489 |
| C6 | 0.6199 | 0.5356 | 0.4139 | H55 | 0.299 | 0.0356 | 0.2852 |
| C7 | 0.6802 | 0.4629 | 0.4791 | C56 | 0.1183 | 0.0779 | 0.307 |
| H7A | 0.6582 | 0.4993 | 0.5605 | C57 | 0.1387 | 0.1904 | 0.4247 |
| H7B | 0.7714 | 0.476 | 0.4791 | H57 | 0.0557 | 0.2222 | 0.4473 |
| C8 | 0.4312 | 0.1017 | 0.0248 | C58 | 0.2225 | 0.3055 | 0.4184 |
| C9 | 0.5479 | 0.1578 | 0.0995 | H58A | 0.25 | 0.3654 | 0.4982 |
| C10 | 0.6605 | 0.1631 | 0.0498 | H58B | 0.2974 | 0.2715 | 0.3788 |
| H10 | 0.6645 | 0.1289 | −0.0317 | C59 | 0.1608 | 0.3811 | 0.3561 |
| C11 | 0.5426 | 0.203 | 0.2206 | C60 | 0.1659 | 0.3523 | 0.2356 |
| H11 | 0.466 | 0.1952 | 0.2523 | H60 | 0.2061 | 0.2798 | 0.189 |
| C12 | 0.7655 | 0.2196 | 0.1227 | C61 | 0.0981 | 0.4888 | 0.42 |
| H12 | 0.8421 | 0.226 | 0.0906 | H61 | 0.0902 | 0.509 | 0.4999 |
| C13 | 0.7609 | 0.2674 | 0.2431 | C62 | 0.0468 | 0.5674 | 0.3685 |
| H13 | 0.8343 | 0.306 | 0.291 | H62 | 0.0069 | 0.6408 | 0.4138 |
| C14 | 0.649 | 0.2592 | 0.2945 | C63 | 0.0547 | 0.5373 | 0.2522 |
| C15 | 0.6406 | 0.315 | 0.4266 | C64 | 0.112 | 0.4303 | 0.1846 |
| H15 | 0.5518 | 0.3033 | 0.4419 | H64 | 0.1149 | 0.4094 | 0.104 |
| C16 | 0.7177 | 0.2387 | 0.4838 | C65 | 0.1922 | 0.1461 | 0.5214 |
| H16 | 0.8056 | 0.2444 | 0.464 | H65 | 0.2763 | 0.1162 | 0.501 |
| C17 | 0.6698 | 0.0942 | 0.4383 | C66 | 0.1102 | 0.0341 | 0.5307 |
| H17A | 0.5818 | 0.0866 | 0.4518 | H66A | 0.0267 | 0.061 | 0.5489 |
| H17B | 0.7171 | 0.0512 | 0.4792 | H66B | 0.1463 | 0.0106 | 0.592 |
| H17C | 0.6803 | 0.0537 | 0.3553 | H66C | 0.1054 | −0.0403 | 0.4569 |
| C18 | 0.8199 | 0.3182 | 0.6836 | C67 | 0.3177 | 0.3211 | 0.6889 |
| C19 | 0.8065 | 0.3717 | 0.8157 | C68 | 0.3133 | 0.4176 | 0.8159 |
| C20 | 0.6771 | 0.3441 | 0.8531 | C69 | 0.3442 | 0.3434 | 0.8946 |
| H20A | 0.6806 | 0.3718 | 0.9374 | H69A | 0.3599 | 0.4045 | 0.9749 |
| H20B | 0.6523 | 0.2516 | 0.8169 | H69B | 0.418 | 0.297 | 0.8692 |
| H20C | 0.6164 | 0.3913 | 0.8287 | H69C | 0.274 | 0.2818 | 0.8891 |
| C21 | 0.8428 | 0.5173 | 0.8621 | C70 | 0.1902 | 0.4839 | 0.8488 |
| H21A | 0.9285 | 0.5324 | 0.8455 | H70A | 0.1688 | 0.5249 | 0.7952 |
| H21B | 0.8356 | 0.5547 | 0.9458 | H70B | 0.2012 | 0.5491 | 0.9279 |
| H21C | 0.7875 | 0.5574 | 0.8245 | H70C | 0.1234 | 0.4192 | 0.8441 |
| C22 | 0.913 | 0.1899 | 0.8318 | C71 | 0.4261 | 0.6046 | 0.7938 |
| C23 | 1.0134 | 0.1505 | 0.8831 | C72 | 0.5232 | 0.704 | 0.8402 |
| H23 | 1.0689 | 0.2117 | 0.9416 | H72 | 0.5797 | 0.7059 | 0.9009 |
| C24 | 0.8477 | −0.0198 | 0.7146 | C73 | 0.5342 | 0.7991 | 0.7947 |
| H24 | 0.7914 | −0.0795 | 0.6559 | H73 | 0.5994 | 0.8657 | 0.8228 |
| C25 | 0.945 | −0.0671 | 0.7609 | C74 | 0.3562 | 0.6903 | 0.6646 |
| C26 | 1.0282 | 0.0205 | 0.8454 | H74 | 0.2994 | 0.6852 | 0.603 |
| H26 | 1.0951 | −0.0088 | 0.8773 | C75 | 0.4472 | 0.7944 | 0.7069 |
| C27 | 0.9585 | −0.2062 | 0.7167 | C76 | 0.4526 | 0.8926 | 0.6547 |
| C11 | 0.4303 | 0.7364 | 0.202 | C150 | −0.0079 | 0.6375 | 0.188 |
| F1 | 0.8682 | −0.2816 | 0.6611 | F50 | 0.547 | 0.8831 | 0.5872 |
| F2 | 1.0437 | −0.2412 | 0.6414 | F51 | 0.4923 | 1.0121 | 0.7347 |
| F3 | 1.0081 | −0.2508 | 0.7861 | F52 | 0.3605 | 0.8981 | 0.5953 |
| H2A | 0.633 | 0.307 | 0.643 | N50 | −0.2412 | −0.1346 | 0.0386 |
| N1 | 0.3364 | 0.0629 | −0.0277 | N51 | 0.2058 | 0.2568 | 0.6354 |
| N2 | 0.7154 | 0.2967 | 0.6121 | H51 | 0.1383 | 0.2826 | 0.6706 |
| N3 | 0.831 | 0.1084 | 0.7508 | N52 | 0.3452 | 0.5953 | 0.708 |
| O1 | 0.9261 | 0.3049 | 0.646 | O50 | 0.4189 | 0.2973 | 0.6424 |
| O2 | 0.9028 | 0.321 | 0.8702 | O51 | 0.4185 | 0.5152 | 0.8451 |

Figure 17:
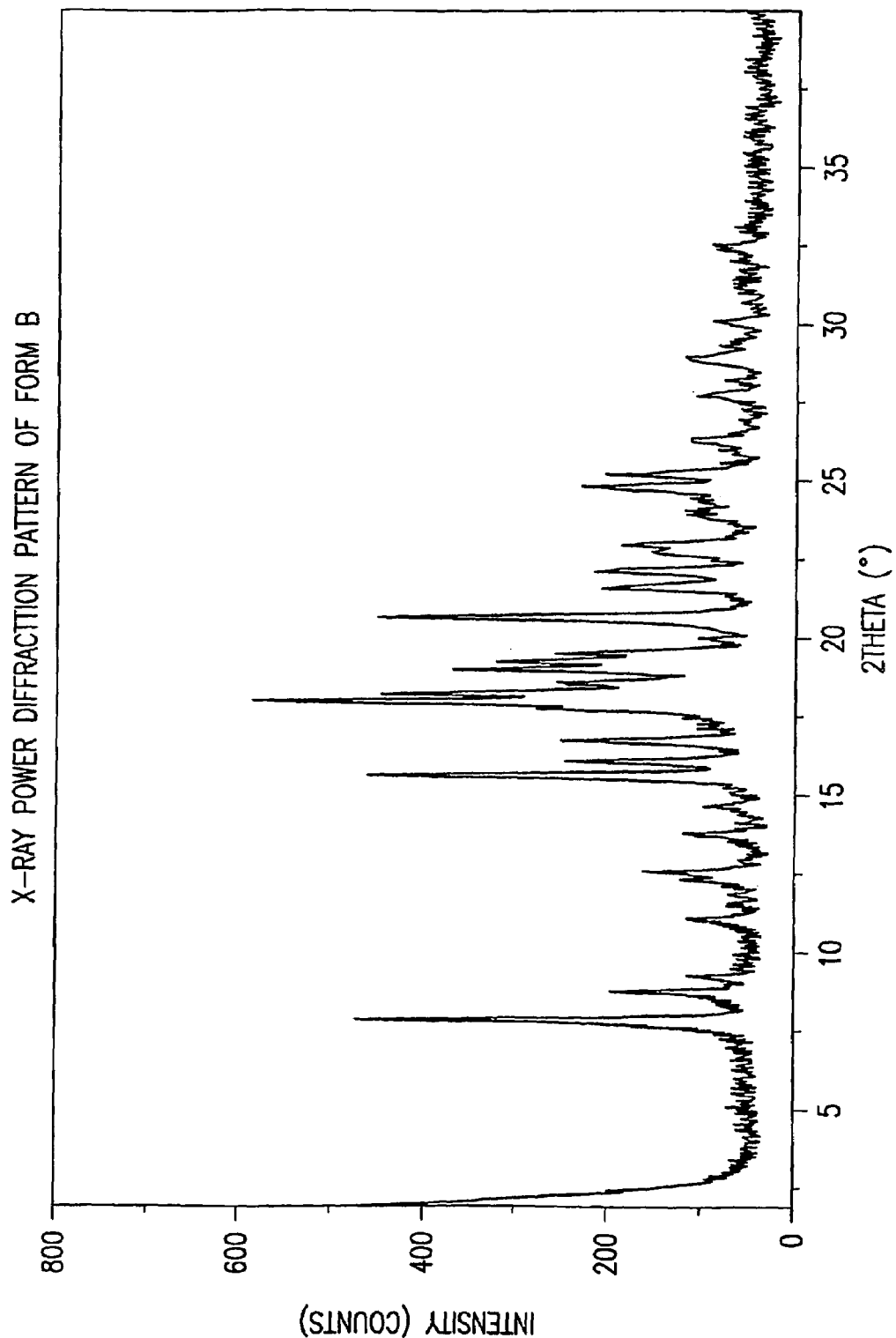
FIG. 17 shows the X-ray powder diffraction pattern of Form B N-[1S,2S]-3-(4-chlorophenyl)-2-(3-cyanophenyl)-1-methylpropyl]-2-methyl-2-{[5-(trifluoromethyl pyridin-2-yl)oxy]propanamide, generated on a Philips Analytical X'Pert PRO X-ray Diffraction System with PW3040/60 console using PW33373/00 ceramic CU LEF Xray tube K-ALPHa radiation as the source.
Figure 18:
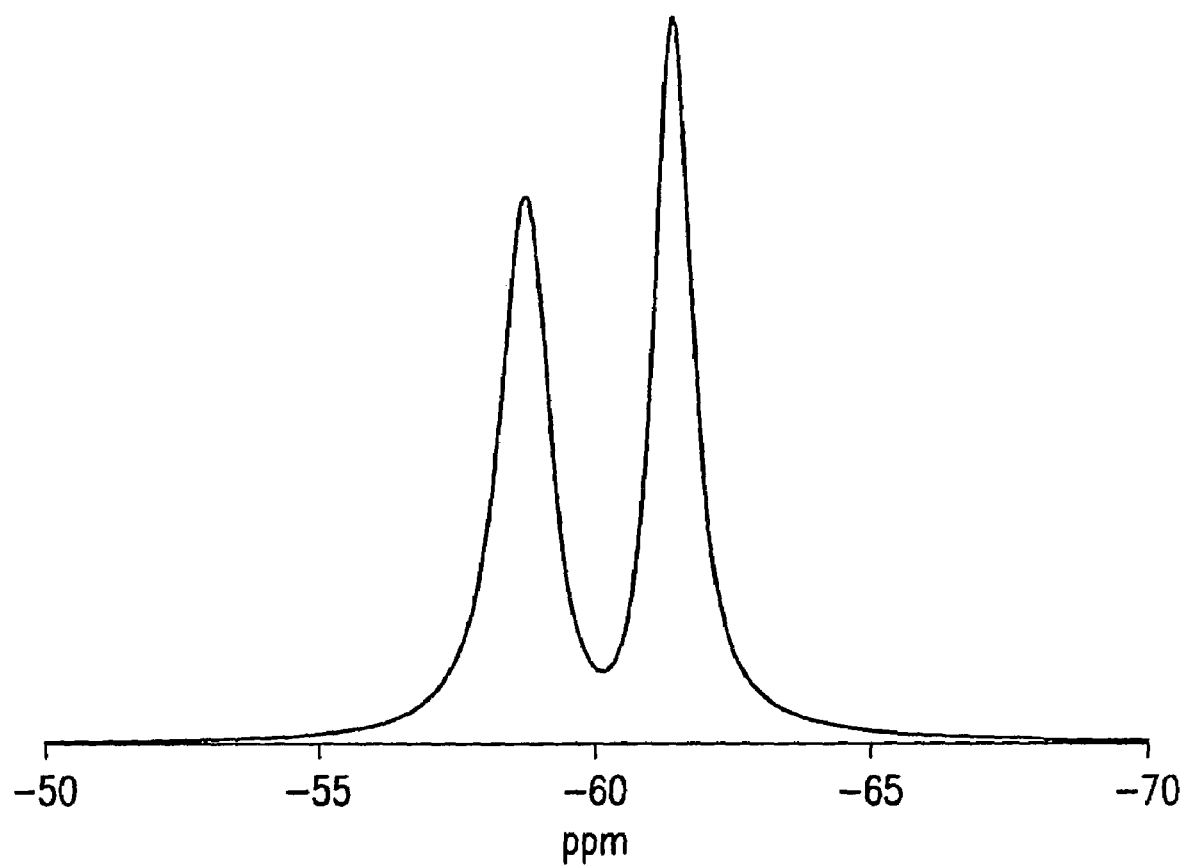
FIG. 18 displays the solid-state fluorine-19 MAS NMR spectrum of a Form B N-[1S,2S]-3-(4-chlorophenyl)-2-(3-cyanophenyl)-1-methylpropyl]-2-methyl-2-{[5-(trifluoromethyl pyridin-2-yl)oxy]propanamide sample.
Figure 19:
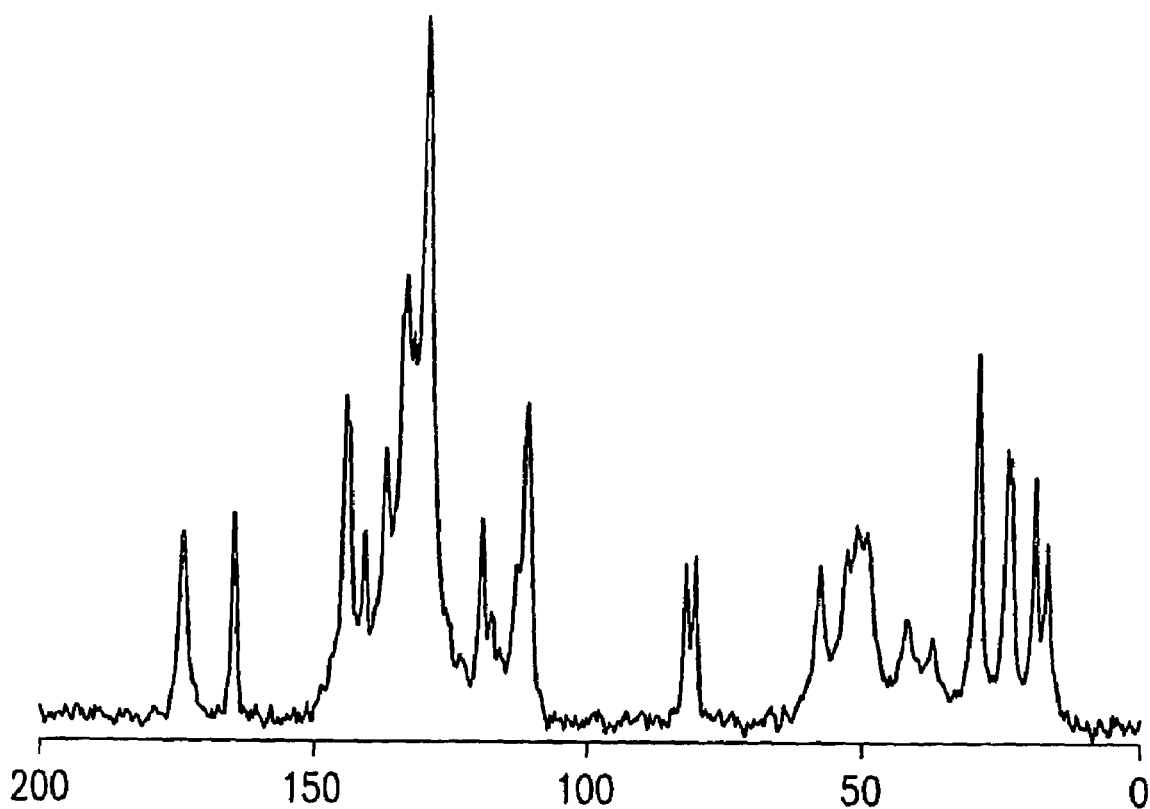
FIG. 19 displays the solid-state carbon-13 CPMAS NMR spectrum of a Form B N-[1S,2S]-3-(4-chlorophenyl)-2-(3-cyanophenyl)-1-methylpropyl]-2-methyl-2-{[5-(trifluoromethyl pyridin-2-yl)oxy]propanamide sample. Form B exhibited characteristic signals with chemical shift values of 164.6, 137.1, 111.3, 23.6, and 16.9 ppm.

The x-ray powder diffraction pattern of a Form B sample is shown in FIG. 17. It has characteristic diffraction peaks corresponding to d-spacing of 3.6, 4.3, 4.7, 4.9, 5.7 and 11.3 angstroms. FIG. 18 displays the solid-state fluorine-19 MAS NMR spectrum of a Form B sample. Form B exhibited characteristic signals with chemical shift values of −58.7 and −61.4 ppm. FIG. 19 displays the solid-state carbon-13 CPMAS NMR spectrum of a Form B sample. Form B exhibited characteristic signals with chemical shift values of 164.6, 137.1, 111.3, 23.6, and 16.9 ppm.

Figure 20:
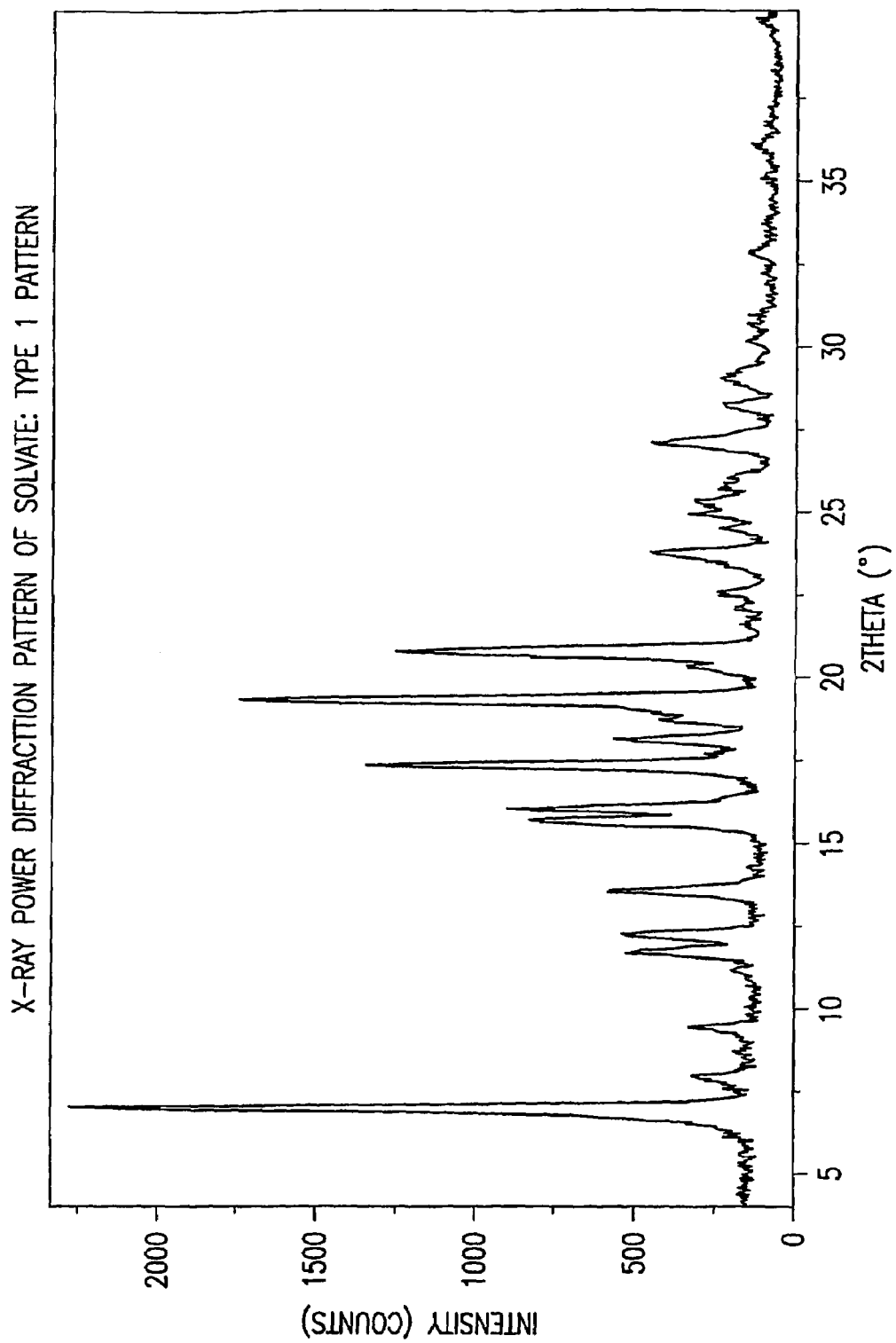
FIG. 20 shows the X-ray powder diffraction pattern of a Type 1 crystalline solvate of N-[1S,2S]-3-(4-chlorophenyl)-2-(3-cyanophenyl)-1-methylpropyl]-2-methyl-2-{[5-(trifluoromethyl pyridin-2-yl)oxy]propanamide, generated on a Philips Analytical X'Pert PRO X-ray Diffraction System with PW3040/60 console using PW33373/00 ceramic CU LEF X-ray tube K-ALPHa radiation as the source, having characteristic diffraction peaks corresponding to d-spacing of 3.3, 4.3, 4.6, 5.1 and 12.6 angstroms.
Figure 21:
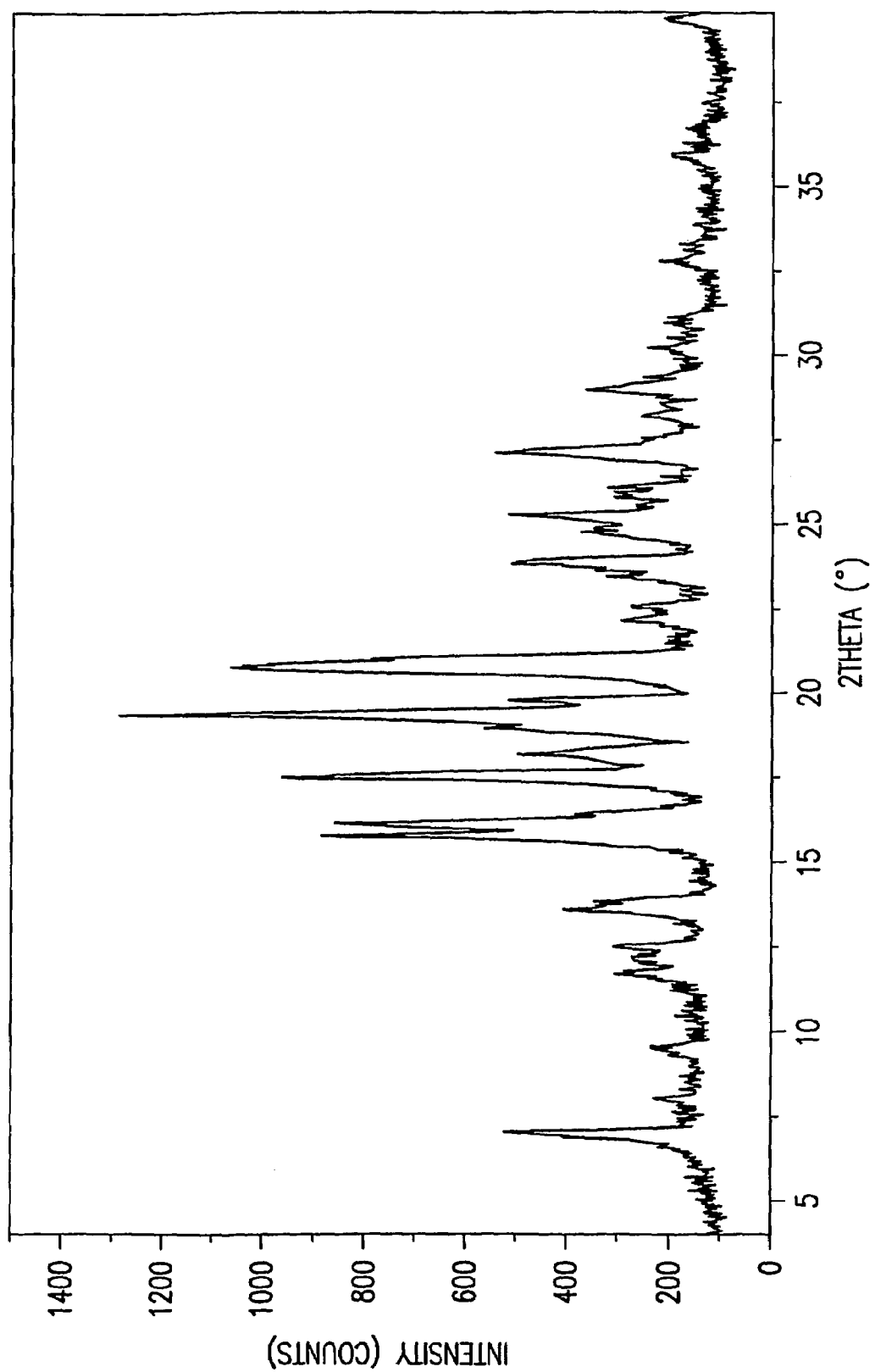
FIG. 21 shows the X-ray powder diffraction pattern of a Type 2 crystalline solvate of N-[1S,2S]-3-(4-chlorophenyl)-2-(3-cyanophenyl)-1-methylpropyl]-2-methyl-2-{[5-(trifluoromethyl pyridin-2-yl)oxy]propanamide, generated on a Philips Analytical X'Pert PRO X-ray Diffraction System with PW3040/60 console using PW33373/00 ceramic CU LEF X-ray tube K-ALPHa radiation as the source, §5 having characteristic diffraction peaks corresponding to d-spacing of 4.3, 4.6, 5.1, 5.6 and 12.6 angstroms.
Figure 22:
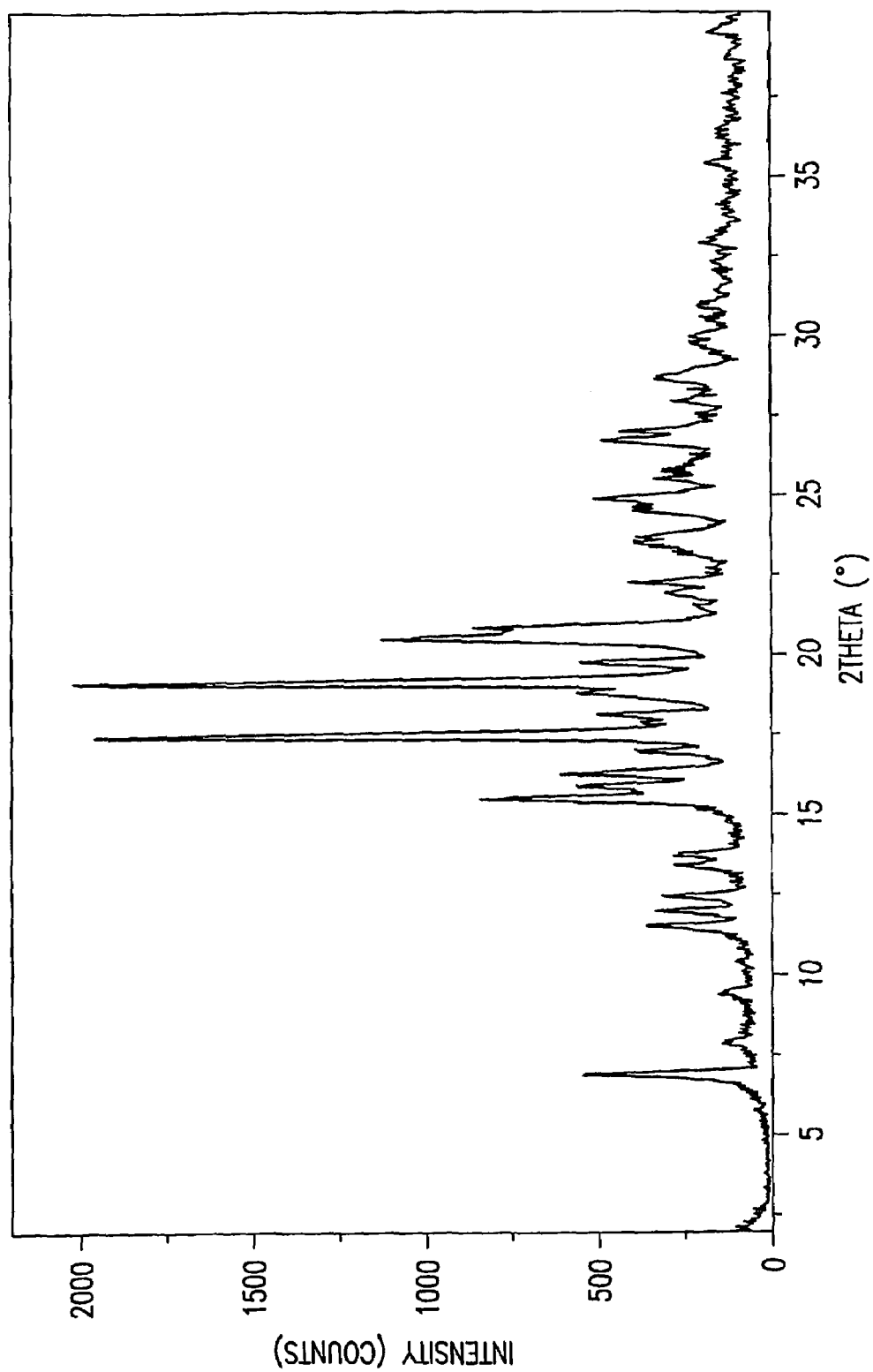
FIG. 22 shows the X-ray powder diffraction pattern of a Type 3 crystalline solvate of N-[1S,2S]-3-(4-chlorophenyl)-2-(3-cyanophenyl)-1-methylpropyl]-2-methyl-2-{[5-(trifluoromethyl pyridin-2-yl)oxy]propanamide, generated on a Philips Analytical X'Pert PRO X-ray Diffraction System with PW3040/60 console using PW33373/00 ceramic CU LEF X-ray tube K-ALPHa radiation as the source, having characteristic diffraction peaks corresponding to d-spacing of 4.3, 4.6, 5.1, 5.7 and 12.7 angstroms.
Figure 23:
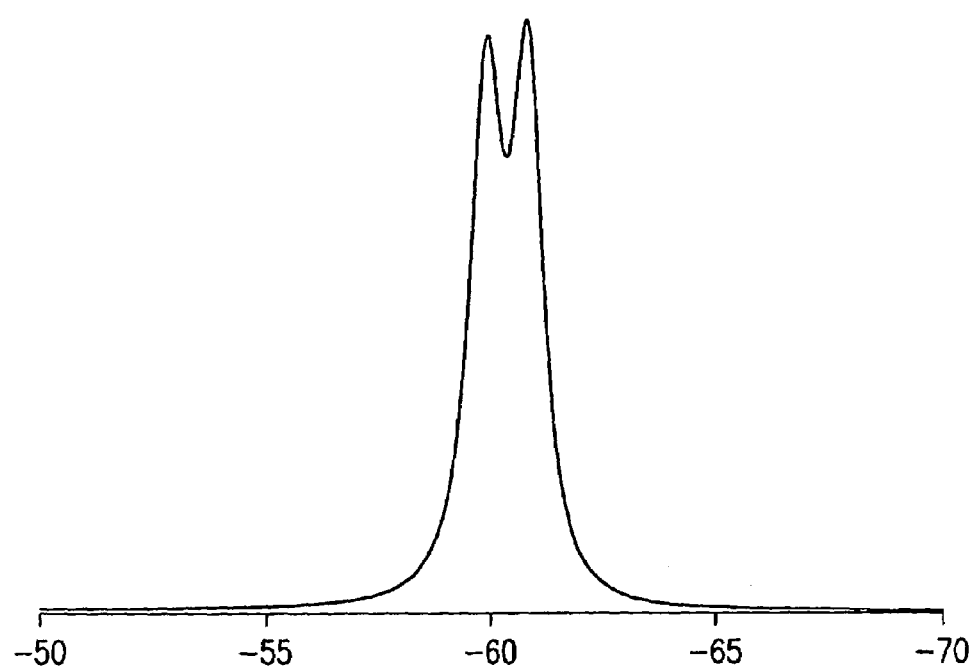
FIG. 23 displays the solid-state fluorine-19 MAS NMR spectrum of a type I crystalline solvate sample of N-[1S,2S]-3-(4-chlorophenyl)-2-(3-cyanophenyl)-1-methylpropyl]-2-methyl-2-{[5-(trifluoromethyl pyridin-2-yl)oxy]propanamide. Type 1 solvate exhibited characteristic signals with chemical shift values of –59.9, and –60.8 ppm.
Figure 24:
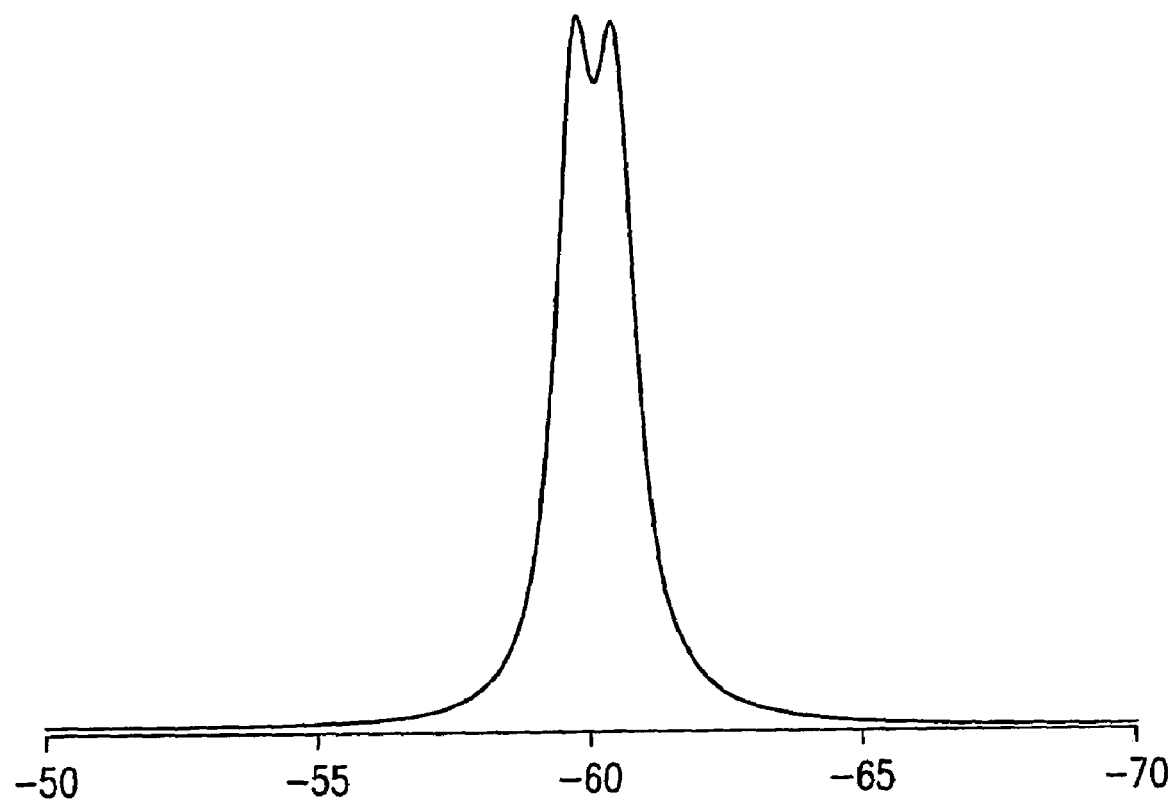
FIG. 24 displays the solid-state fluorine-19 MAS NMR spectrum of a type 2 crystalline solvate sample of N-[1S,2S]-3-(4-chlorophenyl)-2-(3-cyanophenyl)-1-methylpropyl]-2-methyl-2-{[5-(trifluoromethyl pyridin-2-yl)oxy]propanamide. Type 2 solvate exhibited characteristic signals with chemical shift values of –59.8, and –60.5 ppm.
Figure 25:
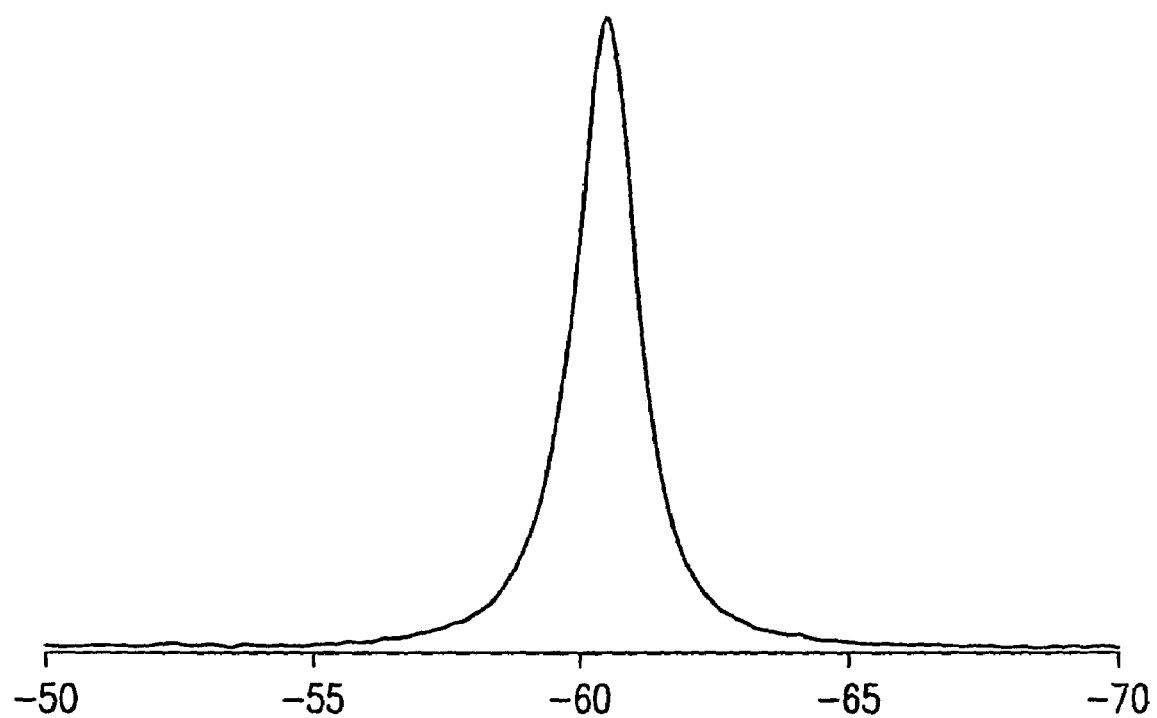
FIG. 25 displays the solid-state fluorine-19 MAS NMR spectrum of a type 3 crystalline solvate sample of N-[1S,2S]-3-(4-chlorophenyl)-2-(3-cyanophenyl)-1-methylpropyl]-2-methyl-2-{[5-(trifluoromethyl pyridin-2-yl)oxy]propanamide. Type 3 solvate exhibited characteristic signals with chemical shift values of –60.5 ppm.
Figure 26:
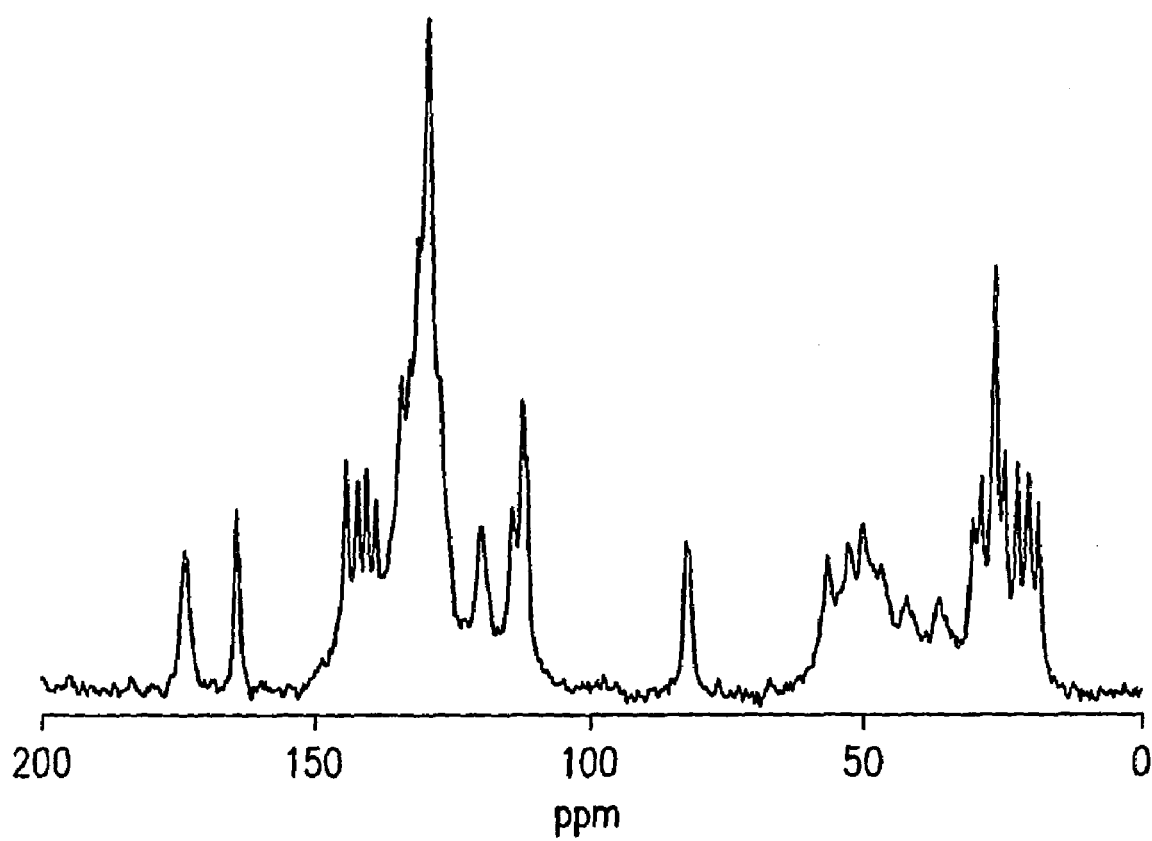
FIG. 26 displays the solid-state carbon-13 CPMAS NMR spectrum of a type 1 crystalline solvate sample of N-[1S,2S]-3-(4-chlorophenyl)-2-(3-cyanophenyl)-1-methylpropyl]-2-methyl-2-{[5-(trifluoromethyl pyridin-2-yl)oxy]propanamide. Type 1 solvate exhibited characteristic signals with chemical shift values of 164.1, 142.3, 112.5, 26.6, and 18.6 ppm.
Figure 27:
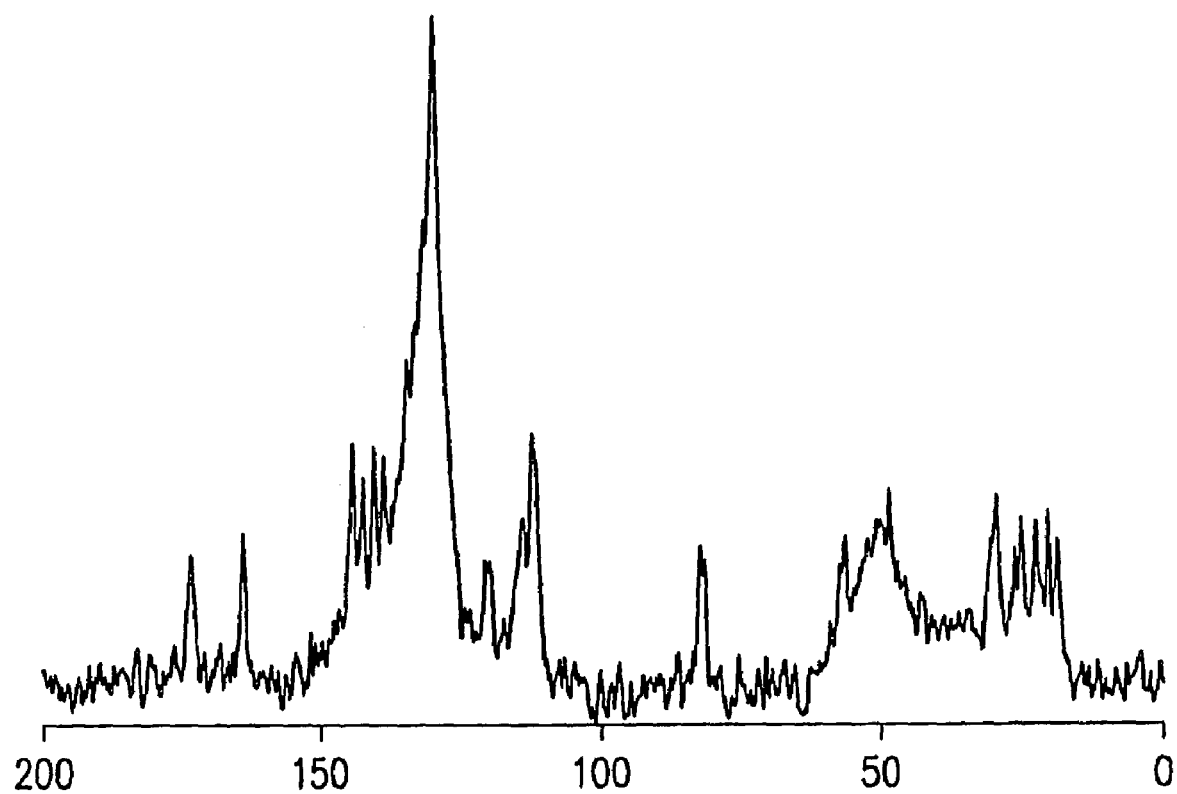
FIG. 27 displays the solid-state carbon-13 CPMAS NMR spectrum of a type 2 crystalline solvate sample of N-[1S,2S]-3-(4-chlorophenyl)-2-(3-cyanophenyl)-1-methylpropyl]-2-methyl-2-{[5-(trifluoromethyl pyridin-2-yl)oxy]propanamide. Type 2 solvate exhibited signals with similar chemical shift values to Type 1 solvate in addition to the characteristic signal with chemical shift value of 48.7 ppm.
Figure 28:
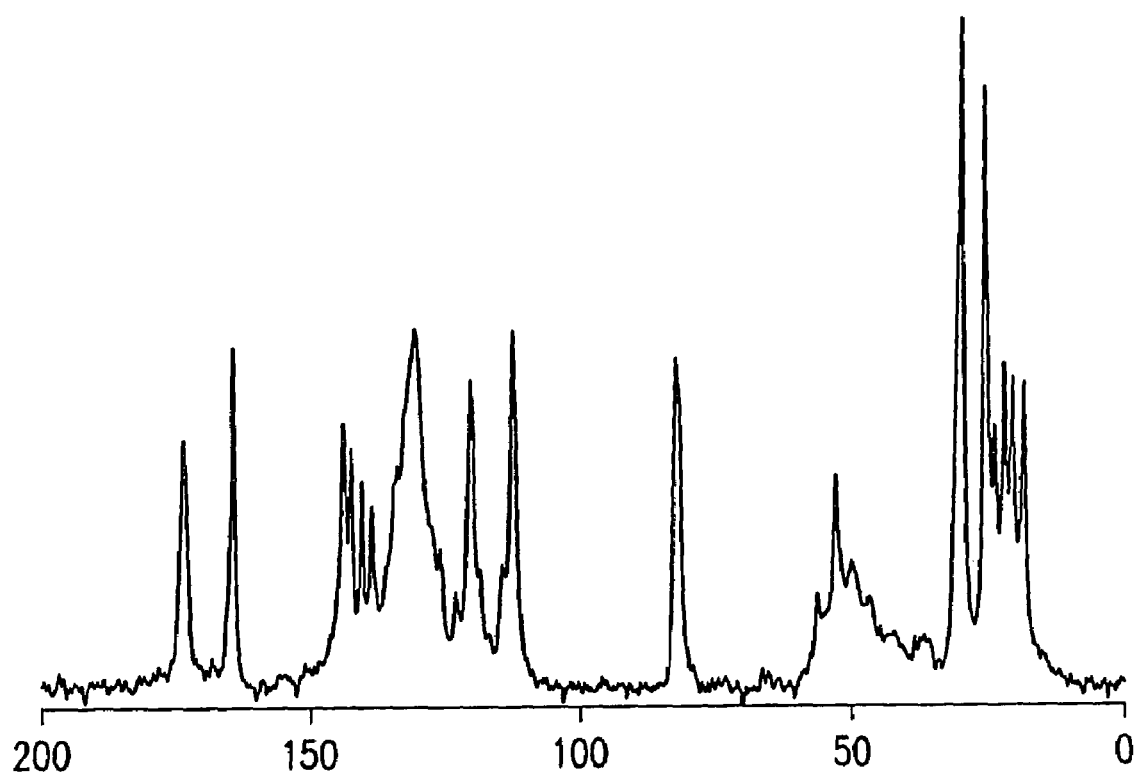
FIG. 28 displays the solid-state carbon-13 CPMAS NMR spectrum of a type 3 crystalline solvate sample of N-[1S,2S]-3-(4-chlorophenyl)-2-(3-cyanophenyl)-1-methylpropyl]-2-methyl-2-{[5-(trifluoromethyl pyridin-2-yl)oxy]propanamide. Type 3 solvate exhibited signals with similar chemical shift values to Type 1 solvate in addition to the characteristic signals with chemical shift values of 143.6, 140.3, 25.6, 29.7, 24.1, and 20.9 ppm.

Still further, N-[1S,2S]-3-(4-chlorophenyl)-2-(3-cyanophenyl)-1-methylpropyl]-2-methyl-2-{[5-(trifluoromethyl pyridin-2-yl)oxy]propanamide can form solvates with a variety of solvent systems: such as iPAc-hexanes, iPAc-cyclohexane, iPAc-methylcyclohexane, iPAc-n-hexane, iPAc-n-heptane, trifluorotoluene-pentane-methylcylcohexane, MTBE-hexanes, toluene-hexanes, toluene-iso-octane and iPAc-iso-octane. These solvates display similar X-ray powder diffraction patterns. FIG. 20 (type 1 pattern), FIG. 21 (type 2 pattern) and FIG. 22 (type 3 pattern) are three representative patterns. Type 1 pattern has characteristic diffraction peaks corresponding to d-spacing of 3.3, 4.3, 4.6, 5.1 and 12.6 angstroms. Type 2 pattern has characteristic diffraction peaks corresponding to d-spacing of 4.3, 4.6, 5.1, 5.6 and 12.6 angstroms. And type 3 pattern has characteristic diffraction peaks corresponding to d-spacing of 4.3, 4.6, 5.1, 5.7 and 12.7 angstroms. FIG. 23 displays the solid-state fluorine-19 MAS NMR spectrum of a type 1 solvate sample. Type 1 solvate exhibited characteristic signals with chemical shift values of −59.9, and −60.8 ppm. FIG. 24 displays the solid-state fluorine-19 MAS NMR spectrum of a type 2 solvate sample. Type 2 solvate exhibited characteristic signals with chemical shift values of −59.8, and −60.5 ppm. FIG. 25 displays the solid-state fluorine-19 MAS NMR spectrum of a type 3 solvate sample. Type 3 solvate exhibited characteristic signals with chemical shift values of −60.5 ppm FIG. 26 displays the solid-state carbon-13 CPMAS NMR spectrum of a type 1 solvate sample. Type 1 solvate exhibited characteristic signals with chemical shift values of 164.1, 142.3, 112.5, 26.6, and 18.6 ppm. FIG. 27 displays the solid-state carbon-13 CPMAS NMR spectrum of a type 2 solvate sample. Type 2 solvate exhibited signals with similar chemical shift values to Type 1 solvate in addition to the characteristic signal with chemical shift value of 48.7 ppm. FIG. 28 displays the solid-state carbon-13 CPMAS NMR spectrum of a type 3 solvate sample. Type 3 solvate exhibited signals with similar chemical shift values to Type 1 solvate in addition to the characteristic signals with chemical shift values of 143.6, 140.3, 25.6, 29.7, 24.1, and 20.9 ppm.

An exemplary synthetic scheme showing the formation of a specific enamide II (Compound 5 below) by the palladium catalyzed coupling of a specific primary amide IV (Compound 4 below) with a compound of structural formula II (Compound 3 below), and two routes for the subsequent stereospecific reduction of the enamide II (Compounds 5 and 6 below) to the corresponding amide I (Compounds 7 and 8, respectively below). Compound 7 is converted to pharmaceutically useful Compound 8, N-[1S,2S]-3-(4-chlorophenyl)-2-(3-cyanophenyl)-1-methylpropyl]-2-methyl-2-{[5-(trifluoromethyl pyridin-2-yl)oxy]propanamide.

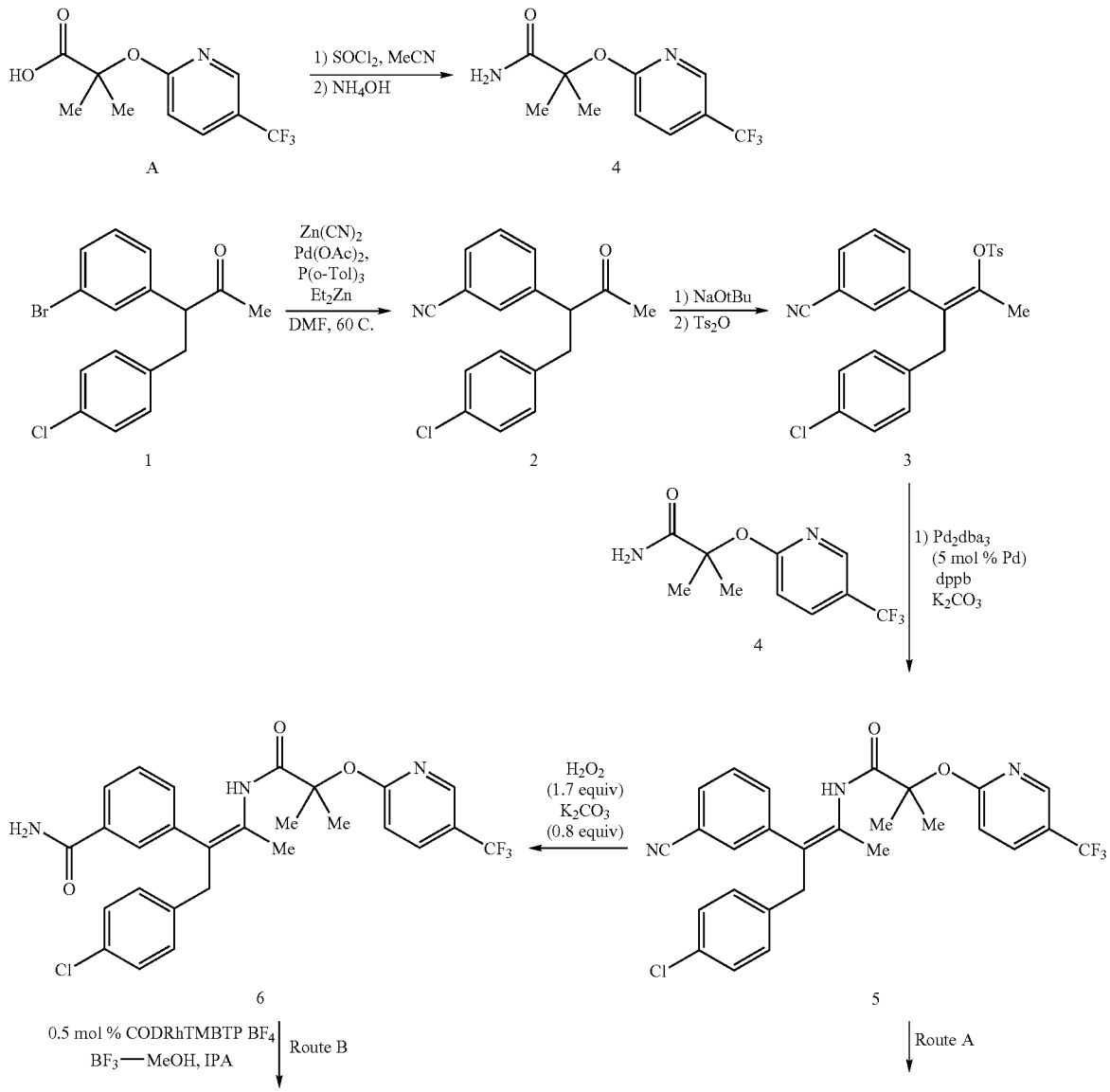

Reaction Scheme I:

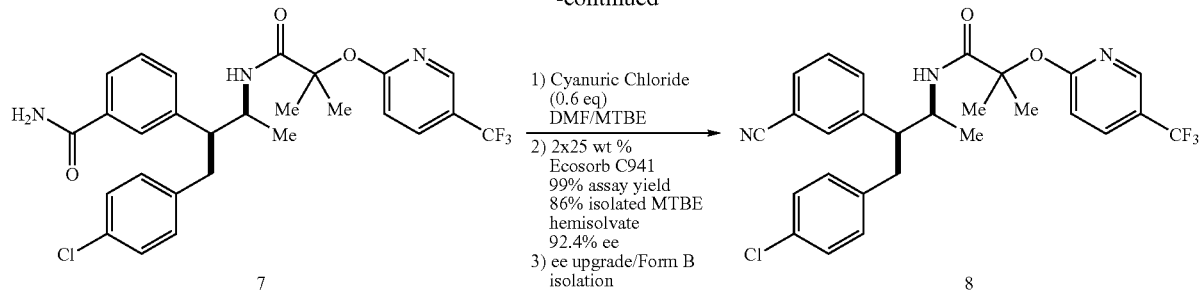

The starting amide, Compound 4, may be prepared from the corresponding acid, Compound A. Acid Compound A may be made as described in WO 03/077847, or by other means known to the art. The acid, Compound A, may be converted to the amide, Compound 4, by procedures known to those of ordinary skill in the art. One such procedure is treatment with thionyl chloride in an appropriate solvent, in one embodiment an aprotic solvent such as acetonitrile to form the acid chloride followed by treatment with ammonia to form the amide.

The vinyl tosylate (3) may be formed from the corresponding ketone (2) by treatment with a base, such as any alkoxide base, particularly sodium t-butoxide and p-toluenesulfonyl anhydride in a solvent, particularly N,N-dimethylacetamide, N-methylpyrrolidinone or DMF. In the particular example illustrated in Scheme I, the benzonitrile-substituted ketone (2) is itself formed from the corresponding phenylbromide (1) by treatment with zinc cyanide in the presence of a palladium catalyst and a reducing agent such as diethyl zinc in an appropriate polar aprotic solvent such as DMF or DMAC. Other $R^1$ and $R^2$ substituents on the phenyl groups of the ketone are synthesized according to procedures known to those of ordinary skill in the art, including the use of potassium hexacyano ferrate (U) as disclosed in J. Organometallic Chem. 689 (2004), pp. 4576-4583.

The vinyl tosylate (3) is treated with amide (4) in the presence of base, in particular an inorganic base such as potassium carbonate and a palladium catalyst, particularly tris(dibenzylideneacetone) dipalladium(0), bis(dibenzylideneacetone)palladium(0) and an appropriate phosphine ligand, particularly a diphosphine ligand, such as 1,4-bis(diphenylphosphino)butane or 1,1'-bis(diisopropylphosphino) ferrocene in an appropriate solvent, particularly a tertiary alcohol such as t-amyl alcohol, or an arene such as toluene or a mixture of a tertiary alcohol and an arene such as a mixture of tert-amyl alcohol and toluene to form the cyano enamide (5).

The cyanoenamide (5) may be either directly stereospecifically reduced to the desired cyano amide (8), (Route A) or it may be first converted to the amide-enamide (6), stereospecifically reduced to the corresponding chiral amide (7), and then converted to the cyano-amide (8) (Route B).

In Route A, the cyanoenamide (5) is treated with hydrogen in the presence of a chiral catalyst to form the desired cyano-amide product (8). The cyanoenamide is dissolved in an appropriate solvent such as methanol, ethanol, isopropanol, trifluoroethanol, THF, isopropyl acetate, ethyl acetate, toluene, methylene chloride, dichloroethane, DMA, DMF, water, or a combination of these solvents, particularly methanol, THF or trichloroethane, and most particularly dichloroethane. The reaction is generally carried out at a concentration of about 5 to 200 g/L solvent, particularly 10 to 100 g/L solvent or 60 to 100 g/L. The hydrogen gas is generally employed at a pressure between 1 and 100 atmospheres, particularly between 20 to 80 atmospheres, more particularly 30 and 60 atmospheres. An additive, such as acetic acid, tetrafluoroboric acid, trifluoroacetic acid, toluene sulfonic acid, methanesulfonic acid, phosphoric acid, citric acid or a Lewis acid such as: $BF_3$.solvent, $B(OMe)_3$, $B(O-iPr)_3$, $LiBF_4$, LiOTf, $NaPF_6$, $Cs_2CO_3$, $MgSO_4$, $Sc(O-iPr)_3$, $Cu(OTf)_2$, $[[Cu(OTf)]_2$.benzene], $Cu(COCF_3)_2.H_2O$, $Zn(OTf)_3$, $Sc(OTf)_3$, $La(OTf)_3$, $Mg(OTf)_2$, $LiBF_4(DME)_3$, $K(BPh_4)$, and $BEt_3$, particularly $BF_3$.MeOH, may be optionally employed in the reaction mixture. In one example, no additive is employed. The additive may be favorably employed between 0 and 200 mol %, particularly between 0 and 40 mol %; preferably the additive is not present (0 mol %). The chiral catalyst may be a preformed catalyst complex, in particular, (R,S)-(di-t-butylphosphino)ferrocenyl-ethyldi-3,5-dimethylphenylphosphine (COD)RhBF4, or the chiral catalyst complex may be formed in situ metal precursor, such as (NBD)2RhBF4, a ligand such as (R,S)-(di-t-butylphosphino)ferrocenyl-ethyldi-3,5-dimethylphenylphosphine, (−)-TMBTP, or (R)-Hexaphemp and optionally a catalyst activator, such as tetrafluoroboric acid. The catalyst to substrate molar ratio is from 10 to 500, particularly 20 to 100, most particularly 30 to 50.

In Route B, the cyano-enamide (5) is converted to the corresponding amide-enamide (6), by methods well known to those of ordinary skill in the art. In particular, the cyano-enamide (5) is treated with aqueous hydrogen peroxide in the presence of a base, particularly an inorganic base such as potassium carbonate in an appropriate solvent such as DMSO. The resulting amide-enamide (6) is treated with hydrogen in the presence of a chiral catalyst to form the desired chiral amide product (7). The amide-enamide is dissolved in an appropriate solvent such as methanol, ethanol, isopropanol, trifluoroethanol, THF, isopropyl acetate, ethyl acetate, toluene, methylene chloride, dichloroethane, DMA, DMF, water, or a combination of these solvents, particularly from methanol, ethanol, isopropanol, and trifluoroethanol, and most particularly isopropanol. The reaction is generally carried out at a concentration of about 5 to 300 g amide-enamide (6) per liter solvent. In one embodiment, the reaction is carried out in 5 to 200 g amide-enamide (6) per liter solvent, particularly 10 to 100 g/L solvent or 60 to 100 g/L. In another embodiment, the reaction is carried out in 10 to 250 g/L solvent or 150 to 250 g/L. The hydrogen gas is generally employed at a pressure between 1 and 100 atmospheres, in one embodiment between 5 and 40 atmospheres, in another embodiment between 20 and 40 atmospheres. An additive, such as acetic acid, tetrafluoroboric acid, trifluoroacetic acid, toluene sulfonic acid, methanesulfonic acid, phosphoric acid, citric acid or a Lewis acid such as: $BF_3$.solvent, $B(OMe)_3$, $B(O-iPr)_3$, $LiBF_4$, LiOTf, $NaPF_6$, $Cs_2CO_3$, $MgSO_4$, $Sc(O-iPr)_3$, $Cu(OTf)_2$, $[[Cu(OTf)]_2$.benzene], $Cu(COCF_3)_2.H_2O$, $Zn(OTf)_3$, $Sc(OTf)_3$, $La(OTf)_3$, $Mg(OTf)_2$, $LiBF_4(DME)_3$, $K(BPh_4)$, and $BEt_3$, particularly tetrafluoroboric acid, trifluororacetic acid and BF$_3$.MeOH, more particularly BF$_3$.MeOH, may be optionally employed in the reaction mixture. The additive may be favorably employed between 0 and 200 mol %, particularly between 3 and 40 mol %, preferably between 20-40 mol %. The chiral catalyst may be a preformed catalyst complex, in particular (−)-TMBTP(COD)RhBF$_4$, or the chiral catalyst complex may be formed in situ metal precursor, such as is (COD)$_2$RhBF$_4$ or (NBD)$_2$RhBF$_4$ a ligand such as (R,S)-(di-t-butylphosphino)ferrocenyl-ethyldi-o-tolylphosphine, (R,S)-(diphenylphosphino)ferrocenyl-ethyldi-t-butylphosphine, (−)-TMBTP, (R)-Hexahemp, and (R)-xyl-BINAP, particularly tetrafluoroboric acid, and a catalyst activator, such as tetrafluoroboric acid. The catalyst to substrate molar ratio is from 10 to 5000. In one embodiment, the catalyst to substrate molar ratio is from 200 to 2000, particularly 300 to 1000. In another embodiment, the catalyst to substrate ration is from 200 to 500, most particularly 30 to 50.

Representative experimental procedures utilizing the novel process are detailed below. These procedures are exemplary only and should not be construed as being limitations on the novel process of this invention.

Abbreviations: Ac: acetyl; Acac: acetoacetyl; (COD): cyclooctadiene; DARCO KB-B: tradename for carbon resin; dipf: bis-1,1'-diisopropylphosphino ferrocene; DMAC: dimethylacetamide; DMA: N,N-dimethylacetamide; DME: 1,2-dimethoxyethane; DMF: dimethylformamide; dppb: 1,4-diphenylphosphinobutane; ee: enantiomeric excess; in: inches; IPA: isopropyl alcohol; IPAc: isopropyl acetate; LCAP: liquid chromatography assay percent; LHMDS: lithium bis(trimethylsilyl)amide; Me: methyl; MTBE: methyl tert-butyl ether; NBD: norbornadiene; Pd$_2$ dba$_3$: bis-palladium tri(dibenzylidene acetone); RT: room temperature; SOLKA FLOC: filter aid; tBu: tertiary butyl; TEA: triethylamine; Tf: trifluoromethylsulfonyl (triflate); THF: tetrahydrofuran; TNBTP: tetramethylbisdiphenylphosphinothiophene; Ts: p-toluenesulfonyl (tosyl).

EXAMPLE 1

2-methyl-2-{[5-(trifluoromethyl)pyridin-2-yl]oxy}propanamide

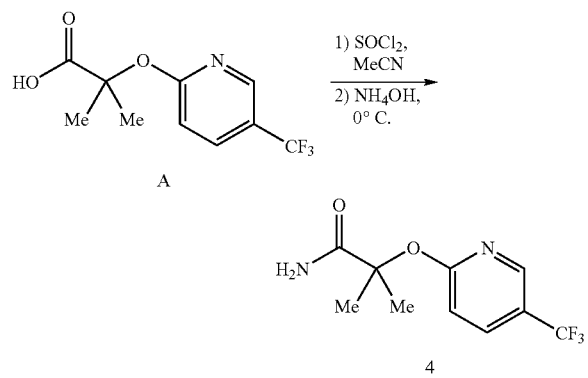

In a 12 L 3-neck separatory funnel equipped with overhead stirrer, nitrogen inlet and thermocouple, a solution of 2-methyl-2-{[5-(trifluoromethyl)pyridin-2-yl]oxy}propanoic acid (772 g) in MeCN (6.5 L) was prepared. Thionyl chloride (316 mL) was added over 30 minutes. The resulting solution was stirred at room temperature for 2 h. A separate 22 L 3-necked round bottom flask equipped with overhead stirrer, nitrogen inlet and thermocouple, was charged with 30% NH$_4$OH (aq) (5 L) and cooled to −20° C. The acid chloride solution from the separatory funnel was added to the solution of NH$_4$OH at such a rate that the internal reaction temperature was kept at −15 to −20° C. over 2 h. Once the addition was complete, the resulting slurry was warmed to room temperature and stirred for an additional 1 h. The reaction mixture was transferred to a 50 L extractor containing toluene (15 L) and water (15 L), and the layers were separated. The organic layer was washed with sat'd aq NaHCO$_3$ (5 L), and then with water (5 L). The organic layer was transferred to a 12 L four neck round bottom flask, and concentrated under vacuum at 50° C. to about 2 L volume.

Near the end of the concentration, the solid began to precipitate, and the batch was heated to 78° C. to dissolve all of the solids. Heptane (5 L) was added and the batch was allowed to slowly cool, affording a crystalline solid. The slurry was filtered, and the filter cake was washed with n-heptane (1 L). The resulting solid was dried under a stream of nitrogen to afford 626 g of the title compound (99.6 LCAP, 98.0 wt %, 81% isolated yield).

EXAMPLE 2

3-[1-(4-chlorobenzyl)-2-oxopropyl]benzonitrile

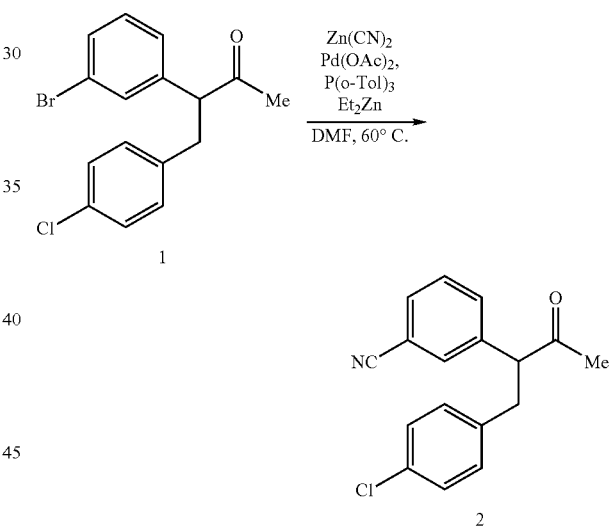

Step A: Catalyst Preparation

A 4-neck 12 L round bottom flask equipped with thermocouple, overhead stirrer, rubber septum, N$_2$ inlet, and gas adapter connected to a bubbler was charged with palladium acetate (12.8 g), tri-o-tolylphosphine (69.9 g), and dimethylformamide (2.8 L). N$_2$ was bubbled through the solution for 20 min at ambient temperature. The flask was then heated to 56° C. on a heating mantle, and the mixture was stirred at 60° C. for 20 min. A solution of diethylzinc in toluene (1.1M, 78.0 mL) was added via syringe. The resulting suspension was stirred at 56° C. for 45 min.

Step B: Cyanation Reaction

A 4-neck 12 L flask equipped with a mechanical stirrer, thermocouple, nitrogen inlet, and gas adapter connected to a bubbler was charged with 3-(3-bromophenyl)-4-(4-chlorophenyl)butan-2-one, zinc cyanide (201 g), and dimethylformamide 4.0 L. Nitrogen gas was bubbled through the suspension for 30 min at room temperature and for 1 h at 56° C. using a heating mantle. The bromoketone/Zn(CN)₂ slurry (at 56° C.) was added to the catalyst solution (at 56° C.). After the transfer was complete, the reaction mixture was stirred at 56° C. for 4.5 h under N₂. The resulting suspension was cooled in an ice bath, and 30% aqueous ammonium hydroxide (971 mL) was added over 5 min, keeping the temperature below 30° C. The suspension was warmed to room temperature, stirred for 60 min, and then filtered through a pad of SOLKA FLOC eluting with toluene (5 L). The filtrate was added into an extractor containing 20% aqueous ammonium hydroxide (6.9 L) and 5 L of toluene. The biphasic mixture was stirred at room temperature for 15 min and then separated. The organic layer was washed with 7 L of brine (1:1 saturated NaCl:Water), then 7 L of water. The organic phase was transferred to a 12 L 4 neck flask equipped with an overhead stirrer, thermocouple, mechanical stirrer, and connected to a batch concentrator. The batch was concentrated under vacuum at 15-38° C. to a volume of 1.5 L, and then heptane (850 mL) was added.

A sample was taken at this point, and crystallized in a vial. This seed sample was recharged back to the flask which created a seed bed for the crystallization. Once a seed bed formed (~30 minutes) 6.5 L of heptane was added over 40 minutes, and the batch was cooled to 0° C. The batch was filtered, and the filter cake was washed with heptane (2 L). The resulting solid was dried under a stream of nitrogen to provide 755 g of the title compound (98.9 area %, >99 wt %, 93% isolated yield).

XRPD: FIG. 1 shows the X-ray powder diffraction pattern (XRPD) of the title compound generated on a Philips Analytical X'Pert PRO X-ray Diffraction System with PW3040/60 console using a PW3373/00 ceramic Cu LEF X-ray tube K-Alpha radiation as the source. The title compound exhibited characteristic diffraction peaks corresponding to d-spacings of 7.4, 4.6, 4.0, 3.8, 3.5, 3.4 angstroms.

Figure 2:
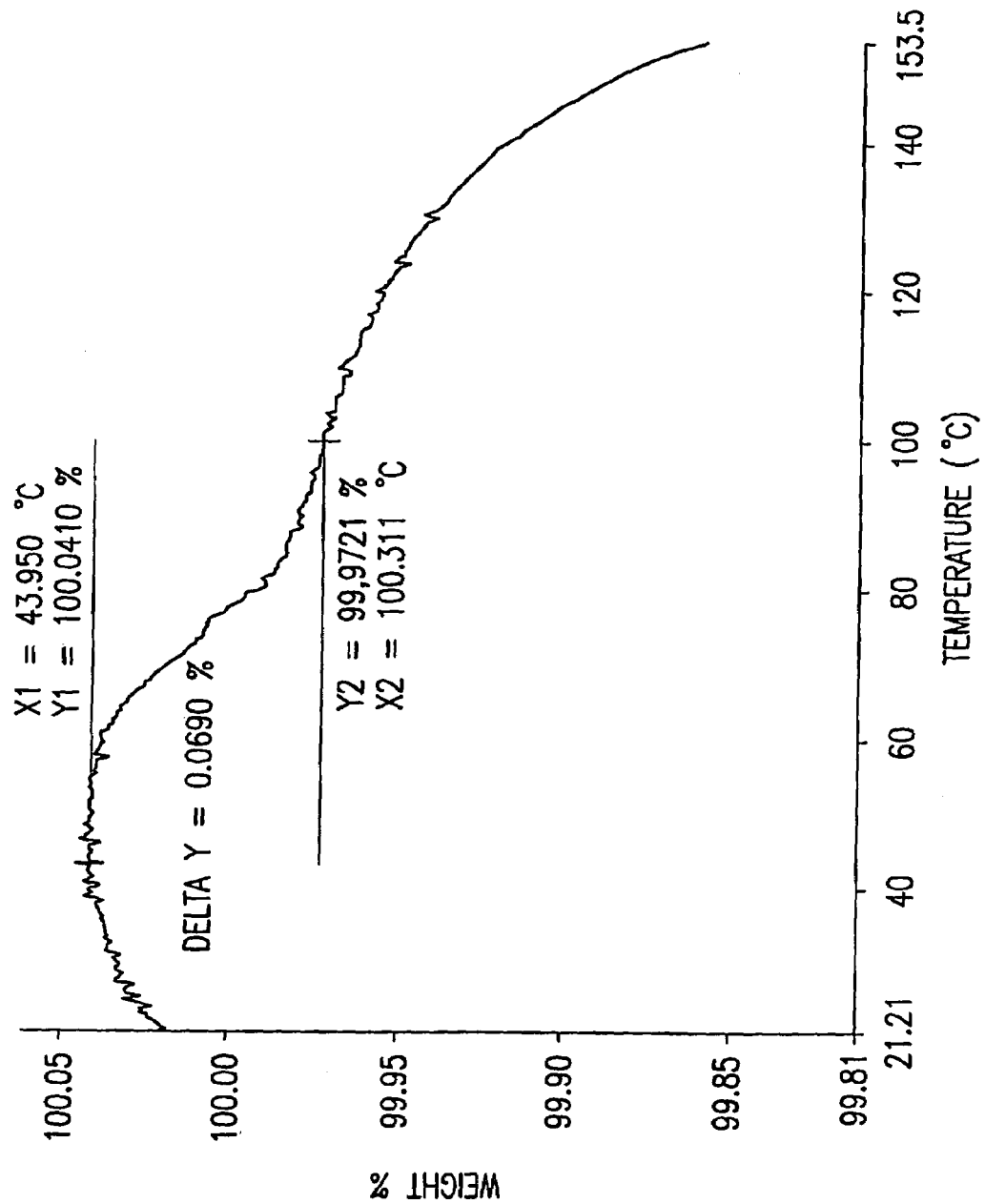
FIG. 2 shows the thermogravimetry (TG) data 3-[1-(4-chlorobenzyl)-2-oxopropyl]benzonitrile (EXAMPLE 2) obtained at a heating rate of 10° C./min under nitrogen atmosphere.
Figure 3:
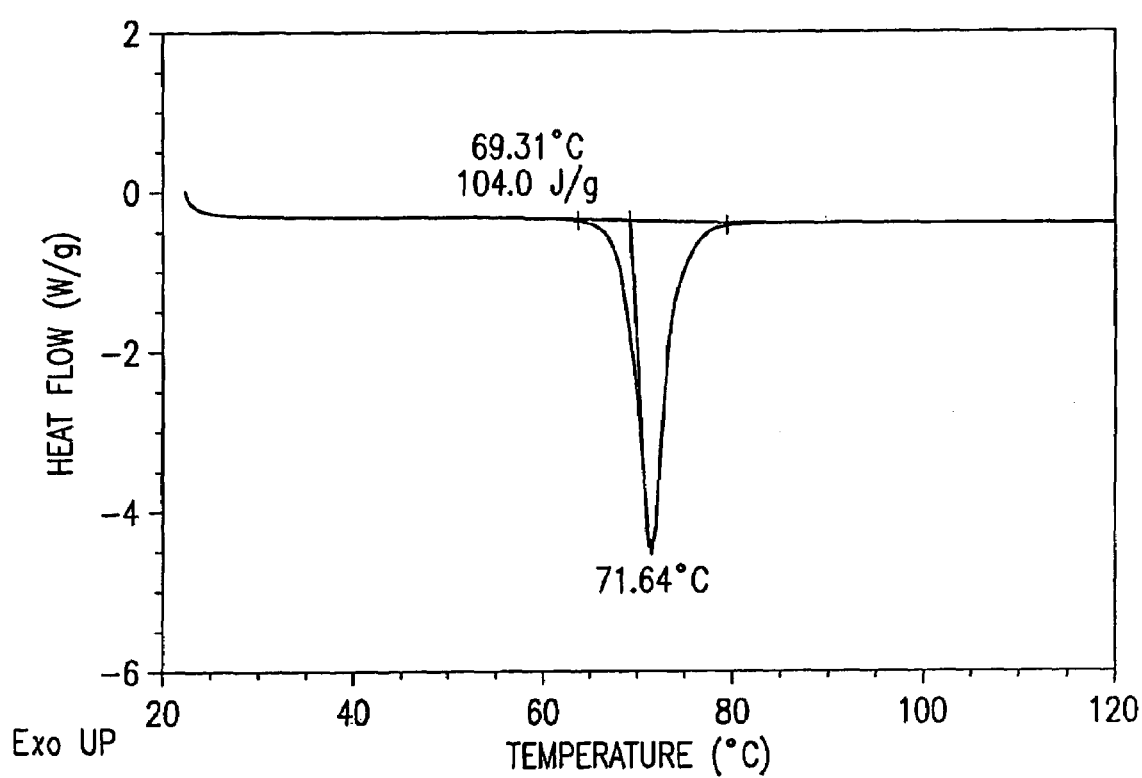
FIG. 3 shows differential scanning calorimetry (DSC) data collected at a heating rate of 10° C./min, under nitrogen atmosphere in a hermetic pan for 3-[1-(4-chlorobenzyl)-2-oxopropyl]benzonitrile (EXAMPLE 2), displaying a melting endotherm with an extrapolated onset temperature of 69.3° C., a peak temperature of 71.6° C., and an enthalpy change of 104 J/g.

Thermal Analysis (TG and DSC): The thermogravimetry (TG) data of the title compound was obtained at a heating rate of 10° C./min under nitrogen atmosphere and shown in FIG. 2. A weight loss of 0.07% was observed from 44 to 100° C. Differential scanning calorimetry (DSC) data were collected at a heating rate of 10° C./min, under nitrogen atmosphere in a hermetic pan. The DSC curve of the title compound is shown in FIG. 3 and displays a melting endotherm with an extrapolated onset temperature of 69.3° C., a peak temperature of 71.6° C., and an enthalpy change of 104 J/g.

EXAMPLE 3

3-(4-chlorophenyl)-2-(3-cyanophenyl)-1-methyl-prop-1-en-1-yl 4-methylbenzenesulfonate

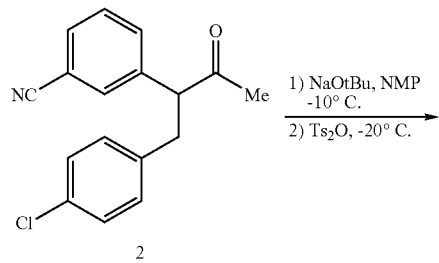

2

1) NaOtBu, NMP
   -10° C.
2) Ts₂O, -20° C.

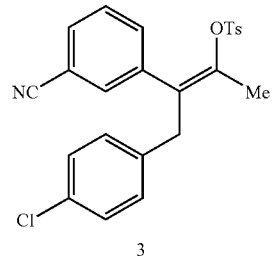

3

A 4-neck, 12 L flask equipped with a mechanical stirrer, thermocouple, and nitrogen inlet was charged N,N-dimethylacetamide (7.2 L), followed by 3[1-(4-chlorobenzyl)-2-oxopropyl]benzonitrile (Example 2, 744 g), then bubbled with nitrogen through the reaction mixture for 30 minutes at room temperature.

The mixture was cooled to −10° C., and NaOtBu (265 g) was added as a solid in one portion with stirring (tmax=−2° C.). The solution was allowed to stir with cooling until the exotherm stopped and the temperature began to drop (approx. 2 minutes). The cooling bath was removed, and the reaction was warmed to room temperature, then stirred for 1 hour. The mixture was cooled to −20° C. and p-toluene sulfonic anhydride (Ts₂O, 893 g) was added as a solid in two portions with stirring, keeping the temperature below −5° C. (tmax=−8° C.). The mixture was allowed to cool back to −10° C. and stirred for 1 hour. The reaction was quenched with 1 M NaHCO₃ (1.9 L), and transferred to a 50 L extractor containing 15 L IPAc and 13 L water. The layers were separated and the organic layer was washed twice with 7.5 L water. The organic layer was concentrated under slight vacuum (25 in Hg) at 55° C. to ~2 L. Upon reaching the 2 L volume, the batch began to crystallize, so the vacuum was turned off and the flask was heated to 73° C. to produce a homogeneous solution. Heptane (6.6 L) was added while the mixture was allowed to slowly cool to room temperature. The resulting slurry was aged for 1 h at room temperature, then filtered. The filter cake is washed with 3 L heptane and dried under a stream of nitrogen to yield 974 g of the title compound (>99 area %, >99 wt %, 85% isolated yield).

Figure 4:
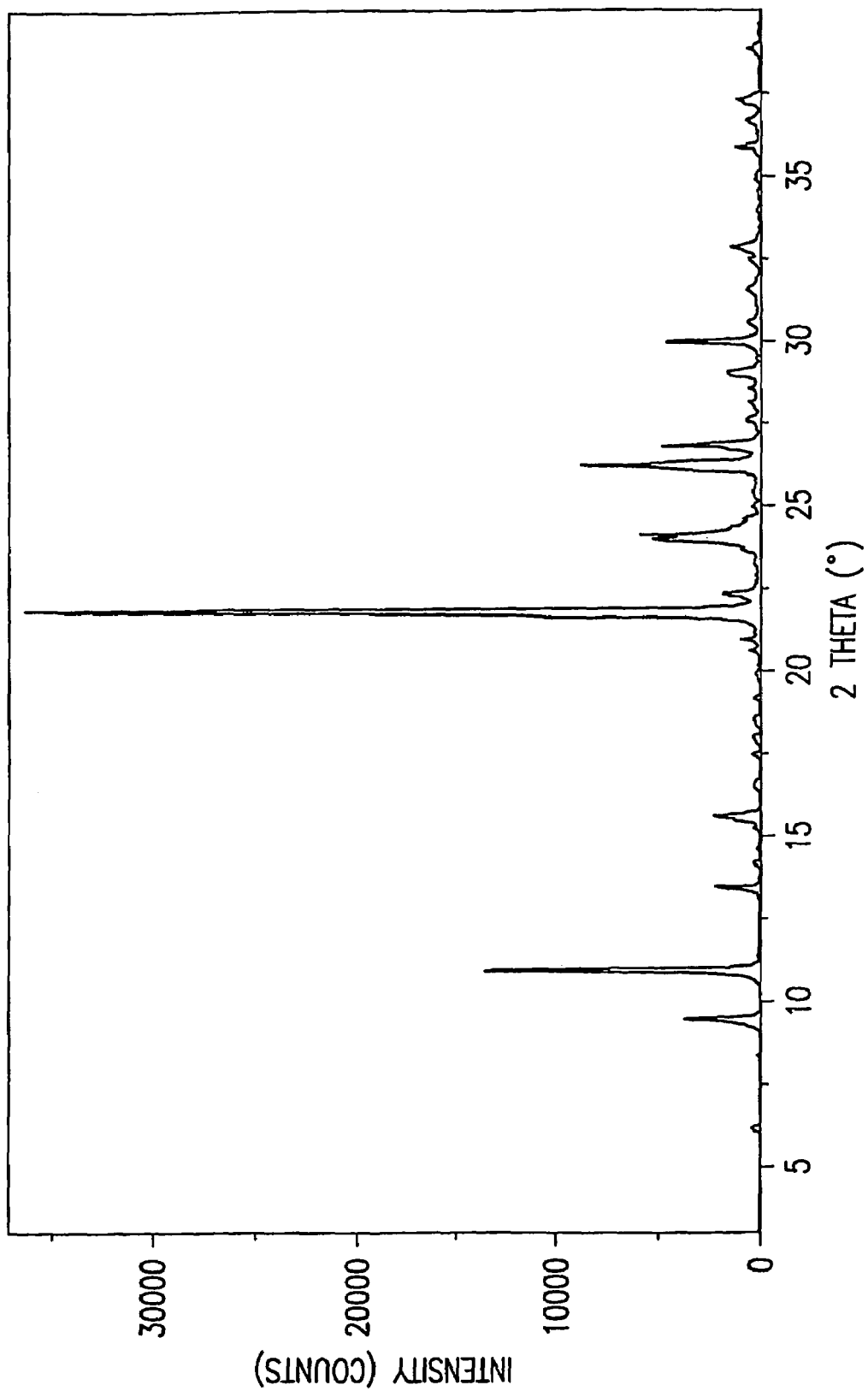
FIG. 4 shows the X-ray powder diffraction pattern of 3-(4-chlorophenyl)-2-(3-cyanophenyl)-1-methylprop-1-en-1-yl 4-methylbenzenesulfonate (EXAMPLE 3), generated on a Philips Analytical X'Pert PRO X-ray Diffraction System with PW3040/60 console using a PW3373/00 ceramic Cu LEF X-ray tube K-Alpha radiation as the source.

XRPD: FIG. 4 shows the X-ray powder diffraction pattern of the title compound generated on a Philips Analytical X'Pert PRO X-ray Diffraction System with PW3040/60 console using a PW3373/00 ceramic Cu LEF X-ray tube K-Alpha radiation as the source. The title compound exhibited characteristic diffraction peaks corresponding to d-spacings of 9.3, 8.1, 6.6, 5.7, 4.1, 3.4 angstroms.

Figure 5:
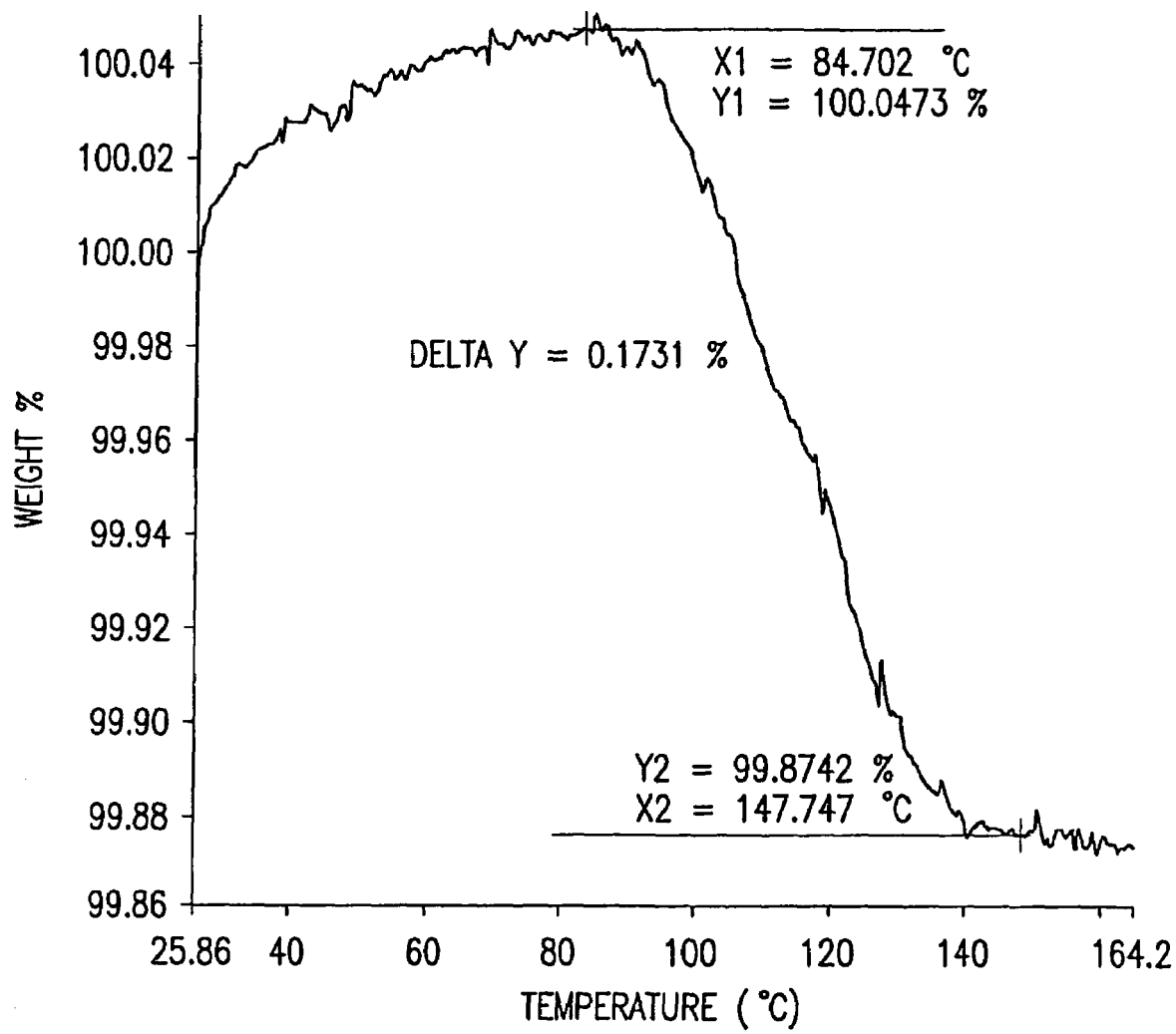
FIG. 5 shows the thermogravimetry (TG) data of 3-(4-chlorophenyl)-2-(3-cyanophenyl)-1-methylprop-1-en-1-yl 4-methylbenzenesulfonate (EXAMPLE 3) obtained at a heating rate of 10° C./min under nitrogen atmosphere and shown in FIG. 17. A weight loss of 0.17% was observed from 85 to 148° C.
Figure 6:
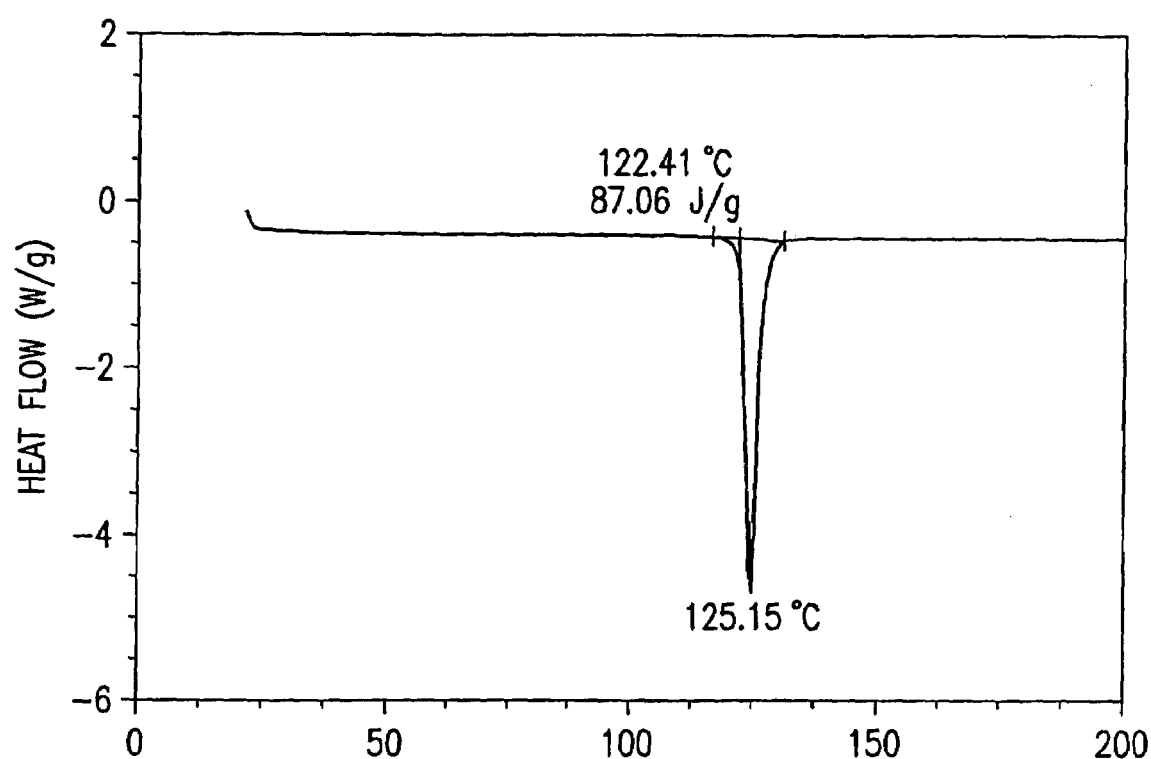
FIG. 6 shows the differential scanning calorimetry (DSC) data collected at a heating rate of 10° C./min, under nitrogen atmosphere in a hermetic pan for 3-(4-chlorophenyl)-2-(3-cyanophenyl)-1-methylprop-1-en-1-yl 4-methylbenzenesulfonate (EXAMPLE 3), displaying a melting endotherm with an extrapolated onset temperature of 122.4° C., a peak temperature of 125.2° C., and an enthalpy change of 87 J/g.

Thermal Analysis (TG and DSC): The thermogravimetry (TG) data of the title compound was obtained at a heating rate of 10° C./min under nitrogen atmosphere and shown in FIG. 5. A weight loss of 0.17% was observed from 85 to 148° C. Differential scanning calorimetry (DSC) data were collected at a heating rate of 10° C./min, under nitrogen atmosphere in a hermetic pan. The DSC curve of the title compound is shown in FIG. 6 and displays a melting endotherm with an extrapolated onset temperature of 122.4° C., a peak temperature of 125.2° C., and an enthalpy change of 87 J/g.

EXAMPLE 4

N-[(1Z)-3-(4-chlorophenyl)-2-(3-cyanophenyl)-1-methylprop-1-en-1-yl]-2-methyl-2-{[5-(trifluoromethyl)pyridin-2-yl]oxy}propanamide Preparation 1

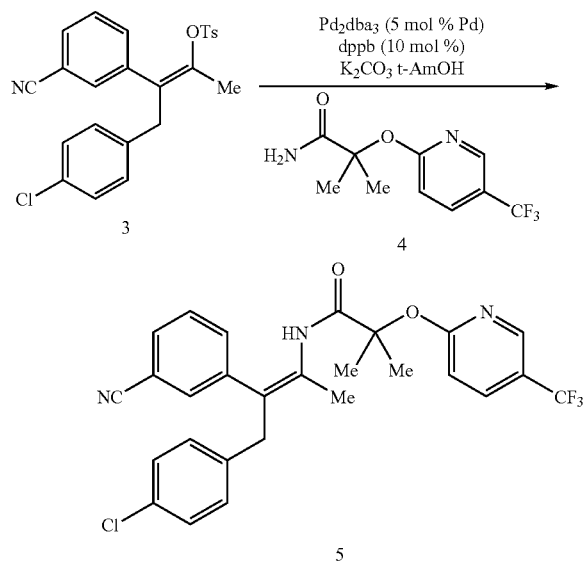

A 3-neck 3 L round bottom flask was charged with tert-amyl alcohol (2.4 L). Nitrogen gas was bubbled through the solution for 2 hours. A 3-neck 5 L round bottom flask fitted with a mechanical stirrer, reflux condenser, and a nitrogen/vacuum adapter on top of the reflux condenser was charged with $Pd_2 dba_3$ (27.5 g), 1,4-bis(diphenylphosphino)butane (51.2 g), 2-methyl-2{[5-(trifluoromethyl)pyridine-2-yl]oxy}propanamide (313 g), 3-(4-chlorophenyl)-2-(3-cyanophenyl)-1-methylprop-1-en-1-yl 4-methylbenzenesulfonate (526 g), and potassium carbonate (332 g). The flask was sealed, evacuated, and backfilled with nitrogen. Tert-amyl alcohol (2.4 L) was added to the reaction flask followed by heating to 100° C. and stirring at 100° C. for 18 h. The resulting suspension was cooled to 25° C. and transferred into a 4-necked 22 L round bottom flask equipped with a mechanical stirrer. The batch was diluted with 7.2 L of MTBE, then DARCO KB-B® (250 g) was charged to the mixture. The resulting mixture was stirred for 2 h at RT, then filtered over a pad of SOLKA FLOC. The filter cake was washed with 7 L of MTBE. The batch was vacuum transferred to a 4-necked 12 L round bottom flask equipped with an overhead stirrer and thermocouple. The batch was concentrated at 10-20° C. to remove all the MTBE and then at 30-40° C. to reduce the volume of the remaining t-amyl alcohol to ~1.5 L. Heptane (5 L) was added over ~30 minutes and the batch was cooled to 20° C. The filter cake was washed with 2 L of heptane-MTBE (10:1) and dried under a stream of nitrogen to provide 553 g of the title compound).

Figure 7:
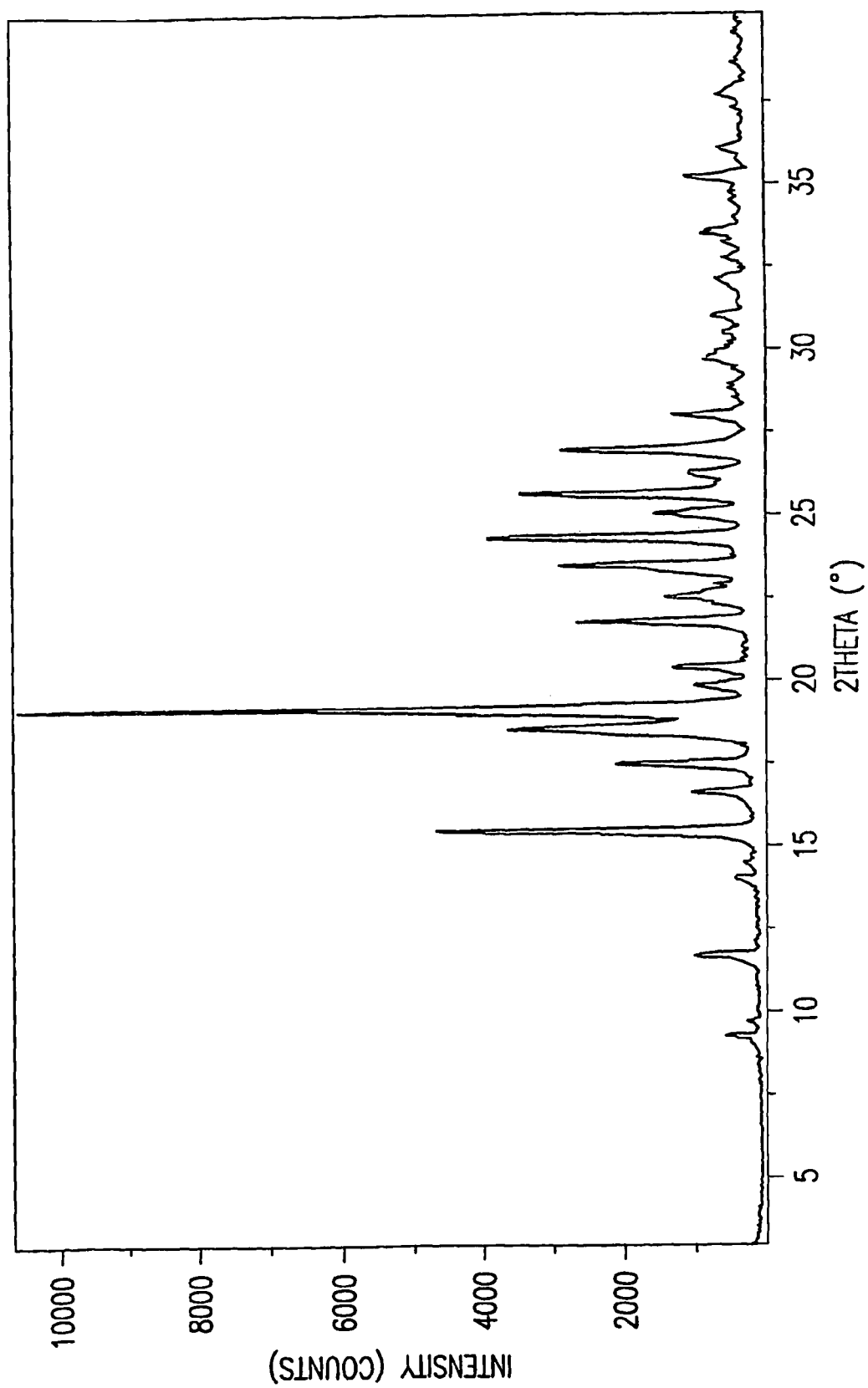
FIG. 7 shows the X-ray powder diffraction pattern of the N-[(1Z)-3-(4-chlorophenyl)-2-(3-cyanophenyl)-1-methylprop-1-en-1-yl]-2-methyl-2-{[5-(trifluoromethyl)pyridin-2-yl]oxy}propanamide (EXAMPLE 4), generated on a Philips Analytical X'Pert PRO X-ray Diffraction System with PW3040/60 console using a PW3373/00 ceramic Cu LEF X-ray tube K-Alpha radiation as the source.

XRPD: FIG. 7 shows the X-ray powder diffraction pattern of the title compound generated on a Philips Analytical X'Pert PRO X-ray Diffraction System with PW3040/60 console, using a PW3373/00 ceramic Cu LEF X-ray tube K-Alpha radiation as the source. The title compound exhibited characteristic diffraction peaks corresponding to d-spacings of 7.6, 5.7, 5.3, 5.1, 4.6, 4.1 angstroms.

Figure 8:
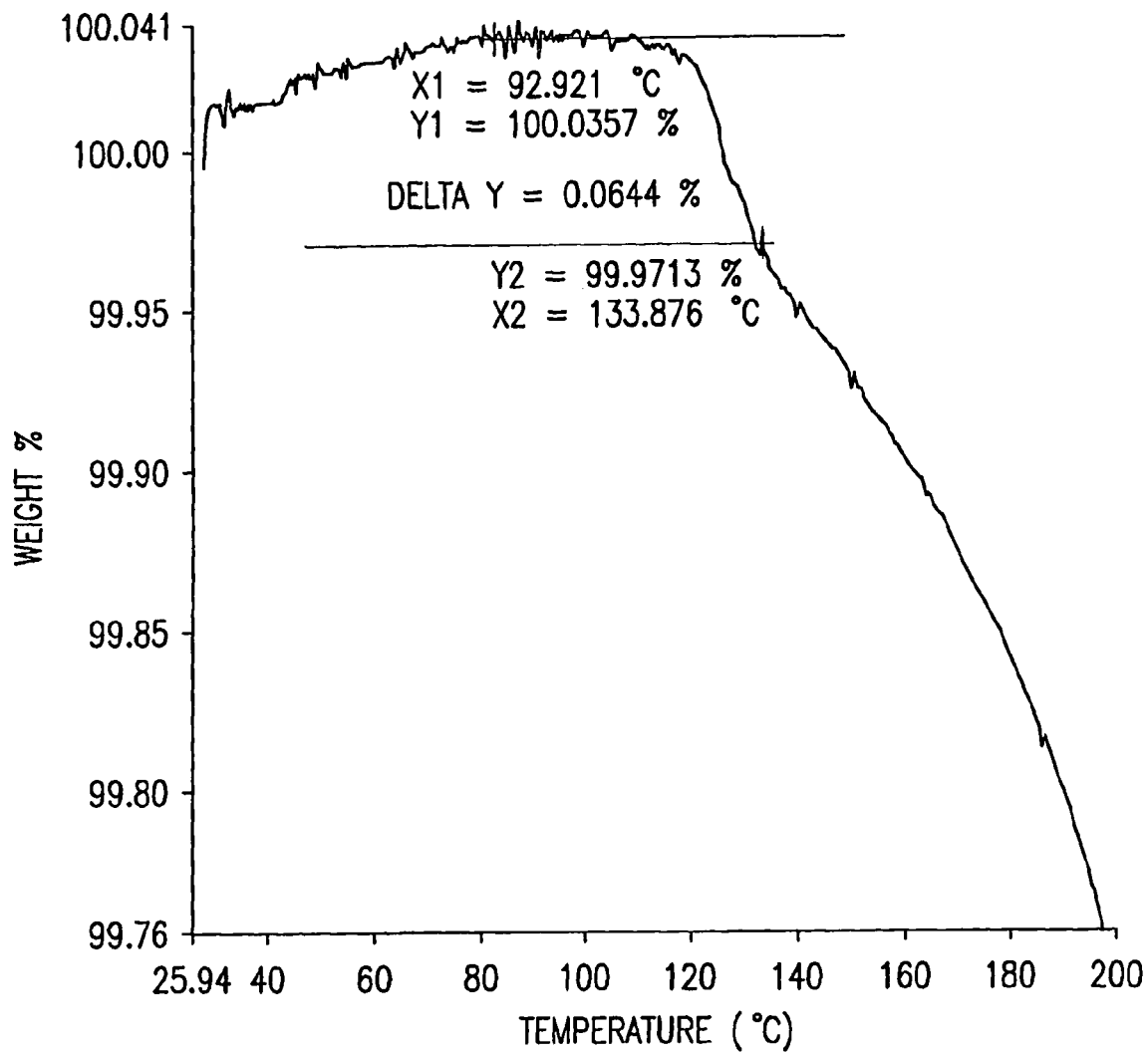
FIG. 8 shows the thermogravimetry (TG) data of N-[(1Z)-3-(4-chlorophenyl)-2-(3-cyanophenyl)-1-methylprop-1-en-1-yl]-2-methyl-2-{[5-(trifluoromethyl)pyridin-2-yl]oxy}propanamide (EXAMPLE 4) obtained at a heating rate of 10° C./min under nitrogen atmosphere.
Figure 9:
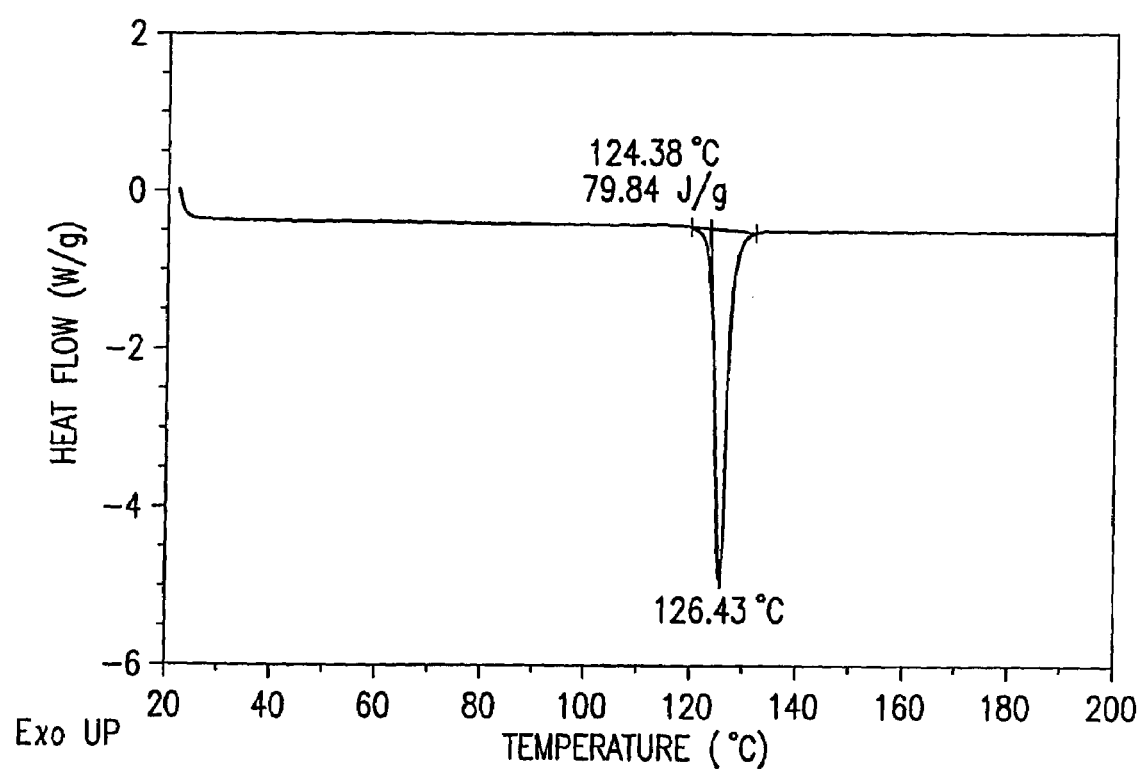
FIG. 9 shows the differential scanning calorimetry (DSC) data collected at a heating rate of 10° C./min, under nitrogen atmosphere in a hermetic pan for N-[(1Z)-3-(4-chlorophenyl)-2-(3-cyanophenyl)-1-methylprop-1-en-1-yl]-2-methyl-2-{[5-(trifluoromethyl)pyridin-2-yl]oxy}propanamide (EXAMPLE 4), displaying a melting endotherm with an extrapolated onset temperature of 124.4° C., a peak temperature of 126.4° C., and an enthalpy change of 80 J/g.

Thermal Analysis (TG and DSC): The thermogravimetry (TG) data of the intermediate cyanoenamide was obtained at a heating rate of 10° C./min under nitrogen atmosphere and shown in FIG. 8. A weight loss of 0.06% was observed from 83 to 134° C. Differential scanning calorimetry (DSC) data were collected at a heating rate of 10° C./min, under nitrogen atmosphere in a hermetic pan. The DSC curve of the intermediate cyanoenamide is shown in FIG. 9 and displays a melting endotherm with an extrapolated onset temperature of 124.4° C., a peak temperature of 126.4° C., and an enthalpy change of 80 J/g.

EXAMPLE 5

N-[(1Z)-3-(4-chlorophenyl)-2-(3-cyanophenyl)-1-methylprop-1-en-1-yl]-2-methyl-2-{[5-(trifluoromethyl)pyridin-2-yl]oxy}propanamide Preparation 2

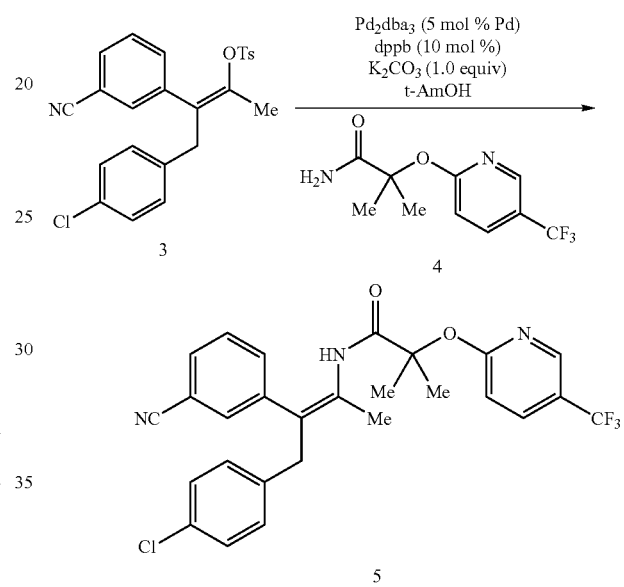

A 250 mL three-neck round bottom flask was equipped with a reflux condenser on the first neck and an overhead stirrer on the middle neck. A nitrogen/vacuum inlet adapter was attached on top of the reflux condenser. All glass joints were greased with Dow Corning high vacuum grease. The flask was charged with $Pd_2 dba_3$ (0.687 g), 1,4-bis(diphenylphosphino)butane (1.28 g), 2-methyl-2{[5-(trifluoromethyl)pyridine-2-yl]oxy}propanamide (7.82 g), 3-(4-chlorophenyl)-2-(3-cyanophenyl)-1-methylprop-1-en-1-yl 4-methylbenzenesulfonate (13.1 g), and potassium carbonate (4.15 g), capped with a rubber septum on the third neck of the flask, evacuated, and backfilled with nitrogen. Tert-Amyl alcohol (60 mL) was added via syringe. A TEFLON coated thermocouple was inserted by puncturing the septum on the third neck, and the puncture point was sealed with a dab of Dow Corning high vacuum grease. The stirring and heating (oil bath) was started. The reaction mixture was stirred at 150 rpm and 100° C. for 18 h, at which time HPLC analysis indicated complete conversion. The reaction mixture was then diluted with MTBE (180 mL), stirred with DARCO KB-B (6.0 g) for 2 h without exclusion of air, and filtered through SOLKA FLOC eluting with MTBE (180 mL). The filtrate was analyzed by HPLC to provide 92% assay yield, 7% amide starting material and 3% of the rearranged amide. The yellow filtrate was then concentrated to 50 mL volume. The product was precipitated by addition of heptane (150 mL) over 30 nm in while the mixture was stirred magnetically. After stirring for 1 h at room temperature, the suspension was filtered and the cake was washed with 10:1 heptane-MTBE (100 mL) resulting in 4.4 wt % mother liquor losses. After drying under vacuum, 13.6 g of the product as a pale yellow powder was obtained in 87% isolated yield, 98.3 wt % purity, and with 1.3% LCAP of the dppb oxide impurity.

EXAMPLE 6

N-[(1Z)-3-(4-chlorophenyl)-2-(3-cyanophenyl)-1-methylprop-1-en-1-yl]-2-methyl-2-{[5-(trifluoromethyl)pyridin-2-yl]oxy}propanamide Preparation 3

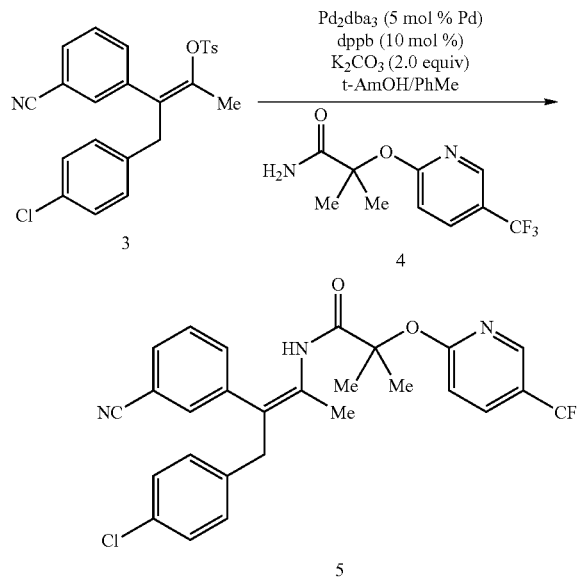

A 100 mL 24/40 joint three-neck round bottom flask was equipped with a reflux condenser on the first neck and an overhead stirrer on the middle neck. A nitrogen/vacuum inlet adapter was attached on top of the reflux condenser. All glass joints were greased with Dow Corning high vacuum grease. The flask was charged with t-AmOH (24 mL), 1,4-bis(diphenylphosphino)butane (0.512 g), 2-methyl-2{[5-(trifluoromethyl)pyridine-2-yl]oxy}propanamide (3.13 g), 3-(4-chlorophenyl)-2-(3-cyanophenyl)-1-methylprop-1-en-1-yl 4-methylbenzenesulfonate (5.26 g), and potassium carbonate (3.31 g). The headspace of the vessel was purged with nitrogen (inlet on top of the condenser, outlet on the third neck of the flask) while stirred at 50 rpm for 1 h.

A separate 50 mL round bottom flask was charged with $Pd_2dba_3$ (0.275 g) and toluene (12 mL), and the headspace of the flask was purged with a slow stream of nitrogen while the suspension was stirred magnetically at room temperature for 30 min.

After the inertization of the first flask was complete, the nitrogen outlet adapter on the third neck of the first flask was replaced with a rubber septum. The catalyst suspension from the second flask was added via syringe to the first flask. A TEFLON coated thermocouple was inserted by puncturing the septum on the third neck of the first flask, and the puncture point was sealed with a dab of Dow Corning high vacuum grease. The stirring and heating (oil bath) was started. The reaction mixture was stirred at 150 rpm and 100° C. for 16 h, at which time HPLC analysis indicated complete conversion. The reaction mixture was then transferred into a 200 mL round bottom flask using MTBE (75 mL), stirred with DARCO KB-B (2.6 g) for 3 h without exclusion of air, and filtered through SOLKA FLOC eluting with MTBE (75 mL). The filtrate was analyzed by HPLC to provide 95% assay yield, 4% amide starting material and 2% of the rearranged amide. The yellow filtrate was concentrated to 20 mL volume and the product was precipitated by addition of heptane (60 mL) over 10 min while the mixture was stirred magnetically. After stirring for 3 h at room temperature, the suspension was filtered and the cake was washed with 10:1 heptane-MTBE (50 mL) resulting in 3.3 wt % mother liquor losses. After drying under vacuum, 5.63 g of the product as a pale yellow powder was obtained in 91% isolated yield, 99.2 wt % purity, and with 0.45% LCAP of the dppb oxide impurity.

EXAMPLE 7

3-{(1Z)-1-(4-chlorobenzyl)-2-[(2-methyl-2-{[5-trifluoromethyl)pyridin-2-yl]oxy}propanoyl)amino]-prop-1-en-1-yl}benzamide

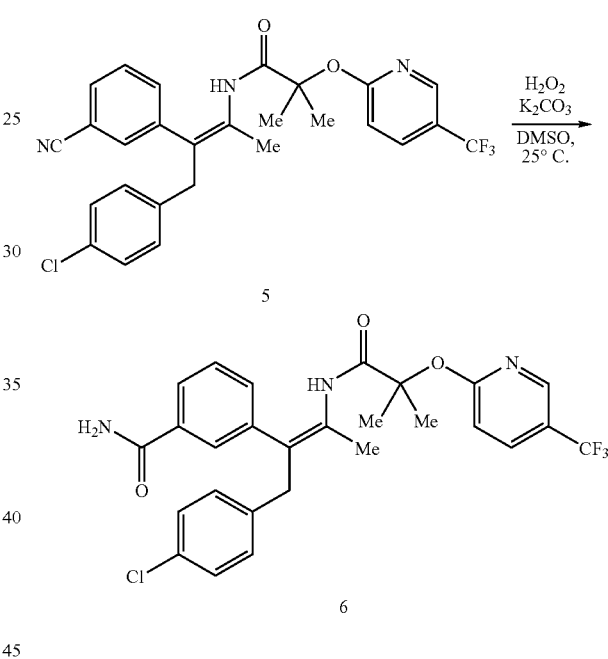

To a 5 L, 3-necked round bottom flask equipped with overhead stirrer, thermocouple, and nitrogen inlet was added 524 g of the cyano enamide product of Example 4, N-[(1Z)-3-(4-chlorophenyl)-2-(3-cyanophenyl)-1-methylprop-1-en-1-yl]-2-methyl-2-{[5-(trifluoromethyl)pyridin-2-yl]oxy}propanamide, and 112 g $K_2CO_3$. DMSO (2.7 L) was charged and the vessel was submerged in a RT water bath. Hydrogen peroxide solution (165 mL of a 30% aqueous solution) was slowly added to the reactor such that the temperature never rose above 25° C. After the addition was complete, the reaction was aged for 1 hour. The batch was diluted with 1 L of isopropyl acetate and filtered over a bed of SOLKA FLOC. The bed was washed with 4.5 L of isopropyl acetate and the resulting solution was transferred to a 50 L extractor containing 5.5 L of water. The layers were separated and the organic layer was washed twice with 3.1 L of water, concentrated to 5 L, and solvent switched to 5 L toluene at ~60° C. Upon completion of the solvent switch, 500 mL heptane was added and the mixture was cooled to 20° C. The batch was aged for 30 minutes at 20° C., then filtered and washed with 1 L of toluene. The resulting solid was dried overnight under a stream of nitrogen to afford 522 g of the title compound (99.4 LCAP, 98.0 wt %, 0.02% dppb-oxide, 512 g assay).

Figure 10:
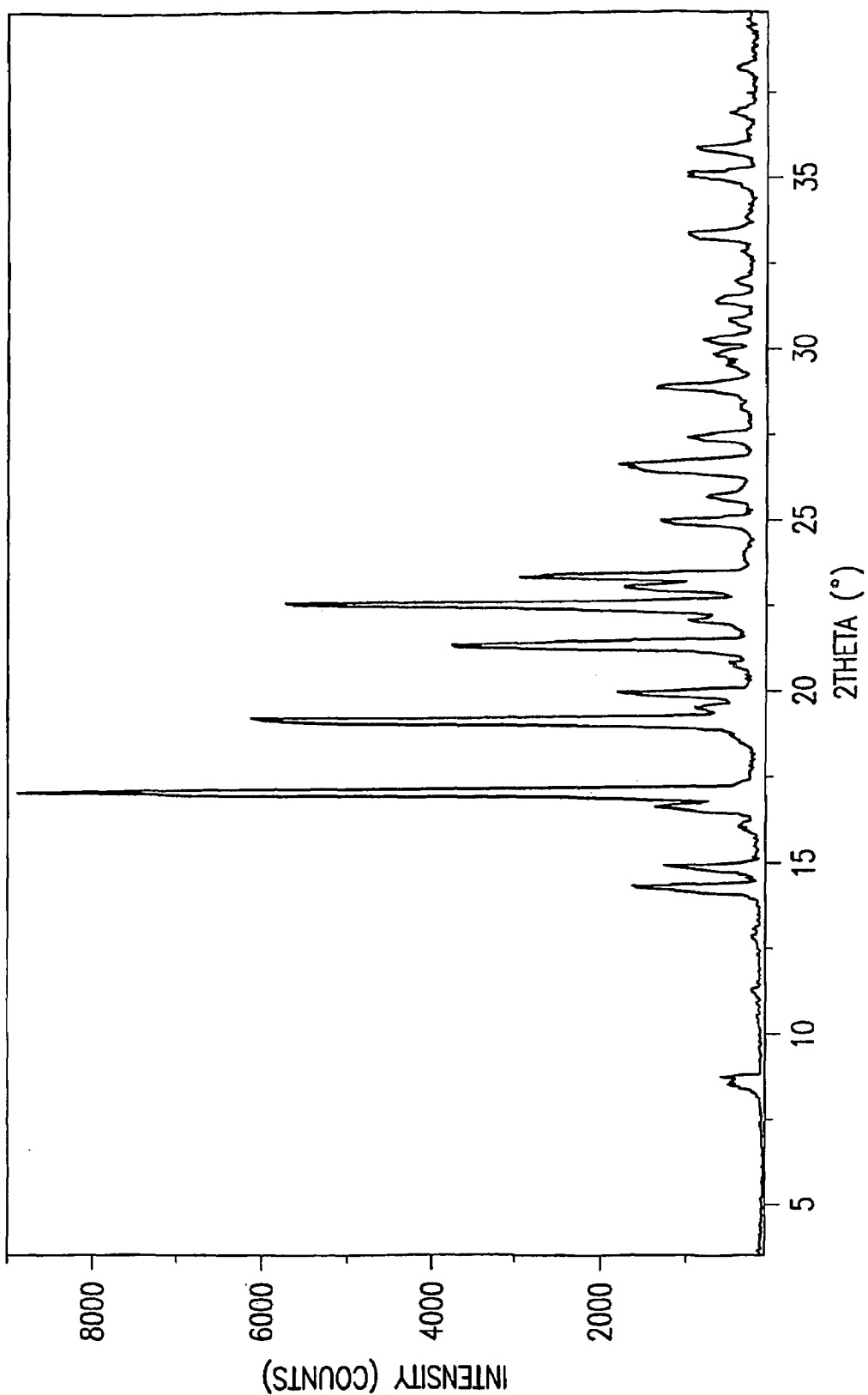
FIG. 10 shows the X-ray powder diffraction pattern of 3-{(1Z)-1-(4-chlorobenzyl)-2-[(2-methyl-2-{[5-(trifluoromethyl)pyridin-2-yl]oxy}propanoyl)amino]prop-1-en-1-yl}benzamide (EXAMPLE 7) generated on a Philips Analytical X'Pert PRO X-ray Diffraction System with PW3040/60 console using a PW3373/00 ceramic Cu LEF X-ray tube K-Alpha radiation as the source.

XRPD: FIG. 10 shows the X-ray powder diffraction pattern of the title compound generated on a Philips Analytical X'Pert PRO X-ray Diffraction System with PW3040/60 console using a PW3373/00 ceramic Cu LEF X-ray tube K-Alpha radiation as the source. The title compound exhibited characteristic diffraction peaks corresponding to d-spacings of 6.2, 5.9, 5.2, 4.6, 4.2, 3.9 angstroms.

Figure 11:
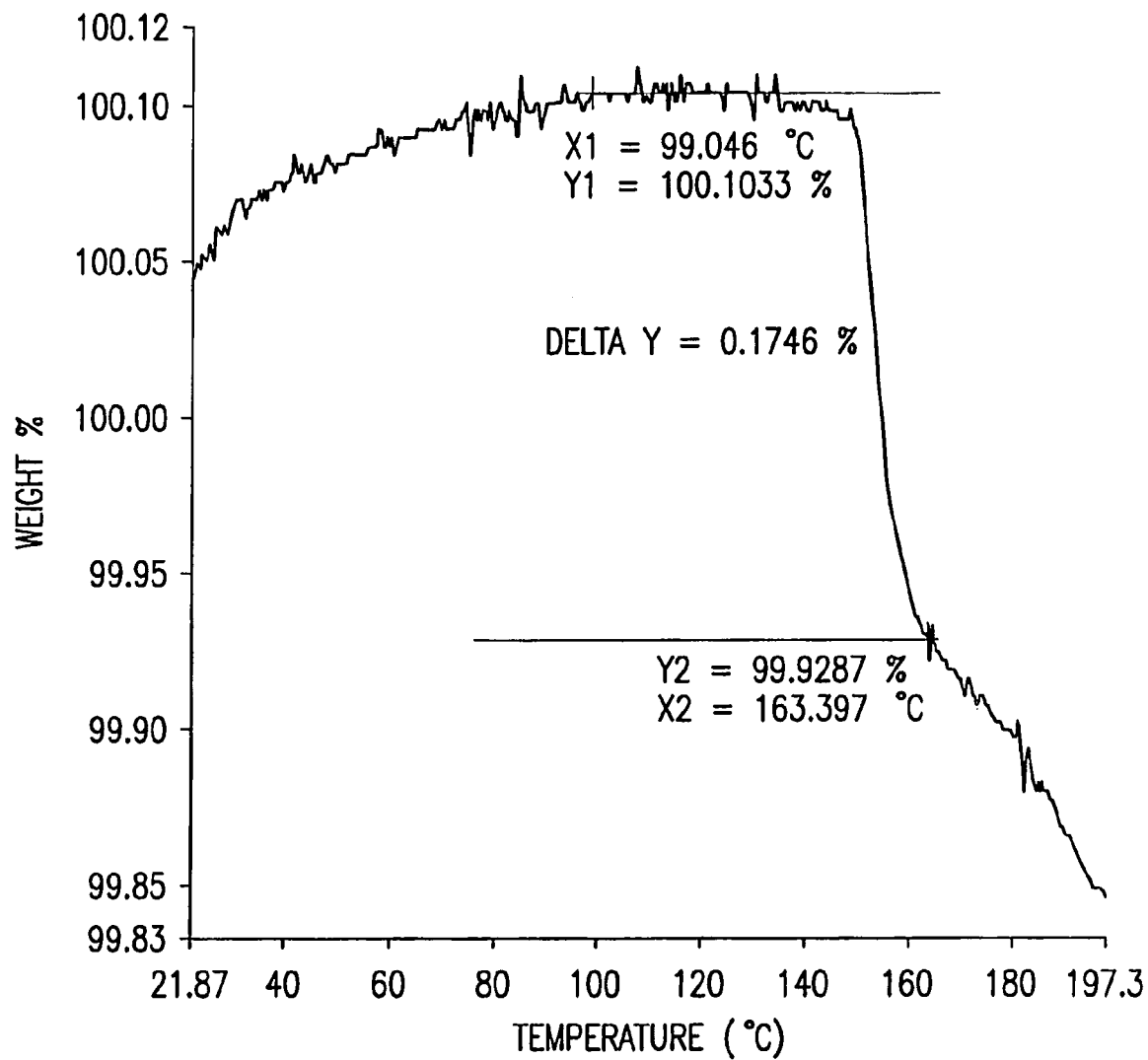
FIG. 11 shows the thermogravimetry (TG) data of 3-{(1Z)-1-(4-chlorobenzyl)-2-[(2-methyl-2-{[5-(trifluoromethyl)pyridin-2-yl]oxy}propanoyl)amino]prop-1-en-1-yl}benzamide (EXAMPLE 7) obtained at a heating rate of 10° C./min under nitrogen atmosphere.
Figure 12:
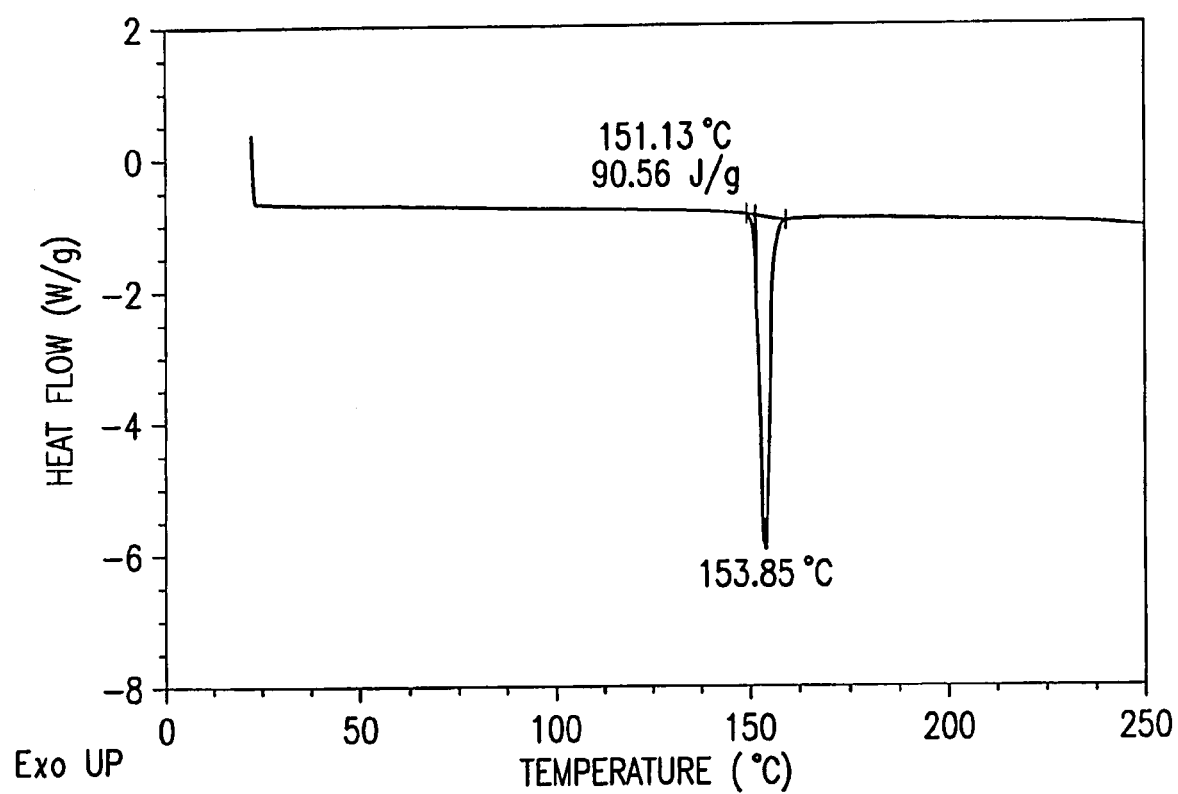
FIG. 12 shows differential scanning calorimetry (DSC) data collected at a heating rate of 10° C./min, under nitrogen atmosphere in a hermetic pan for 3-{(1Z)-1-(4-chlorobenzyl)-2-[(2-methyl-2-{[5-(trifluoromethyl)pyridin-2-yl]oxy}propanoyl)amino]prop-1-en-1-yl}benzamide (EXAMPLE 7) displaying a melting endotherm with an extrapolated onset temperature of 151.1° C., a peak temperature of 153.9° C., and an enthalpy change of 91 J/g.

Thermal Analysis (TG and DSC): The thermogravimetry (TG) data of the title compound was obtained at a heating rate of 10° C./min under nitrogen atmosphere and shown in FIG. 11. A weight loss of 0.17% was observed from 99 to 163° C. Differential scanning calorimetry (DSC) data were collected at a heating rate of 10° C./min, under nitrogen atmosphere in a hermetic pan. The DSC curve of the title compound is shown in FIG. 12 and displays a melting endotherm with an extrapolated onset temperature of 151.1° C., a peak temperature of 153.9° C., and an enthalpy change of 91 J/g.

EXAMPLE 8

3-{(1S,2S)-1-(4-chlorobenzyl)-2-[(2-methyl-2-{[5-(trifluoromethyl)pyridine-2-yl]oxy}propanoyl)amino]-propyl}benzamide Preparation 1

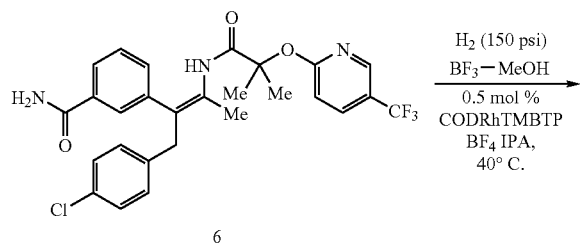

Step A: Catalyst Preparation

In a $N_2$-filled glove box, 2.83 g (−)-TMBTP was added to a 0.5 L bottle containing a stir bar. $(COD)_2Rh\,BF_4$ (1.85 g) was added to the same bottle and then methanol (360 mL) was added. The resulting solution was aged with stirring for 1 hour. $BF_3 \cdot MeOH$ (41.2 g, 12 wt % in MeOH, 4.94 g $BF_3$) was added to the catalyst solution, and the resulting mixture was added to a 1-L stainless steel bomb. 50 mL of MeOH was used to rinse the mixture into the bomb. Isopropanol (200 mL) was charged to the rinse chamber of the bomb, and then each chamber of the bomb was sealed before removing it from the glove box.

Step B: Hydrogenation

3-{(1Z)-1-(4-chlorobenzyl)-2-[(2-methyl-2-{[5-(trifluoromethyl)pyridin-2-yl]oxy}propanoyl)amino]-prop-1-en-1-yl}benzamide (486 g, Example 7) was charged to a 5 L bottle, and isopropanol (3.3 L) was added to the bottle to create a slurry. The resulting slurry was transferred by vacuum through a polyethylene line into a 2 gallon stainless steel autoclave. The 5-L bottle was rinsed with 1 L of isopropanol and the rinse was also transferred into the 2 gallon autoclave. The autoclave was degassed with $N_2$ (5×), and then placed under partial vacuum. The catalyst bomb was connected to the autoclave via flexible polyethylene tubing (flushed with $N_2$) and the catalyst solution was drawn into the autoclave followed by the isopropanol wash from the rinse chamber. The autoclave was sealed, degassed with $N_2$ purges three times, degassed with $H_2$ purges three times and pressurized up to 150 psi. The stirrer was initiated, and the temperature was raised to 40° C. The reaction was aged at 150 psi, 40° C. for 18 hours. The temperature was dropped to room temperature, and the resulting solution was transferred to a polyethylene jug and assayed for ee and purity (475.7 g assay of the title compound, 98% assay yield, 99.6 LCAP, 92.1% ee).

EXAMPLE 9

3-{(1S,2S)-1-(4-chlorobenzyl)-2-[(2-methyl-2-[[5-(trifluoromethyl)pyridine-2-yl]oxy}propanoyl)amino]-propyl]benzamide Preparation 2

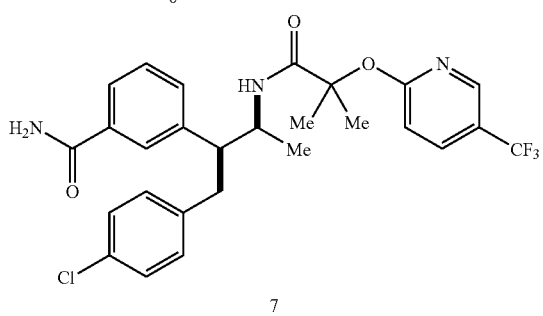

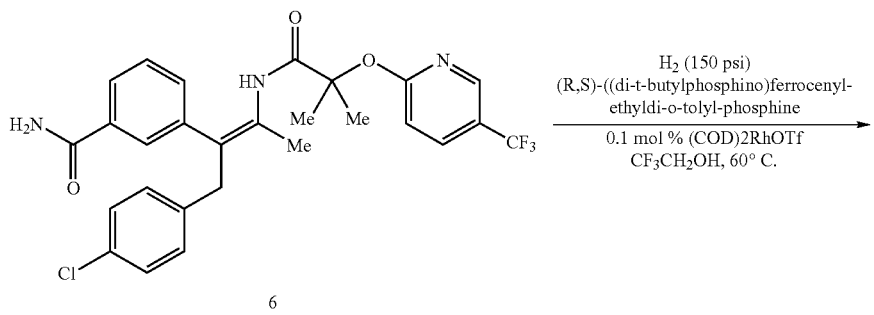

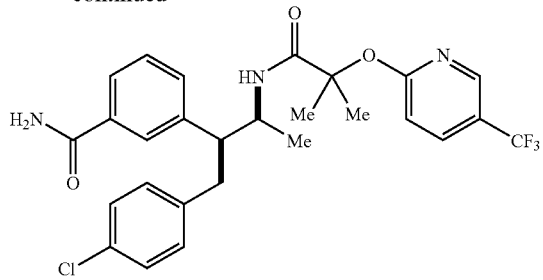

7

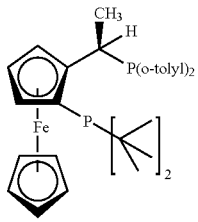

(R,S)-((di-t-butylphosphino)ferrocenyl-ethyldi-o-tolyl-phosphine

Step A: Catalyst Preparation

Note: In this experiment only degassed solvent was used and both the Schlenk flasks and the autoclave were placed under an atmosphere of argon gas prior to any loadings. (COD)$_2$RhOTf (23.41 mg, 0.05 mmol) and 29.95 mg (0.0525 mmol) (R,S)-((di-t-butylphosphino)ferrocenyl-ethyldi-o-tolyl-phosphine were placed in a 20 mL Schlenk flask. Subsequently, 10 mL 2,2,2-trifluoroethanol were added and the reaction mixture was stirred for 1 h at 60° C.

Step B: Hydrogenation

3-{(1Z)-1-(4-chlorobenzyl)-2-[(2-methyl-2-{[5-(trifluoromethyl)pyridin-2-yl]oxy}propanoyl)amino]-prop-1-en-1-yl}benzamide (26.6 g, 50.0 mmol) was placed in a 250 mL Schlenk flask and 2,2,2-trifluoroethanol (90 mL) was added. This slurry was agitated until a homogeneous solution was obtained. This solution was transferred via cannula into a 300 mL stainless steel autoclave followed by the catalyst solution. The autoclave was sealed, purged with hydrogen gas (3 cycles 140 psig/14 psig), and the reactor was heated to 60° C. After 20 minutes, the pressure was set to 150 psig H$_2$ and stirring initiated. The reaction was aged for 16 hours. The temperature was dropped to room temperature and the hydrogen was removed. The resulting solution was removed from the autoclave and assayed for ee and purity (25.7 g assay of the title compound, 96% assay yield, 99.8 LCAP, 95.3% ee).

EXAMPLE 10

3-{(1S,2S)-1-(4-chlorobenzyl)-2-[(2-methyl-2-{[5-(trifluoromethyl)pyridine-2-yl]oxy}propanoyl)amino]-propyl}benzamide Preparation 3

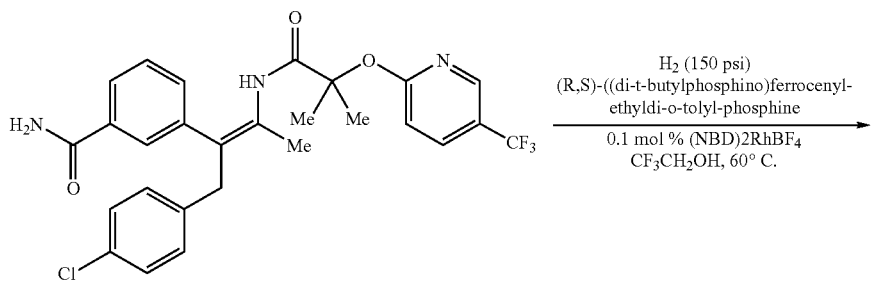

6

-continued

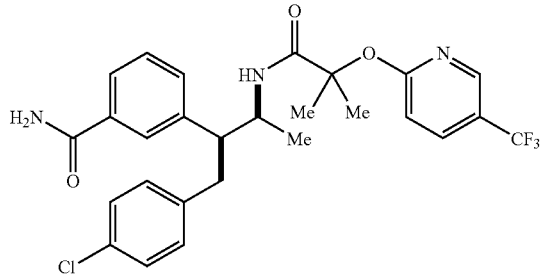

7

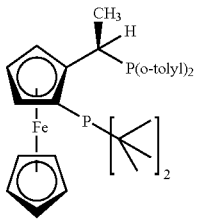

(R,S)-((di-t-butylphosphino)ferrocenyl-ethyldi-o-tolyl-phosphine

Step A: Catalyst Preparation

Note: In this experiment only degassed solvent was used and both the Schlenk flasks and the autoclave were placed under an atmosphere of argon gas prior to any loadings. (NBD)$_2$RhBF$_4$ (18.7 mg) and (R,S)-((di-t-butylphosphino)ferrocenyl-ethyldi-o-tolyl-phosphine (29.95 mg) were placed in a 20 mL Schlenk flask. Subsequently, 10 mL 2,2,2-trifluoroethanol were added and the reaction mixture was stirred for 10 minutes at ambient temperature.

Step B: Hydrogenation

3-{(1Z)-1-(4-chlorobenzyl)-2-[(2-methyl-2-{[5-(trifluoromethyl)pyridin-2-yl]oxy}propanoyl)amino]-prop-1-en-1-yl}benzamide (26.6 g) was placed in a 250 mL Schlenk flask and 2,2,2-trifluoroethanol (90 mL) was added. This slurry was agitated until a homogeneous solution was obtained. This solution was transferred via cannula into a 300 mL stainless steel autoclave followed by the catalyst solution. The autoclave was sealed, purged with hydrogen gas (3 cycles 140 psig/14 psig), and the reactor was heated to 60° C. After 20 minutes, the pressure was set to 150 psig H$_2$ and stirring initiated. The reaction was aged for 17 hours. The temperature was dropped to room temperature and the hydrogen was removed. The resulting solution was removed from the autoclave and assayed for ee and purity (23.9 g assay of the title compound, 90% assay yield, 99.8 LCAP, 95.3% ee).

Step C: Isolation Procedure

A TFE solution of 2.68 g (5.02 mmol) of chiral amide 7 in TFE was concentrated to ~6.4 g or 1 kg/L at 39° C. and 75 mbar. Added 85.25 mL of MTBE and distilled at constant volume at 40-45° C. and 450 torr to remove additional TFE. Final TFE concentration was 1.47 wt. %. ECOSORB C-941 was added (0.271 g), and the solution was heated to 40° C. and aged for 20.75 hours. The slurry was filtered over SOLKA FLOC, and the filtrate was concentrated 50% supersaturation (46° C., 365 mbar). The solution was seeded with 13.8 mg of chiral amide (water concentration at this point was 816 ppm-wt. basis) and aged 18 hours at 20-25° C. A total of 33.09 mL n-heptane was added over 16 hours and the slurry was aged for 5 hours at 20-25° C. An additional 68 mL of n-heptane was added over 8 hours at 20-25° C. and aged for 1 hour. The slurry was filtered and washed with 40 mL of 5:1 n-heptane/MTBE at 20-25° C. Solids were dried in a vacuum oven at 45° C. and 0.1 in Hg for 17.75 hours to yield anhydrous chiral amide (1.95 g, 73% yield, 99.8% ee, <0.1% MTBE, TFE and n-heptane, 10 ppm Rh).

XRPD: The X-ray powder diffraction pattern of the title compound generated on a Philips Analytical X'Pert PRO X-ray Diffraction System with PW3040/60 console using a PW3373/00 ceramic Cu LEF X-ray tube K-Alpha radiation as the source. The anhydrous crystalline form of chiral amide 7 exhibited characteristic diffraction peaks corresponding to d-spacings of 8.2, 7.4, 6.0, 5.4, 4.5, 3.6 angstroms.

Thermal Analysis (TG and DSC): The thermogravimetry (TG) data of the anhydrous crystalline form of chiral amide 7 was obtained at a heating rate of 10° C./min under nitrogen atmosphere. A weight loss of 0.14% was observed from 33 to 151° C. Differential scanning calorimetry (DSC) data were collected at a heating rate of 10° C./min, under nitrogen atmosphere in an open pan. The DSC curve of the anhydrous crystalline form of the chiral amide 7 displays a melting endotherm with an extrapolated onset temperature of 144.4° C., a peak temperature of 148.5° C., and an enthalpy change of 50 J/g.

EXAMPLE 11

N-[1S,2S]-3-(4-chlorophenyl)-2-(3-cyanophenyl)-1-methylpropyl]-2-methyl-2-{[5-(trifluoromethyl pyridin-2-yl)oxy]propanamide Route B

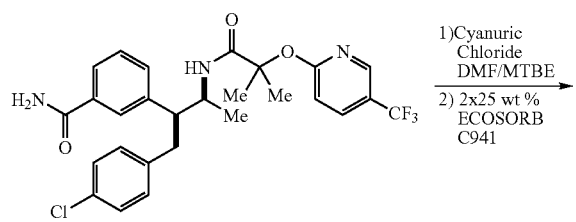

7

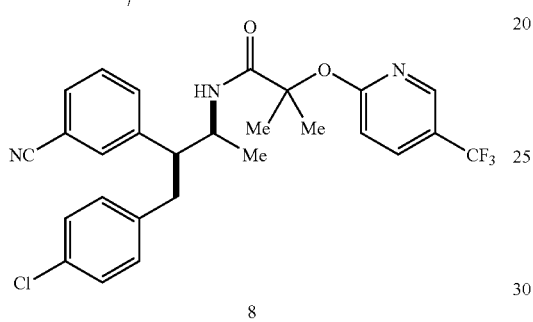

8

The crude hydrogenation solution from Example 10 was solvent switched from 4 L isopropanol to ~1 L DMF (40° C., 30 mm Hg). The resulting solution of 470 g of 3-{(1S,2S)-1-(4-chlorobenzyl)-2-[(2-methyl-2-{[5-(trifluoromethyl)pyridine-2-yl]oxy}propanoyl)amino]-propyl}benzamide (Example 10) in DMF was transferred to a 12 L 4-necked round bottom flask equipped with mechanical stirrer, thermocouple, and 2 L addition funnel. Cyanuric chloride (103 g) was slurried in 2 L of MTBE and the resulting slurry was charged to the reaction via the 2 L addition funnel over ~10 minutes. The reaction mixture was aged with stirring for 1 hour. The batch was cooled to 10° C. and diluted with 3 L of MTBE. 2 L of water and 2 L of saturated NaHCO$_3$ solution were added to the reaction while keeping the temperature below 20° C. The resulting slurry was transferred to a 50 L extractor containing 3 L of MTBE, 3 L of water, and 3 L of sat'd NaHCO$_3$. An additional 12 L of water was added to the batch and the layers were allowed to settle. The organic layer was washed twice with 3 L of water. Assay of the organic layer shows >99% assay yield.

Ecosorb Treatment/Hemisolvate Isolation: The organic layer was azeotroped at 35° C., 17 in Hg to bring the KF to 219 (spec. at 500) while maintaining a volume of ~11 L. The batch was then treated with 320 g of ECOSORB C941. The batch was aged for 4 hours at 50° C., then filtered over a pad of SOLKA FLOC and washed with 6 L of MTBE. The resulting filtrate was recharged to a 22 L vessel, concentrated to 11 L volume, and retreated with 116 g of ECOSORB C941. This slurry was filtered over a bed of SOLKA FLOC, and washed with 6 L MTBE. The resulting colorless MTBE layer was transferred through a 1 micron inline filter into a 12 L, 4 neck round bottom flask equipped with overhead stirrer and thermocouple, and concentrated to ~2 L volume at 17 in Hg, 35° C. The batch was cooled to RT, and a sample was removed to create a seed bed. Once the sample crystallized, it was returned to the flask, and the batch was aged for 30 minutes, creating a large seed bed. The isolated solid was dried over a stream of nitrogen to afford 413.4 g of the title compound as a hemisolvate (92.1% ee, 94.6 wt % title product, 99.8 area %, (0.08 area % methyl ester), 86% isolated yield from 7).

EXAMPLE 12

N-[1S,2S]-3-(4-chlorophenyl)-2-(3-cyanophenyl)-1-methylpropyl]-2-methyl-2-{[5-(trifluoromethyl pyridin-2-yl)oxy]propanamide Route B

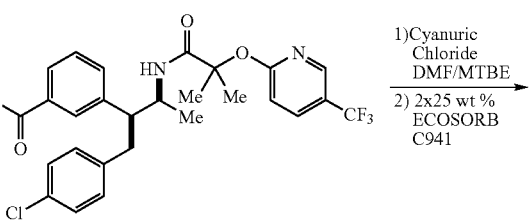

7

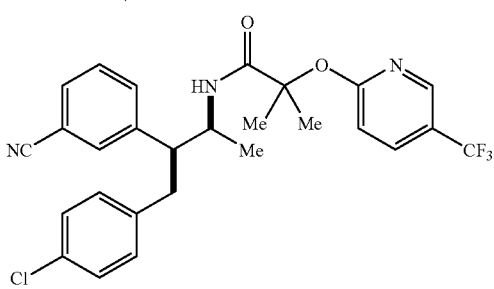

8

To a 3-necked, 2 L round bottom flask equipped with overhead stirrer and thermocouple was added DMF (100 mL), MTBE (250 mL) and cyanuric chloride (12.95 g). The resulting solution was aged for 2 hours. A solution of 3-{(1S,2S)-1-(4-chlorobenzyl)-2-[(2-methyl-2-{[5-(trifluoromethyl)pyridine-2-yl]oxy}propanoyl)amino]-propyl}benzamide (Example 10, 56.50 g, 88.5 wt %, 50 g assay) in DMF (50 mL) and MTBE (92 mL) was added to the flask over a period of ~45 minutes. The reaction was aged for 60 minutes, the MTBE (400 mL) was added, and the solution was cooled to 0° C. A solution of 10% aqueous NH$_4$Cl (500 mL) was added while keeping the temperature less than 10° C. The mixture was aged for 30 minutes and the layers were allowed to settle. The organic layer was washed with water (500 mL) twice, and the resulting organic solution was azeotroped with MTBE to reduce the water level to <500 ppm. ECOSORB C-941 (40 g) was added to the dry organic solution and the mixture was aged at 40° C. overnight. The mixture was cooled to room temperature, filtered, and washed with MTBE (200 mL). The solution was concentrated to 225-250 g/kg solution, seeded with 50 mg of hemisolvate, and aged overnight at room temperature. N-heptane (935 mL) was charged over 6 hours, and the slurry was cooled to 0° C. After aging for 1 hour, the batch was filtered and washed with n-heptane (235 mL) to afford 43.0 g of the title compound as a hemisolvate (92.1% ee, 94.6 wt % title product, 99.8 area %, 83% isolated yield).

EXAMPLE 13

Isolation of N-[1S,2S]-3-(4-chlorophenyl)-2-(3-cyanophenyl)-1-methylpropyl]-2-methyl-2-{[5-(trifluoromethyl pyridin-2-yl)oxy]propanamide Polymorph B In a 3 L, 3 neck round bottom flask equipped with overhead stirrer and thermocouple, 350 g of N-[1S,2S]-3-(4-chlorophenyl)-2-(3-cyanophenyl)-1-methylpropyl]-2-methyl-2-{[5-(trifluoromethyl pyridin-2-yl)oxy]propanamide hemisolvate was slurried in a total of 1.82 L of 2:3 isopropyl acetate:heptane. The mixture was aged for 1 h, and then filtered over a very small bed of SOLKA FLOC, thoroughly pull the liquors from the filter bed to minimize the loss of mother liquors. The filter cake was washed with 1 L of 1:3 IPAc:heptane into a separate flask. The two filtrates were combined (combined ee=98.5% ee). These two solutions were transferred by vacuum through a 1 micron inline filter into a 22 L 4 neck round bottom flask. The batch was heated to 45° C. over a steam pot, and then charged with 2.35 L of heptane. Seed of N-[1S,2S]-3-(4-chlorophenyl)-2-(3-cyanophenyl)-1-methylpropyl]-2-methyl-2-{[5-(trifluoromethyl pyridin-2-yl)oxy]propanamide Polymorph B (Polymorph B seed was obtained from the same solvent system over a long time frame) (15.0 g) was added and the batch was aged at 45° C. overnight. The resulting slurry was then charged with 150 mL of heptane over 5 hours, then 220 mL heptane at 2.0 mL/min, then 1131 mL of heptane at 9 mL/min, then 6783 mL of heptane at 60 mL/min. Once all heptane was charged, the batch was cooled to RT and aged overnight. The batch was cooled to 0° C. and aged for 1 hour, filtered, and washed with 1 L of heptane to afford the title compound, crystal Form B (287 g, 87% isolated yield (from hemisolvate and corrected for seed), 98.6% ee, 99.5 LCAP, 99.5 wt % assay).

EXAMPLE 14

Isolation of 3-{(1S,2S)-1-(4-chlorobenzyl)-2-[(2-methyl-2-{[5-(trifluoromethyl)pyridine-2-yl]oxy}propanoyl)amino]-propyl}benzamide

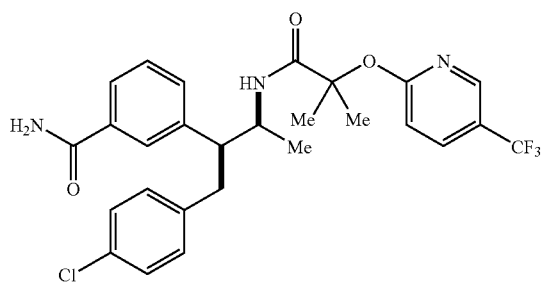

7

After the hydrogenation was complete (Example 8), solvent was removed on rotovap. The crude oil was diluted with toluene (10 ml/g) and 10% NH$_4$Cl solution (10 mL/g). The layers were separated, and the toluene layer was concentrated to an oil. The oil was diluted with MTBE (3 ml/g), seeded with 5 wt % chiral amide (7) MTBE hemisolvate and stirred overnight. After a seed bed was generated, heptane (3 mL/g) was added, and the batch was cooled to 10° C. before filtering. 90% recovery of the §0 title product on 3 g scale, 2% in liquors, some stuck to flask. 99.6 LCAP. 0.2% methyl ester impurity.

Figure 13:
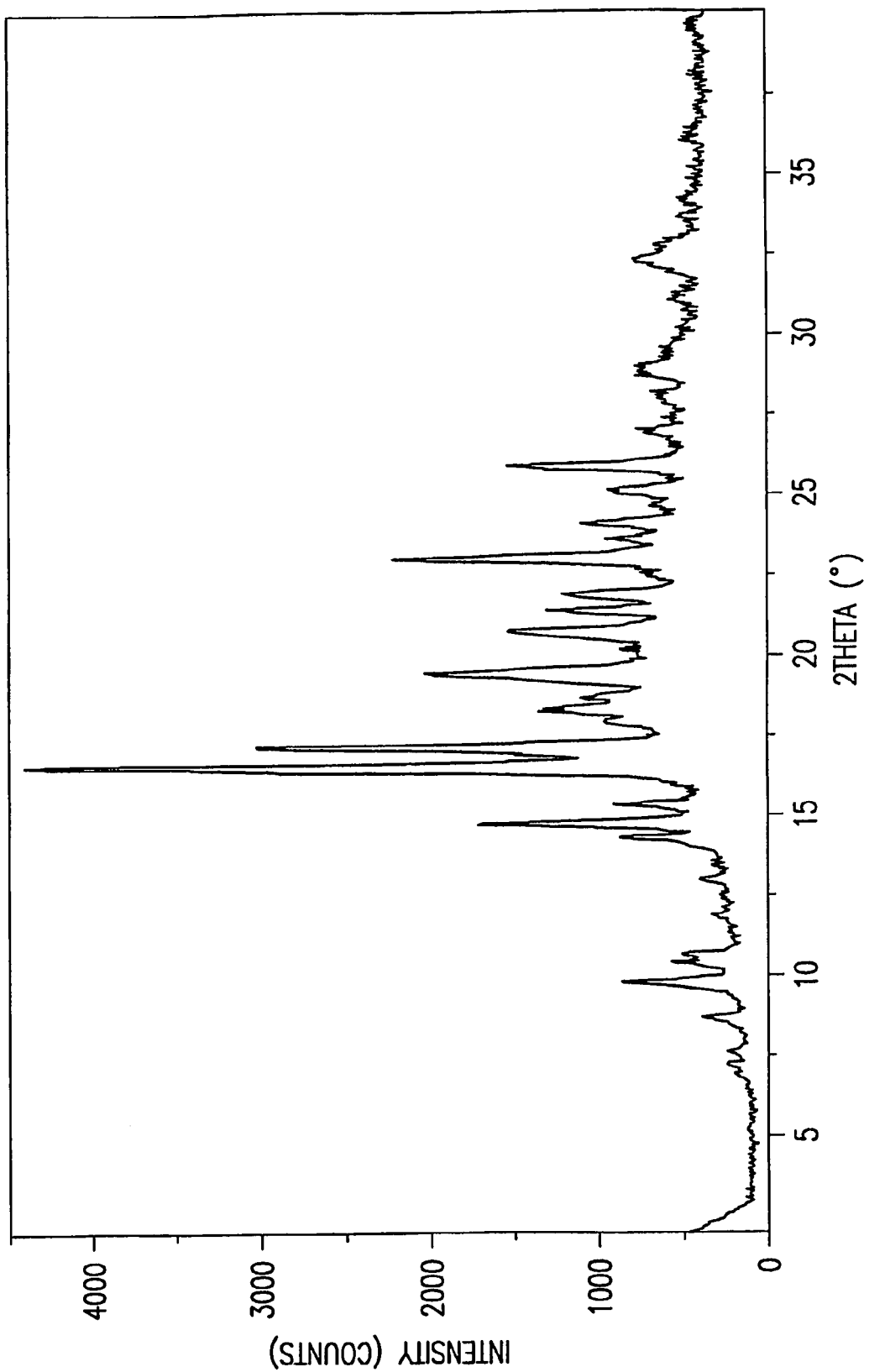
FIG. 13 shows the X-ray powder diffraction pattern of 3-{(1S,2S)-1-(4-chlorobenzyl)-2-[(2-methyl-2-{[5-(trifluoromethyl)pyridine-2-yl]oxy}propanoyl)amino]-propyl}benzamide (EXAMPLES 8 14) generated on a Philips Analytical X'Pert PRO X-ray Diffraction System with PW3040/60 console using a PW3373/00 ceramic Cu LEF X-ray tube K-Alpha radiation as the source.

XRPD: FIG. 13 shows the X-ray powder diffraction pattern of the title compound generated on a Philips Analytical X'Pert PRO X-ray Diffraction System with PW3040/60 console using a PW3373/00 ceramic Cu LEF X-ray tube K-Alpha radiation as the source. The title compound exhibited characteristic diffraction peaks corresponding to d-spacings of 9.0, 6.0, 5.3, 5.1, 4.5, 3.9 angstroms.

Figure 14:
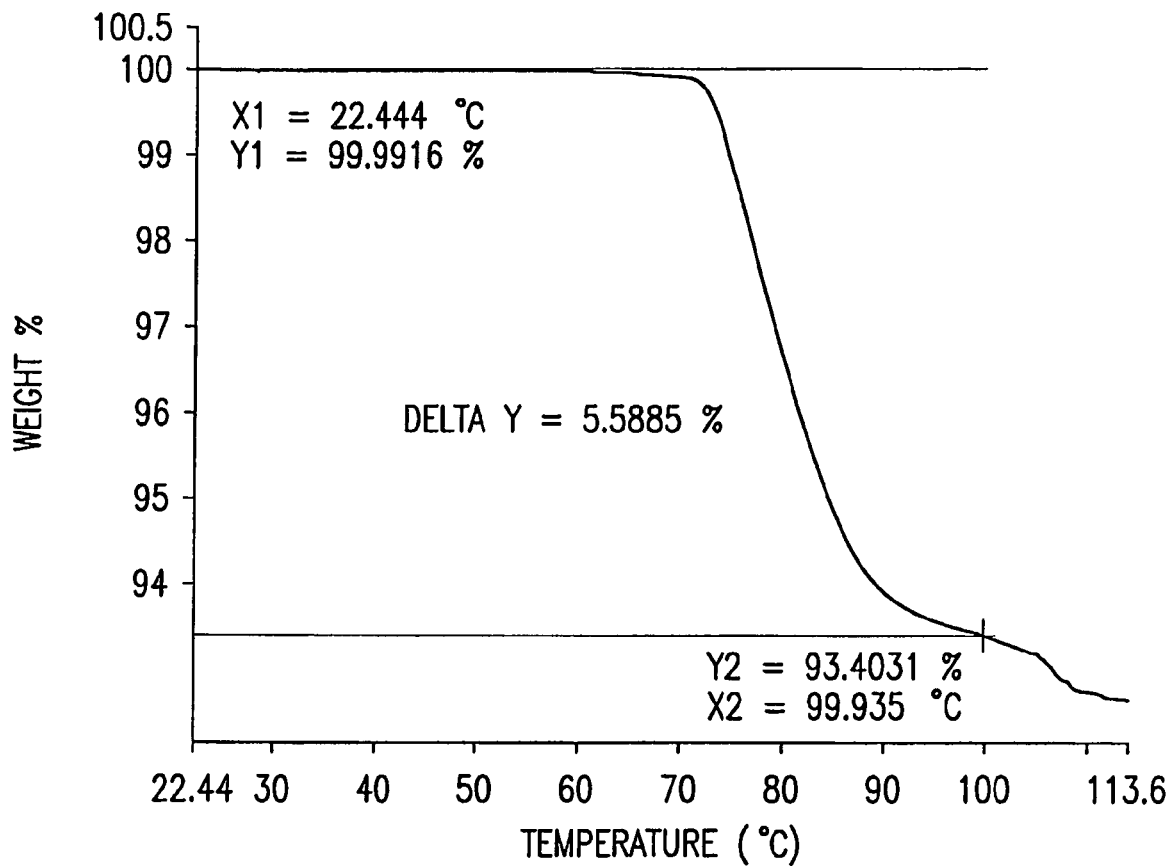
FIG. 14 shows the thermogravimetry (TG) data of 3-{(1S,2S)-1-(4-chlorobenzyl)-2-[(2-methyl-2-{[5-(trifluoromethyl)pyridine-2-yl]oxy}propanoyl)amino]-propyl} (EXAMPLES 8 & 14) obtained at a heating rate of 10° C./min under nitrogen.
Figure 15:
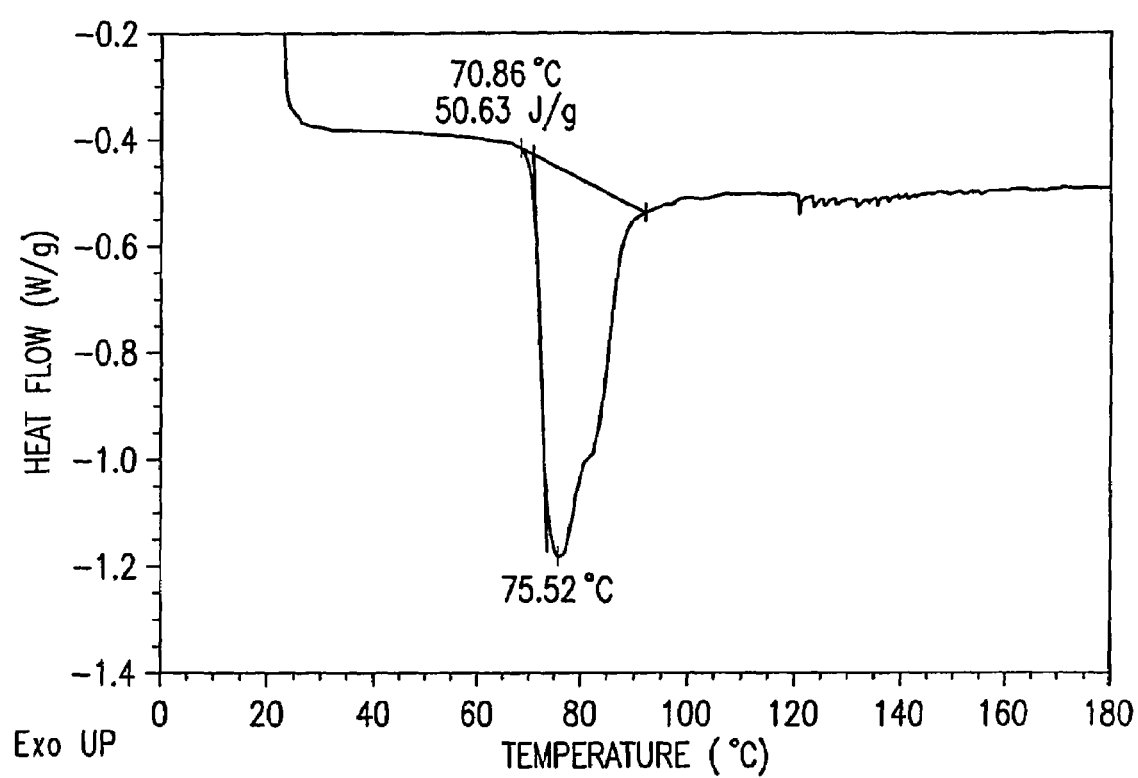
FIG. 15 shows the differential scanning calorimetry (DSC) data collected at a heating rate of 10° C./min, under nitrogen atmosphere in a hermetic pan for 3-{(1S,2S)-1,4-chlorobenzyl)-2-[(2-methyl-2-{[5-(trifluoromethyl)pyridine-2-yl]oxy}propanoyl)amino]-propyl}benzamide (EXAMPLES 8 & 14) displaying a melting endotherm with an extrapolated onset temperature of 70.9° C., a peak temperature of 75.5° C., and an enthalpy change of 51 J/g.

Thermal Analysis (TG and DSC): The thermogravimetry (TG) data of the intermediate amide was obtained at a heating rate of 10° C./min under nitrogen atmosphere and shown in FIG. 14. A weight loss of 6.6% was observed from ambient temperature to 100° C. Differential scanning calorimetry (DSC) data were collected at a heating rate of 10° C./min, under nitrogen atmosphere in a hermetic pan. The DSC curve of the intermediate amide is shown in FIG. 15 and displays a melting endotherm with an extrapolated onset temperature of 70.9° C., a peak temperature of 75.5° C., and an enthalpy change of 51 J/g.

EXAMPLE 15

Isolation of 3-{(1S,2S)-1-(4-chlorobenzyl)-2-[(2-methyl-2-{[5-(trifluoromethyl)pyridine-2-yl]oxy}propanoyl)amino]-propyl}benzamide

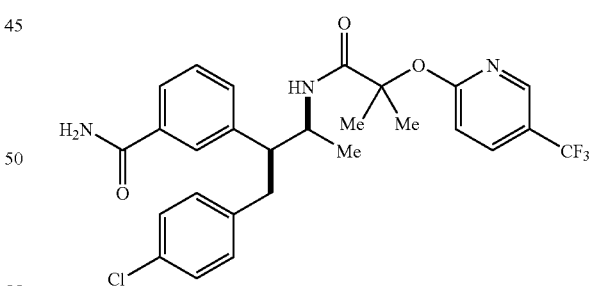

7

After the hydrogenation was complete (Example 8), 64.9 g of solution was concentrated to 16.9 g up to 45° C. under vacuum. The solubility of chiral amide in IPA exceeds 1350 g/L (grams of chiral amide per liter of solvent). MTBE (348.2 g) was added, and the solution was washed with 250 mL of 10% NH$_4$Cl solution. The organic solution was then washed an additional 3 times with water (248 mL for each wash). The residual organic solution was concentrated with MTBE (284.4 g) to azeotrope the water. The solution was concentrated to 53±5 g/kg. The final water concentration was 532 ppm. This solution was then seeded with chiral amide MTBE hemisolvate, 0.5 wt. %, and aged for 20 hours at 20-25° C. At this point, heptane was charge in three aliquots over specific periods of time. The first aliquot of heptane (54 mL), was charged in 9 hours. The second aliquot of heptane (90 mL) was charged in 6 hours. The third aliquot of heptane (294 mL) was charged in 3 hours. At the conclusion of the heptane charge, the solution was aged at 20-25° C. for 2 hours. The solution was filtered over a 5 micron fritted filter. A displacement wash was conducted using 164 mL of 5:1 n-heptane/MTBE, and the solids were dried at less than 45° C. under vacuum. The final water concentration was <0.5 wt. % (by KF). The final MTBE concentration was 11-12 wt. % (as a hemisolvate) and the final heptane concentration was <0.5 wt. % (both by GC). The chiral amide/MTBE hemisolvate was isolated in 90% yield, 99.3 LCAP.

EXAMPLE 16

N-[1S,2S]-3-(4-chlorophenyl)-2-(3-cyanophenyl)-1-methylpropyl]-2-methyl-2-{[5-(trifluoromethyl pyridin-2-yl)oxy]propanamide Route A Step A: Catalyst Preparation In a $N_2$-filled glove box, ((R,S)-((di-t-butylphosphino)ferrocenyl-ethyldi-3,5-dimethylphenyl-phosphine), 300 mg) was added to a 30 mL bottle containing a stir bar. $(NBD)_2RhBF_4$ (183 mg) was added to the same bottle and then 1,2-dichloroethane (20 mL) was added. The resulting solution was aged with stirring for 1 hour, and the resulting mixture was added to a 50 mL stainless steel bomb.

Step B: Hydrogenation

In a $N_2$-filled glove box, starting cyanoenamide (product of Example 4, 10 g) was diluted with 100 mL of 1,2-dichloroethane, and the solution was transferred to a 150 mL stainless steel bomb connected to the 50 mL stainless steel bomb containing the catalyst solution. The 150 mL bomb was connected to the autoclave via flexible polyethylene tubing (flushed with $N_2$) and the substrate solution was drawn into the autoclave followed by the catalyst solution from the upper chamber. The autoclave was sealed and degassed with $N_2$ purges three times. The autoclave was then degassed with $H_2$ purges three times, and pressurized up to 500 psi. The stirrer

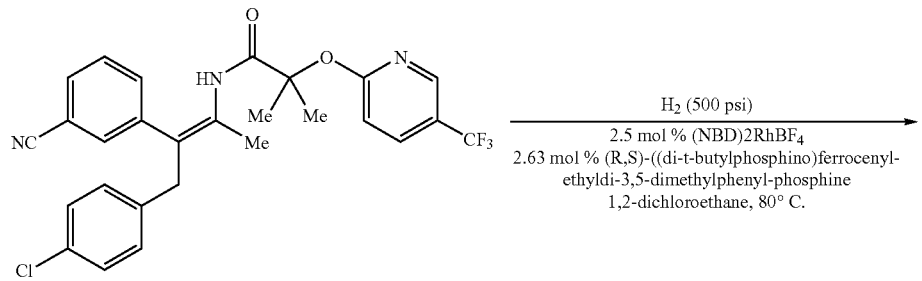

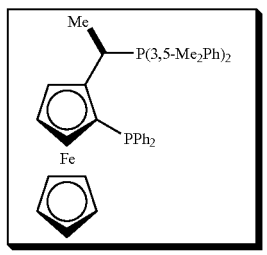

(R,S)-((di-t-butylphosphino)ferrocenyl-ethyldi-3,5-dimethylphenyl-phosphine was initiated, and the temperature was raised to 80° C. The reaction was aged at 500 psi, 80° C. for 18 hours. The temperature was dropped to room temperature, and the resulting solution was transferred to an amber jar and assayed for ee and purity (9.5 g assay of cyanoenamide, 95% assay yield, 90% LCAP, 85% ee).

EXAMPLE 17

3-{(1S,2S)-1-(4-chlorobenzyl)-2-[(2-methyl-2-{[5-(trifluoromethyl)pyridine-2-yl]oxy}propanoyl)amino]-propyl}benzamide Route B Hydrogenation using ((R,S)-((di-t-butylphosphino)ferrocenyl-ethyldi-o-tolylphosphine)

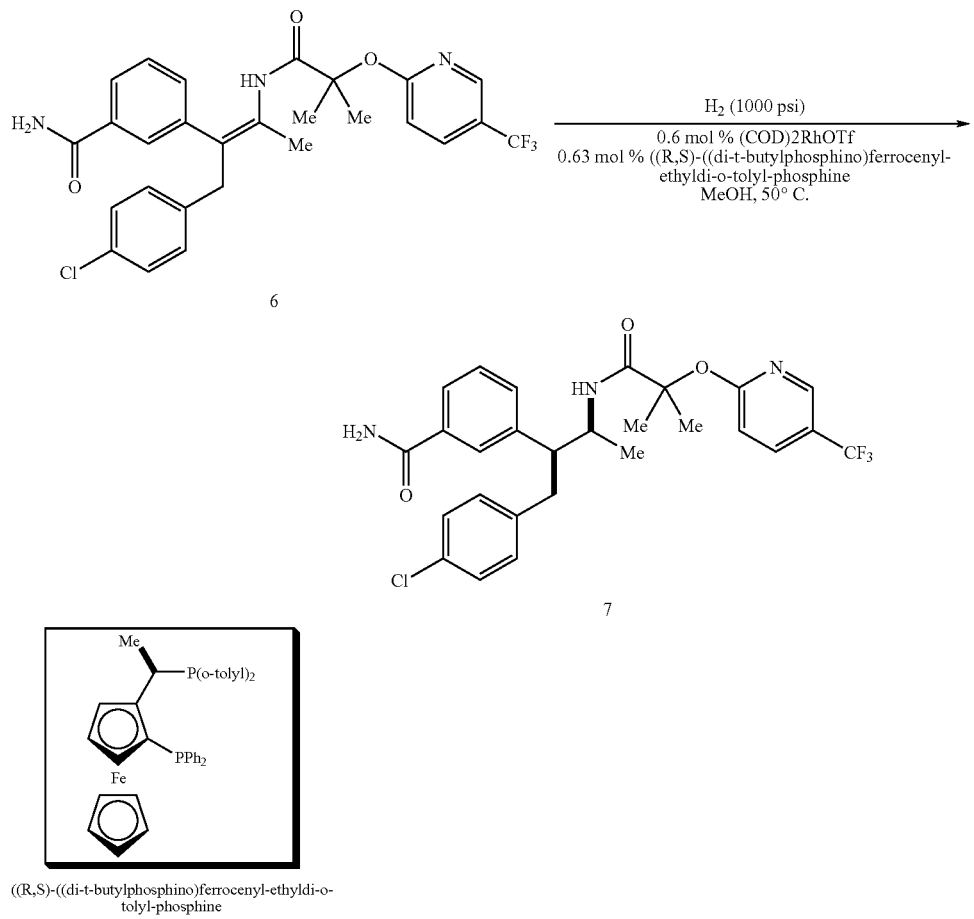

In a $N_2$-filled glove box, (R,S)-((di-t-butylphosphino)ferrocenyl-ethyldi-o-tolylphosphine) (57.1 mg) was added to a 20 mL vial containing a stir bar. $(COD)_2RhOTf$ (46.8 mg) was added to the same vial and then MeOH (20 mL) was added. The resulting solution was aged with stirring for 20 minutes, and the resulting mixture was added to a 150 mL stainless steel bomb. In a $N_2$-filled glove box, enamide 6 (8.0 g, product of Example 7) was dissolved with 50 mL of MeOH, and the solution was transferred to the same 150 mL stainless steel bomb as the catalyst along with a 10 mL flask rinse. The 150 mL stainless steel bomb was connected to a 25 mL stainless steel rinse bomb containing 10 mL MeOH. The bomb assembly was connected to the autoclave via flexible polyethylene tubing (flushed with $N_2$) and the reaction solution was drawn into the autoclave followed by the MeOH rinse solvent from the upper chamber. The autoclave was sealed and degassed with $N_2$ purges three times. The autoclave was then degassed with $H_2$ purges three times, and pressurized up to 1000 psi. The stirrer was initiated, and the temperature was raised to 50° C. The reaction was aged at 1000 psi, 50° C. for 23.5 hours. The temperature was dropped to room temperature, and the resulting solution was transferred to an amber jar and assayed for ee and purity (98.0% LCAP 7, 92.8% ee 0.2% LCAP enamide 6).

EXAMPLE 18

Isolation of Crystal Type 1 Solvate of 3-{(1S,2S)-1-(4-chlorobenzyl)-2-[(2-methyl-2-{[5-(trifluoromethyl)-pyridine-2-yl]oxy}propanoyl)amino]-propyl}benzamide 3-{(1S,2S)-1-(4-chlorobenzyl)-2-[(2-methyl-2-{[5-(trifluoromethyl)-pyridine-2-yl]oxy}propanoyl)amino]- propyl}benzamide (540 g) was dissolved to a volume of 1.4 L with IPAc. Cyclohexane (1.95 L) was added and the batch was seeded with crystalline hemi-solvate 3-{(1S,2S)-1-(4-chlorobenzyl)-2-[(2-methyl-2-{[5-(trifluoromethyl)-pyridine-2-yl]oxy}propanoyl)amino]-propyl}benzamide (Example 11). After a 20 min age, cyclohexane (13.25 L) was added over 1.5 h. The batch was aged for 1.5 h at RT then cooled to 5° C. with a water-ice bath. The slurry was filtered and washed with cyclohexane (500 mL). The batch was dried in a 35° C. vacuum oven with a nitrogen sweep. ML losses were 48 g (8.8%). The final solid weighed 442.8 g (94 wt % therefore 416 g).

EXAMPLE 19

Isolation of Crystal Type 2 Solvate of 3-{(1S,2S)-1-(4-chlorobenzyl)-2-[(2-methyl-2-{[5-(trifluoromethyl)-pyridine-2-yl]oxy}propanoyl)amino]-propyl}benzamide 3-{(1S,2S)-1-(4-chlorobenzyl)-2-[(2-methyl-2-{[5-(trifluoromethyl)-pyridine-2-yl]oxy}propanoyl)amino]-propyl}benzamide (1012 g) was charged and dissolved to a volume of 4.1 L with MTBE. The batch was seeded with crystalline hemi-solvate 3-{(1S,2S)-1-(4-chlorobenzyl)-2-[(2-methyl-2-{[5-(trifluoromethyl)-pyridine-2-yl]oxy}propanoyl)amino]-propyl}benzamide (Example 11). After a 20 min age, heptane (12.3 L) was added over 1.5 h. The batch was aged for 1.5 h at RT then cooled to 5° C. with a water-ice bath. The slurry was filtered and washed with heptane (2.1 L). The batch was dried in under vacuum with a nitrogen sweep. ML losses were 38 g (3.7%). The final solid weighed 1011 g (93 wt % therefore 940 g).

EXAMPLE 20

Isolation of Crystal Type 3 Solvate of 3-{(1S,2S)-1-(4-chlorobenzyl)-2-[(2-methyl-2-{[5-(trifluoromethyl)-pyridine-2-yl]oxy}propanoyl)amino]-propyl}benzamide Following the bicarbonate treatment as in Example 7, 3-{(1S,2S)-1-(4-chlorobenzyl)-2-[(2-methyl-2-{[5-(trifluoromethyl)-pyridine-2-yl]oxy}propanoyl amino]-propyl}benzamide (2.4 g) was dissolved in 80 mL MTBE. Solvent was switched from MTBE to toluene at 35° C. A final volume of ~45 mL was maintained. 15 wt % (0.36 g) of Ecosorb C941 was added and batch aged at 70 to 75° C. Over 90 min. Cooled to rt and filtered over CELITE. The colorless solution was concentrated to dryness and 3 mL (~1.2V) of IPAc was added and kept at 60° C. Then 21 mL of Isooctane was charged over 30 min. Solution was cooled slowly and self seeded at 56° C. (a small amount of the solution is sampled into a vial and cooled to rt to generate the seeds). Once the sample crystallized, it was returned to the batch. Batch became a slurry as it was cooled slowly to rt (over 3 h). Batch was aged at rt over 2 h. A slightly wet solid collected and was left in vacuum oven to dry overnight at 35° C. Solid HPLC assay gave 99.2 A % and 98 wt %. Chiral HPLC=90.4% ee. NMR results indicate it is an isooctane solvate.

EXAMPLE 21

Analysis of Crystal forms of 3-{(1S,2S)-1-(4-chlorobenzyl)-2-[(2-methyl-2-{[5-(trifluoromethyl)-pyridine-2-yl]oxy}propanoyl)amino]-propyl}benzamide A single crystal was selected for single crystal x-ray data collection on a Bruker Smart Apex system. The unit cell was collected on 30 second scan rate and auto-indexing gave the cell setting to be triclinic. The structure was solved in the triclinic P1 space group after a quadrant data collection using 30 second scan rate.

The X-ray powder diffraction patterns were generated on Philips Analytical X'Pert PRO X-ray Diffraction System with PW3040/60 console. A PW3373/00 ceramic Cu LEF X-ray tube K-Alpha radiation was used as the source. The experiments were run at ambient condition.

In addition to the X-ray powder diffraction patterns, the forms of 3-{(1S,2S)-1-(4-chlorobenzyl)-2-[(2-methyl-2-{[5-(trifluoromethyl)-pyridine-2-yl]oxy}propanoyl)amino]-propyl}benzamide were further characterized by their solid-state carbon-13 and fluorine-19 nuclear magnetic resonance (NMR) spectra. The solid-state carbon-13 NMR spectrum was obtained on a Bruker DSX 400WB NMR system using a Bruker 4 mm double resonance CPMAS probe. The carbon-13 NMR spectrum utilized proton/carbon-13 cross-polarization magic-angle spinning with variable-amplitude cross polarization. The sample was spun at 15.0 kHz. A line broadening of 40 Hz was applied to the spectrum before FT was performed. Chemical shifts are reported on the TMS scale using the carbonyl carbon of glycine (176.03 p.p.m.) as a secondary reference.

The solid-state fluorine-19 NMR spectrum was obtained on a Bruker DSX 400WB NMR system using a Bruker 4 mm CRAMPS probe. The NMR spectrum utilized a simple pulse-acquire pulse program. The samples were spun at 15.0 kHz. A vespel endcap was utilized to minimize fluorine background. A line broadening of 100 Hz was applied to the spectrum before Fr was performed. Chemical shifts are reported using poly(tetrafluoroethylene) (TEFLON) as an external secondary reference which was assigned a chemical shift of −122 ppm.

While the invention has been described and illustrated with reference to certain particular embodiments thereof, those skilled in the art will appreciate that various changes, modifications and substitutions can be made therein without departing from the spirit and scope of the invention. For example, solvents other than the particular solvents as set forth herein above may be useful in the chemical syntheses described herein. It is intended, therefore, that the invention be defined by the scope of the claims which follow and that such claims be interpreted as broadly as is reasonable.

The invention claimed is:
1. A process for the stereoselective synthesis of amide (I):

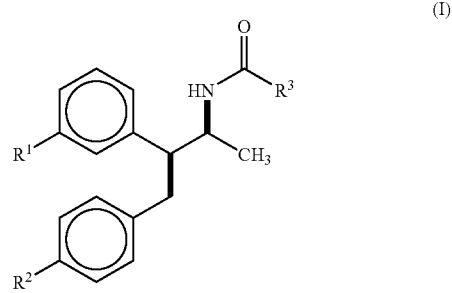

wherein:
$R^1$ is selected from: hydrogen, halogen, —C(O)OR$^e$, —C(O)NR$^f_2$, —NR$^f_2$, and cyano;
$R^2$ is selected from: hydrogen, halogen and hydroxyl;

$R^3$ is

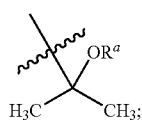

$R^a$ is:

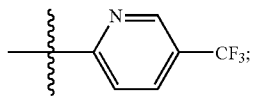

each $R^c$ is independently selected from halogen, hydroxy, $C_{1-3}$ alkyl, cyano, methoxy and trifluoromethyl;

each $R^d$ is independently selected from: halogen, hydroxy, cyano, methoxy and trifluoromethyl;

$R^e$ is selected from: hydrogen, straight or branched chain $C_{1-10}$ alkyl, aryl-$C_{1-6}$ alkyl-, aryl, heteroaryl, wherein aryl and heteroaryl moieties are optionally substituted with one to three $R^c$ substituents, and the alkyl moiety is unsubstituted or substituted with one, two or three $R^d$ moieties; each $R^f$ is independently selected from hydrogen, straight or branched chain $C_{1-6}$ alkyl, phenyl-$C_{1-6}$ alkyl-, wherein alkyl moieties are unsubstituted or substituted with one or two $R^d$ substituents and wherein the phenyl moiety is unsubstituted or substituted with one, two or three $R^c$ substituents; comprising treating an enamide compound formula (II):

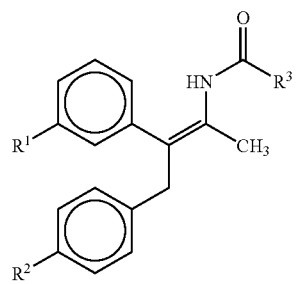

with hydrogen gas in the presence of a chiral catalyst.

2. The process according to claim 1, wherein the chiral catalyst is selected from:
   (1) a chiral catalyst formed in situ by contacting a metal precursor, a ligand and optionally an activator; and
   (2) a preformed catalyst complex.

3. The process according to claim 1 wherein:
$R^1$ is selected from amido and cyano;
$R^2$ is selected from hydrogen and chlorine;
$R^3$ is

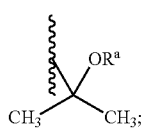

and $R^a$ is:

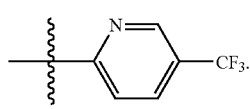

4. The process according to claim 3 wherein:
$R^1$ is cyano; $R^2$ is chlorine; $R^3$ is:

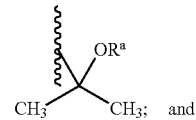 and $R^a$ is

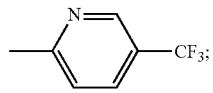

the chiral catalyst is selected from:
   (1) a chiral catalyst formed in situ by contacting a metal precursor, a ligand and optionally an activator; wherein the metal precursor is selected from: $(COD)_2RhBF_4$, $[(COD)RhCl]_2$, $[(NBD)RhCl]_2$, $(COD)_2RhOTf$, $(NBD)_2RhBF_4$, $(NBD)_2RhOTf$, and $(COD)Ru(methallyl)_2$; the ligand is selected from: (R,S)-(di-t-butylphosphino)ferrocenyl-ethyldi-3,5-dimethylphenylphosphine, (−)-TMBTP, and (R)-Hexaphemp; and the activator is absent or tetrafluoroboric acid; and
   (2) a preformed catalyst complex: (R,S)-(di-t-butylphosphino)ferrocenyl-ethyldi-3,5-dimethylphenylphosphine $(COD)RhBF_4$.

5. The process according to claim 3 wherein:
$R^1$ is amido; $R^2$ is chlorine; $R^3$ is:

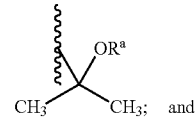 and $R^a$ is

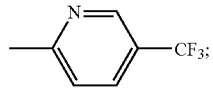

the hydrogen pressure is from 1 to 100 atmospheres,
the temperature is from ambient to 90° C.
the solvent is selected from pure or mixtures of: MeOH, EtOH, IPA, 2,2,2-trifluoroethanol, THF and 1,2-dichloroethane
the chiral catalyst is selected from:
   (1) a chiral catalyst formed in situ by contacting a metal precursor, a ligand and optionally an activator; wherein the metal precursor is selected from: $(COD)_2RhBF_4$, $(COD)_2RhOTf$, $(NBD)_2RhBF_4$, $(NBD)_2RhOTf$, and $(COD)Ru(methallyl)_2$; the ligand is selected from: (R,S)-(di-t-butylphosphino)ferrocenyl-ethyldi-o-tolylphosphine, (R,S)-(di-t-butylphosphino)ferrocenyl-ethyldi-1-napthylphosphine, (R,S)-(di-t-butylphosphino)ferrocenyl-ethyldi-3,5-dimethylphenylphosphine, (R,S)-(diphenylphosphino)ferrocenyl-ethyldi-t-butylphosphine, (−)-TMBTP, (R)-hexaphemp, (R)-xyl-BINAP, the activator is absent or tetrafluoroboric acid; or
(2) a preformed catalyst complex selected from: (−)-TMBTP(COD)RhBF$_4$, (−)-TMBTP(COD)RhOTf, (−)-TMBTP(NBD)RhBF$_4$, or (−)-TMBTP(NBD)RhOTf, ((R,S)-(di-t-butylphosphino)ferrocenyl-ethyldi-o-tolylphosphine)(COD)RhBF$_4$, ((R,S)-(di-t-butylphosphino)ferrocenyl-ethyldi-o-tolylphosphine)(COD)RhOTf, ((R,S)-(di-t-butylphosphino)ferrocenyl-ethyldi-o-tolylphosphine)(NBD)RhBF$_4$, or ((R,S)-(di-t-butylphosphino)ferrocenyl-ethyldi-o-tolylphosphine)(NBD)RhOTf additionally comprising an additive selected from: tetrafluoroboric acid, trifluoroacetic acid, BF$_3$, BF$_3$.IPA and BF$_3$.MeOH.

6. The process according to claim 5 wherein:
$R^1$ is amido; $R^2$ is chlorine; $R^3$ is:

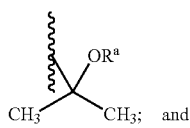

and $R^a$ is

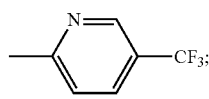

the hydrogen pressure is from 10-40 atmospheres,
the temperature is from 35 to 65° C.
the solvent is selected from pure or mixtures of: MeOH, IPA and 2,2,2-trifluoroethanol
the chiral catalyst is selected from:
(1) a chiral catalyst formed in situ by contacting a metal precursor, a ligand and optionally an activator; wherein the metal precursor is selected from: (COD)$_2$RhBF$_4$, (COD)$_2$RhOTf, (NBD)$_2$RhBF$_4$, and (NBD)$_2$RhOTf, the ligand is selected from: (R,S)-(di-t-butylphosphino)ferrocenyl-ethyldi-o-tolylphosphine and (−)-TMBTP, the activator is absent; or
(2) a preformed catalyst complex selected from: (−)-TMBTP(COD)RhBF$_4$, ((R,S)-(di-t-butylphosphino)ferrocenyl-ethyldi-o-tolylphosphine)(COD)RhBF$_4$, ((R,S)-(di-t-butylphosphino)ferrocenyl-ethyldi-o-tolylphosphine)(COD)RhOTf, ((R,S)-(di-t-butylphosphino)ferrocenyl-ethyldi-o-tolylphosphine)(NBD)RhBF$_4$ optionally comprising an additive selected from: BF$_3$.IPA and BF$_3$.MeOH.

7. The process according to claim 3 wherein:
$R^1$ is amido; $R^2$ is chlorine; $R^3$ is:

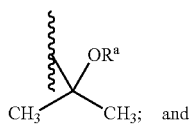

and $R^a$ is

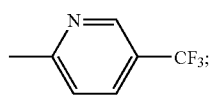

the hydrogen pressure is from 20 to 40 atmospheres,
the chiral catalyst is selected from:

(1) a chiral catalyst formed in situ by contacting a metal precursor, a ligand and optionally an activator; wherein the metal precursor is selected from:
(COD)$_2$RhBF$_4$, (COD)$_2$RhOTf, (NBD)$_2$RhBF$_4$, (NBD)$_2$RhOTf,
and (COD)Ru(methallyl)$_2$; the ligand is selected from: (R,S)-(di-t-butylphosphino)ferrocenyl-ethyldi-o-tolylphosphine, (R,S)-(diphenylphosphino)ferrocenyl-ethyldi-t-butylphosphine, (−)-TMBTP, (R)-hexaphemp, (R)-xyl-BINAP, the activator is absent or tetrafluoroboric acid; and
(2) a preformed catalyst complex: (−)-TMBTP(COD)RhBF$_4$;
additionally comprising an additive selected from: tetrafluoroboric acid, trifluoroacetic acid and BF$_3$.MeOH.

8. The process according to claim 1, wherein the enamide compound of formula (II):

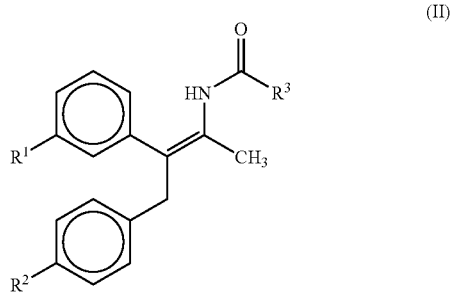

wherein:
$R^1$, $R^2$, and $R^3$ are as defined in claim 1,
is prepared by treating a compound of formula (III):

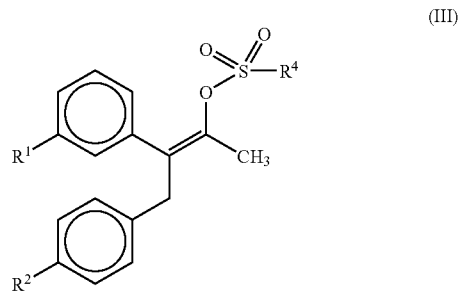

with amide (IV):

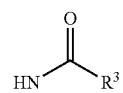

in the presence of a base and a palladium catalyst;
wherein:
$R^4$ is selected from: aryl, heteroaryl and $C_{1-10}$ alkyl, wherein the aryl and heteroaryl moieties are unsubstituted or substituted with one to three $R^c$ substituents, and the alkyl moiety is unsubstituted or substituted with one or two $R^d$ substituents;
$R^1$, $R^2$, $R^3$, $R^a$, $R^b$ $R^c$, $R^d$, $R^e$, and $R^f$ are as defined in claim 1.

9. The process according to claim 8, wherein:
$R^1$ is selected from amido and cyano;
$R^2$ is selected from hydrogen and chlorine;
$R^3$ is

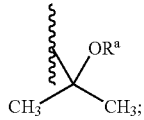

$R^4$ is selected from phenyl, unsubstituted or substituted with an $R^e$ substituents;
and $R^a$ is:

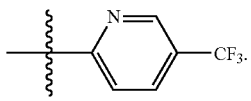

10. The process according to claim 9, wherein:
$R^1$ is cyano, $R^2$ is chlorine, $R^3$ is:

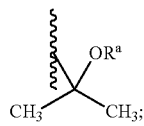

$R^4$ is 4-methylphenyl; and
$R^a$ is

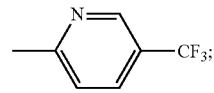

the base is potassium carbonate, the palladium catalyst is selected from tris(dibenzylideneacetone) dipalladium (0), and bis(dibenzylideneacetone)palladium(0); and
the palladium catalyst additionally comprises a phosphine ligand selected from 1,4-bis(diphenylphosphino)butane, and 1,1'-bis(diisopropylphosphino)ferrocene.

\* \* \* \* \*